US010392397B2

United States Patent
Tao et al.

(10) Patent No.: US 10,392,397 B2
(45) Date of Patent: Aug. 27, 2019

(54) HETEROCYCLIC THIOSEMICARBAZONE DERIVATIVES AND THEIR THERAPEUTICAL APPLICATIONS

(71) Applicants: NANTBIO, INC., Culver City, CA (US); NANT HOLDINGS IP, LLC, Culver City, CA (US)

(72) Inventors: Chunlin Tao, Newport Coast, CA (US); Qinwei Wang, Culver City, CA (US); Patrick Soon-Shiong, Culver City, CA (US)

(73) Assignees: NantBio, Inc., Culver City, CA (US); Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 15/745,588

(22) PCT Filed: Aug. 8, 2016

(86) PCT No.: PCT/US2016/046078
§ 371 (c)(1),
(2) Date: Jan. 17, 2018

(87) PCT Pub. No.: WO2017/024315
PCT Pub. Date: Feb. 9, 2017

(65) Prior Publication Data
US 2018/0208603 A1 Jul. 26, 2018

Related U.S. Application Data

(60) Provisional application No. 62/202,158, filed on Aug. 6, 2015.

(51) Int. Cl.
| | | |
|---|---|---|
| C07D 491/048 | (2006.01) | |
| C07D 491/044 | (2006.01) | |
| C07D 491/052 | (2006.01) | |
| C07D 471/04 | (2006.01) | |
| C07D 495/04 | (2006.01) | |
| A61P 35/00 | (2006.01) | |

(52) U.S. Cl.
CPC .......... *C07D 491/052* (2013.01); *A61P 35/00* (2018.01); *C07D 471/04* (2013.01); *C07D 491/044* (2013.01); *C07D 491/048* (2013.01); *C07D 495/04* (2013.01)

(58) Field of Classification Search
None
See application file for complete search history.

(56) References Cited

U.S. PATENT DOCUMENTS

| 5,428,027 A * | 6/1995 | Daub .................... C07C 281/12 514/100 |
| 8,367,675 B2 | 2/2013 | Danter et al. |
| 8,895,556 B2 | 11/2014 | Danter et al. |
| 2010/0015140 A1* | 1/2010 | Danter ................. C07D 401/12 424/133.1 |

FOREIGN PATENT DOCUMENTS

WO 2013181931 A1 12/2013

OTHER PUBLICATIONS

Merlot, Angelica. Antioxidants & Redox Signaling 18(8) (2013) 973-1006.*
Myeloproliferative disorders: University of Maryland Medical Center. (2016).Web: <http://umm.edu/health/medical/altmed/condition/myeloproliferative-disorders>.*
MedicineNet.com (2004) Web <http://www.medterms.com>.*
Rouhi, Maureen. Chem. & Eng. News, (2003), 81(8), 32-35.*
Morissette, Sherry. Adv. Drug Delivery Rev. 2004, 56, 275-300.*
Patani, George. Chem. Rev. 96 (1996) 3147-3176.*
Henan Normal University, "1,4-dihydroxy-2-formyl-9,10 anthraquinone thiosemicarbazone new compound with anticancer activity and preparation method thereof," CN 102627593 A, Aug. 8, 2012. (Abstract; claims 1-10).
PCT International Search Report and Written Opinion for the corresponding PCT Application No. PCT/US2016/046078, filed Aug. 8, 2016. (14 Pages).

* cited by examiner

*Primary Examiner* — Emily A Bernhardt
*Assistant Examiner* — Laura M Daniel
(74) *Attorney, Agent, or Firm* — Lucas & Mercanti, LLP

(57) ABSTRACT

Pharmaceutical compounds, compositions, and methods are presented in which various heterocyclic thiosemicarbazone derivatives are prepared. Contemplated compounds will be suitable to inhibit or reduce cellular growth or proliferation and are thus beneficial in the manufacture of drugs to treat neoplastic diseases.

11 Claims, No Drawings

HETEROCYCLIC THIOSEMICARBAZONE DERIVATIVES AND THEIR THERAPEUTICAL APPLICATIONS

CROSS-REFERENCE TO RELATED APPLICATIONS

This application is a U.S. national stage of PCT Application No. PCT/US16/46078 filed on Aug. 8, 2016, which claims the benefit of priority from U.S. Provisional Application Ser. No. 62/202,158 filed on Aug. 6, 2015.

FIELD OF THE INVENTION

The field of the invention is pharmaceutically active compounds, compositions, and methods therefor, and particularly as it relates to thiosemicarbazone derivatives.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer is one of the leading causes of death worldwide and accounts for 7.9 million deaths (around 13% of all deaths) in 2014 and with an estimated 13 million deaths in 2030. Over the last 50 years, many molecules have been developed as anticancer reagents against various types of cancers. The majority of anticancer molecules in the clinical world exert their activity by inhibiting cellular processes in normal or cancerous cells. It is important to have significant anticancer molecules with less effect on normal cells and considerable effect on the cancer cells (and targets), which is a major hurdle nowadays. However, a high percentage of them fail clinically due to their lack of selectivity and adverse effects (including toxicity).

Thiosemicarbazones are a class of small molecules that have been evaluated over the last 50 years as antivirals (*Arch. Pharm.* (Weinheim) 2002, 335, 183-186; *Virology* 1991, 185, 857-861) and as anticancer therapeutics (*Adv. Enzyme Regul.* 1999, 39, 3-12), as well as for their parasiticidal action against *Plasmodium falciparum* (*J. Med. Chem.* 1979, 22, 855-862). A variety of thiosemicarbazone derivatives have also been reported as anticancer agents, incuding pyrazolone-substituted thiosemicarbazone derivatives (WO 2007/142308), liquiritigenin thiosemicarbazone derivatives (*European Journal of Medicinal Chemistry* (2010), 45(8), 3453-3458), N,N-diaryl(thio)ureas derirvatives (WO 2010/138820), thio-carbonyl compounds as antitumor agents (CN 101759692), piperazine hydroxamates as histone deacetylase (HDAC) inhibitors (*Bioorganic & Medicinal Chemistry Letters* (2010), 20(13), 3906-3910), various 3-thylidenehydrazino-substituted heterocyclic compounds (WO 2006/062240) and heteoaryl-thiosemicarbazone and semicarbazone derivatives (WO 2009/079797, WO 2008/083491) as well as pyridinyl-thiosemicarbazides derivatives (CN 1224005).

Moreover, thiosemicarbazones and their metal complexes present a wide range of bioactivities as antimicrobial, antitumor, antiviral and antiprotozoal agents (*Medicinal Chemistry Research* (2013), 22(6), 2802-2808). It was also reported that Pd(II) complexes of certain 1-N-substituted 3-phenyl-2-pyrazoline derivatives (*European Journal of Medicinal Chemistry* (2008), 43(2), 393-403) and zinc(II) complexes of 2-acetyl pyridine 1-(4-fluorophenyl)-piperazinyl thiosemicarbazone derivatives (*Journal of Inorganic Biochemistry* (2010), 104(4), 467-476) present cytotoxic activity against MCF-7, TK-10 and UACC-62 human tumor cell lines and were able to induce cell death by apoptosis. Platinum(II) and palladium(II) complexes with 2-acetyl pyridine 4N-ethyl thiosemicarbazone were also shown to overcome cisplatin resistance (*BioMetals* (2003), 16(3), 411-418).

More recently, certain thiosemicarbazone compounds were also reported to target the metastasis suppressor, NDRG1. NDRG1 inhibits both growth and metastasis as well as angiogenesis of pancreatic cancer in vivo, leading to reduced tumor progression. NDRG1 is also correlated with increased differentiation of pancreatic cancers (*Carcinogenesis* (2006) 27: 2355-66; *Cancer Res* (2006) 66: 6233-42). Further, various alkyl piperidine/piperazine thiosemicarbazone compounds were studied for neuron imaging and treatment of various neurodegenerative disease (US 2005/0222166); thiosemicarbazones also represent validated drug leads that kill several species of protozoan parasites through the inhibition of cysteine proteases as well as other novel targets (*Journal of Medicinal Chemistry* (2004), 47(12), 3212-3219). In addition, 3-Aminopyridine-2-carboxaldehyde thiosemicarbazone (Triapine) recently was demonstrated to possess a broad spectrum of activity in animal tumor models and reached clinical phase II as an antineoplastic therapeutic (*Invest. New Drugs*, 2008, 26, 169-173; *Cancer Chemother. Pharmacol.* 2002, 50, 223-229; *Ann. Oncol.*, 2009, 20, 1275-1279).

As is readily apparent from the large diversity of activities, thiosemicarbazone and semicarbazone are important pharmacophores for the development of therapeutics. Although many thiosemicarbazones are taught as cancer therapeutic agents (WO 2008/084391, WO 2007/142308; WO 2009/007997; CN103058995, and CN102653521), all or almost all of them suffer from relatively high toxicity, lack of specificity, and/or therapeutic efficiency. Therefore, there is still a need for new and alternative treatments for cancer with less toxicity and increased efficacy.

SUMMARY OF THE INVENTION

The inventive subject matter is directed to pharmaceutical compounds, compositions, and methods therefor, and particularly to selected heterocyclic thiosemicarbazone derivatives that inhibit or reduce cellular proliferation, for example, in the treatment of cancer.

In one aspect of the inventive subject matter, the inventors contemplate a compound having a structure according to Formula I

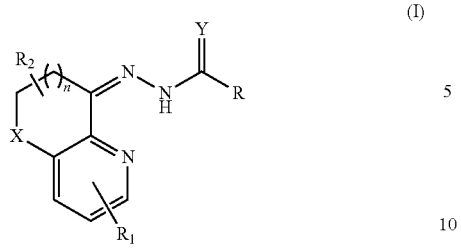
(I)

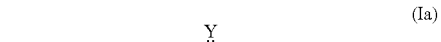
(Ia)

(Ib)

wherein X is O, S, or $NR_7$; Y is O, S, or $NR_8$; n is an integer between 0 and 2, inclusive; $R_1$ is hydrogen, F, Cl, Br, I, CN, $C_1$-$C_4$ alkyl, $C_1$-$C_6$ alkoxy, $C_2$-$C_6$ alkenyl, $CF_3$, $CHF_2$, $CH_2F$, $C_2$-$C_6$ alkynyl, or $CON(R_5)R_6$; $R_2$ is hydrogen, alkyl, cycloalkyl, alkenyl, alkynyl, alkylthio, aryl, arylalkyl, or oxo; and R is (i), (ii), or (iii), wherein (i) is heteroaryl or aryl, each of which is substituted with from 0 to 4 substituents selected from the group of halogen, hydroxy, cyano, $CF_3$, $CHF_2$, $CH_2F$, —COOH, —$SO_2NH_2$, oxo, nitro, $C_1$-$C_4$ alkyl, $C_1$-$C_6$ alkoxy, $C_2$-$C_6$ alkenyl, $C_2$-$C_6$ alkynyl, $CON(R_5)R_6$, $SO_2N(R_5)R_6$, and $N(R_7)R_8$; (ii) is $C_1$-$C_4$ alkyl, $C_1$-$C_6$ alkoxy, $C_2$-$C_6$ alkenyl, $C_2$-$C_6$ alkynyl, $CON(R_5)R_6$, or $N(R_7)R_8$; (iii) is a group having the formula (A):

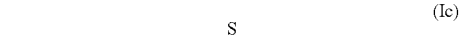
(Ic)

(Id)

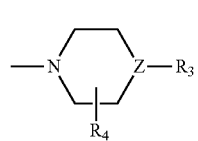
(A)

$R_3$ is selected from the group consisting of hydrogen, $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$cycloalkyl)$C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- or di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- or di-($C_1$-$C_6$ alkyl) sulfonamido, and mono- or di-($C_1$-$C_6$ alkyl)aminocarbonyl, each of which is substituted with from 0 to 4 substituents independently selected from the group consisting of halogen, hydroxy, cyano, amino, —COOH, nitro, $CF_3$, and oxo; $R_4$ is hydrogen, $C_1$-$C_4$ alkyl, or oxo; Z is CH when $R_3$ is hydrogen, or Z—$R_3$ is O, or Z is N; $R_5$ and $R_6$ are independently selected from the group consisting of hydrogen, $C_1$-$C_4$ alkyl, cycloalkyl, alkenyl, and alkynyl; and $R_7$ and $R_8$ are independently selected from the group consisting of hydrogen, $C_1$-$C_4$ alkyl, $C_2$-$C_6$ alkenyl, $C_2$-$C_6$ alkynyl, $C_3$-$C_{10}$ aryl or heteroaryl, $C_2$-$C_6$ acyl, $C_1$-$C_6$ alkoxycarbonyl, and $C_2$-$C_6$ alkanoyloxy, each of which is substituted with from 0 to 4 substituents independently selected from the group consisting of halogen, hydroxy, cyano, amino, —COOH, nitro, $CF_3$, and oxo.

(Ie)

(If)

Therefore, and viewed form a different perspective, compounds are also contemplated have structures according to Formula Ia-Ih -continued

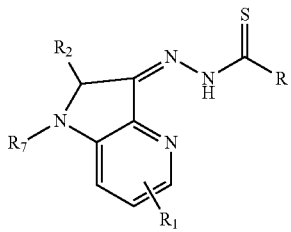

(Ig)

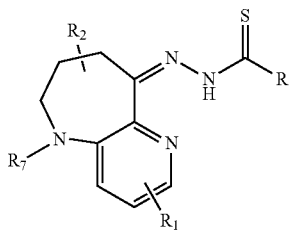

(Ih)

Particularly preferred compounds include those in which Y is S, X is O or NR$_7$, R is (iii) with Z being N, R$_1$ is F, Cl, or C$_1$-C$_4$ alkyl, and in which R$_2$ is hydrogen. Most typically, n is 0 or 1 in some embodiments, while n is 2 in other embodiments.

In further contemplated aspects pharmaceutical compositions are contemplated that comprise a pharmaceutically acceptable carrier in combination with one or more compound presented herein, wherein the compound may be present as a pharmaceutically acceptable salt, a hydrate, a solvate, or in crystalline form. Most preferably, the compound will be present in the pharmaceutical composition in an amount effective to reduce cell growth or proliferation of a cancer cell when administered to a mammal in need thereof, and it is further generally preferred that the composition is formulated for oral administration or injection.

Therefore, the inventors also contemplate the use of one or more compounds presented herein in the manufacture of a pharmaceutical composition, and/or to treat a cancer in a mammal. Viewed from a different perspective, the inventors also contemplate a method for treating and/or preventing a proliferation disorder that typically comprises a step of administering to a subject in need thereof an effective amount of one or more compounds presented herein.

Various objects, features, aspects and advantages of the inventive subject matter will become more apparent from the following detailed description of preferred embodiments.

DETAILED DESCRIPTION

The inventive subject matter is directed towards various pharmaceutical compounds, compositions, and methods therefor, and particularly to heterocyclic thiosemicarbazone derivatives that inhibit or reduce cellular proliferation, for example, in the treatment of cancer. So prepared compounds, compositions and methods are deemed to be useful in the manufacture of a medicament and the treatment of neoplastic diseases responsive to such compounds and compositions. While not wishing to be bound by any particular theory or hypothesis, it is contemplated that the compounds will reduce or inhibit enzymatic activity of one or more members of p53 proteins. Consequently, such compounds may be particularly beneficial for treatment of diseases associated with dysfunction of cell motility, adhesion, and cell cycle progression, as well as for reduction of tumor growth, invasion, angiogenesis, metastasis, and/or induction of apoptosis.

Contemplated Compounds

The present inventive subject matter is related to compounds having general Formula (I) or a pharmaceutically acceptable salt thereof, wherein

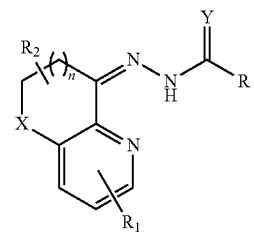

(I)

wherein X is O, S, or NR$_7$; Y is O, S, or NR$_8$; n is an integer between 0 and 2, inclusive; R$_1$ is hydrogen, F, Cl, Br, I, CN, C$_1$-C$_4$ alkyl, C$_1$-C$_6$ alkoxy, C$_2$-C$_6$ alkenyl, CF$_3$, CHF$_2$, CH$_2$F, C$_2$-C$_6$ alkynyl, or CON(R$_5$)R$_6$; R$_2$ is hydrogen, alkyl, cycloalkyl, alkenyl, alkynyl, alkylthio, aryl, arylalkyl, or oxo; and R is (i), (ii), or (iii), wherein (i) is heteroaryl or aryl, each of which is substituted with from 0 to 4 substituents selected from the group of halogen, hydroxy, cyano, CF$_3$, CHF$_2$, CH$_2$F, —COOH, —SO$_2$NH$_2$, oxo, nitro, C$_1$-C$_4$ alkyl, C$_1$-C$_6$ alkoxy, C$_2$-C$_6$ alkenyl, C$_2$-C$_6$ alkynyl, CON(R$_5$)R$_6$, SO$_2$N(R$_5$)R$_6$, and N(R$_7$)R$_8$; wherein (ii) is C$_1$-C$_4$ alkyl, C$_1$-C$_6$ alkoxy, C$_2$-C$_6$ alkenyl, C$_2$-C$_6$ alkynyl, CON(R$_5$)R$_6$, or N(R$_7$)R$_8$; and wherein (iii) is a group having the formula (A):

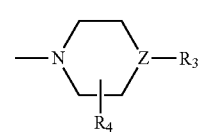

(A)

wherein R$_4$ is hydrogen, C$_1$-C$_4$ alkyl, or oxo; Z is CH, when R$_3$ is hydrogen; or Z—R$_3$ prepresents O; or Z is N; and wherein R$_3$ is selected from the group consisting of hydrogen, C$_1$-C$_6$ alkyl, C$_2$-C$_6$ alkenyl, C$_2$-C$_6$ alkynyl, C$_3$-C$_{10}$ aryl or heteroaryl, (C$_3$-C$_7$cycloalkyl)C$_1$-C$_4$ alkyl, C$_1$-C$_6$ haloalkyl, C$_1$-C$_6$ alkoxy, C$_1$-C$_6$ alkylthio, C$_2$-C$_6$ alkanoyl, C$_1$-C$_6$ alkoxycarbonyl, C$_2$-C$_6$ alkanoyloxy, mono- or di-(C$_3$-C$_8$ cycloalkyl)aminoC$_0$-C$_4$alkyl, (4- to 7-membered heterocycle)C$_0$-C$_4$alkyl, C$_1$-C$_6$ alkylsulfonyl, mono- or di-(C$_1$-C$_6$ alkyl) sulfonamido, and mono- or di-(C$_1$-C$_6$alkyl)aminocarbonyl, each of which is substituted with from 0 to 4 substituents independently selected from the group consisting of halogen, hydroxy, cyano, amino, —COOH, nitro, CF$_3$, and oxo. R$_5$ and R$_6$ are independently selected from the group consisting of hydrogen, C$_1$-C$_4$ alkyl, cycloalkyl, alkenyl, and alkynyl. R$_7$ and R$_8$ are independently selected from the group consisting of hydrogen, C$_1$-C$_4$ alkyl, C$_2$-C$_6$ alkenyl, C$_2$-C$_6$ alkynyl, C$_3$-C$_{10}$ aryl or heteroaryl, C$_1$-C$_6$ alkoxycarbonyl, C$_2$-C$_6$ acyl, and C$_2$-C$_6$ alkanoyloxy, each of which is substituted with from 0 to 4 substituents independently selected from the group consisting of halogen, hydroxy, cyano, amino, —COOH, nitro, CF$_3$, and oxo.

The term "halo" or "halogen" refers to fluorine, chlorine, bromine or iodine.

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like. Exemplary substituents include one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some preferred embodiments of the present inventive subject matter, alkyl groups are substituted with, for example, amino, heterocycloalkyl, such as morpholine, piperazine, piperidine, azetidine, hydroxyl, methoxy, or heteroaryl groups such as pyrrolidine, The term "cycloalkyl" herein alone or as part of another group refers to fully saturated and partially unsaturated hydrocarbon rings of 3 to 9, preferably 3 to 7 carbon atoms. The examples include cyclopropyl, cyclobutyl, cyclopentyl and cyclohexyl, and like. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" are independently hydrogen, alkyl, substituted alkyl, or cycloalkyl, or where R' and R" together form a heterocyclo or heteroaryl ring.

The term "alkenyl" herein alone or as part of another group refers to a hydrocarbon radical straight, branched or cyclic containing from 2 to 12 carbon atoms and at least one carbon to carbon double bond. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, and like. Alkenyl groups may also be substituted at any available point of attachment. Exemplary substituents for alkenyl groups include those listed above for alkyl groups, and especially include C3 to C7 cycloalkyl groups such as cyclopropyl, cyclopentyl and cyclohexyl, which may be further substituted with, for example, amino, oxo, hydroxyl, etc.

The term "alkynyl" refers to straight or branched chain alkyne groups, which have one or more unsaturated carbon-carbon bonds, at least one of which is a triple bond. Alkynyl groups include C2-C8 alkynyl, C2-C6 alkynyl and C2-C4 alkynyl groups, which have from 2 to 8, 2 to 6 or 2 to 4 carbon atoms, respectively. Illustrative of the alkynyl group include ethenyl, propenyl, isopropenyl, butenyl, isobutenyl, pentenyl, and hexenyl. Alkynyl groups may also be substituted at any available point of attachment. Exemplary substituents for alkynyl groups include those listed above for alkyl groups such as amino, alkylamino, etc. The numbers in the subscript after the symbol "C" define the number of carbon atoms a particular group can contain.

The term "alkoxy" alone or as part of another group denotes an alkyl group as described above bonded through an oxygen linkage (—O—). Preferred alkoxy groups have from 1 to 8 carbon atoms. Examples of such groups include the methoxy, ethoxy, n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "alkylthio" refers to an alkyl group as described above attached via a sulfur bridge. Preferred alkoxy and alkylthio groups are those in which an alkyl group is attached via the heteroatom bridge. Preferred alkylthio groups have from 1 to 8 carbon atoms. Examples of such groups include the methylthio, ethylthio, n-propythiol, n-butylthiol, and like.

The term "oxo" as used herein, refers to a keto (C=O) group. An oxo group that is a substituent of a non-aromatic carbon atom results in a conversion of —$CH_2$— to —C(=O)—.

The term "alkoxycarbonyl", alone or as part of another group, denotes an alkoxy group bonded through a carbonyl group. An alkoxycarbonyl radical is represented by the formula: —C(O)OR, where the R group is, for example, a straight or branched $C_1$-$C_6$ alkyl group, cycloalkyl, aryl, or heteroaryl.

The term "arylalkyl" herein alone or as part of another group denotes an aromatic ring bonded through an alkyl group (such as benzyl) as described above.

The term "aryl", alone or as part of another group, refers to monocyclic or bicyclic aromatic rings, e.g., phenyl, substituted phenyl and the like, as well as aromatic ring systems where rings are fused, e.g., napthyl, phenanthrenyl and the like. An aryl group may thus contain at least one ring having at least 6 atoms, with up to five such rings being present, containing up to 20 atoms therein, with alternating (resonating) double bonds between adjacent carbon atoms or suitable heteroatoms. Aryl groups may optionally be substituted with one or more groups including, halogen, alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol.

The term "aromatic" refers to a cyclically conjugated molecular entity with a stability, due to delocalization, significantly greater than that of a hypothetical localized structure, such as the Kekule structure.

The term "amino" herein alone or as part of another group refers to —$NH2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "alkylsulfonyl" refers to groups of the formula ($SO2$)-alkyl, in which the sulfur atom is the point of attachment. Preferably, alkylsulfonyl groups include C1-C6 alkylsulfonyl groups, which have from 1 to 6 carbon atoms. Methylsulfonyl is one representative alkylsulfonyl group.

The term "heteroatom" refers to any atom other than carbon, for example, N, O, or S.

The term "heteroaryl" herein refers to an aromatic carbocyclic radical in which at least one ring atom is a heteroatom independently selected from nitrogen, oxygen, and sulfur, the remaining ring atoms being carbon. Heteroaryl groups may be optionally substituted with one or more substituents described herein. In one example, the heteroaryl group contains 1 to 9 carbon ring atoms ($C_1$-$C_9$). In other examples, the heteroaryl group is $C_1$-$C_5$, $C_3$-$C_5$ or $C_4$-$C_5$. In one embodiment, exemplary heteroaryl groups include 5-10-membered rings or 5-6-membered rings, or monocyclic aromatic 5-, 6- and 7-membered rings containing one or more heteroatoms independently selected from nitrogen, oxygen, and sulfur. In another embodiment, exemplary heteroaryl groups include fused ring systems of up to 10, or in another example 9, carbon atoms wherein at least one aromatic ring contains one or more heteroatoms independently selected from nitrogen, oxygen, and sulfur. "Heteroaryl" includes heteroaryl groups fused with an aryl, cycloalkyl, or other heterocyclyl group. Examples of heteroaryl groups include pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, pyrrolopyrimidinyl, pyrazolopyrimidinyl and furopyridinyl.

In certain embodiments, the heterocyclyl or heteroaryl group is C-attached. By way of example and not limitation, carbon bonded heterocyclyls include bonding arrangements at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. (2-pyridyl, 3-pyridyl, 4-pyridyl, 5-pyridyl, 6-pyridyl).

In certain embodiments, the heterocyclyl or heteroaryl group is N-attached. By way of example and not limitation, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "heterocycle" or "heterocycloalkyl", alone or as part of another group, refers to a cycloalkyl group (non-aromatic) in which one of the carbon atoms in the ring is replaced by a heteroatom selected from O, S and N. The "heterocycle" may have from 1 to 3 fused, pendant, or Spiro rings, at least one of which is a heterocyclic ring (i.e., one or more ring atoms is a heteroatom, with the remaining ring atoms being carbon). The heterocyclic ring may be optionally substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy; lower alkyl), alkoxycarbonyl (preferably a lower alkoxycarbonyl), alkylcarbonyloxy (preferably a lower alkylcarbonyloxy), and aryl (preferably phenyl), the aryl being optionally substituted by halo, lower alkyl and lower alkoxy groups. A heterocyclic group may generally be linked via any ring or substituent atom, provided that a stable compound results.

Typically, a heterocyclic ring comprises 1-4 heteroatoms. Within certain embodiments, each heterocyclic ring has 1 or 2 heteroatoms per ring. Each heterocyclic ring generally contains from 3 to 8 ring members, and heterocycles comprising fused, pendant or spiro rings typically contain from 9 to 14 ring members comprising carbon atoms and one, two, or three heteroatoms selected from nitrogen, oxygen, and sulfur. Therefore, examples of "heterocycle" or "heterocycloalkyl" groups include piperazine, piperidine, morpholine, thiomorpholine, pyrrolidine, imidazolidine, and thiazolide.

The term "substituent" as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member. Most typically, the substituent will replace a hydrogen.

The term "optionally substituted" means that a group may be substituted at one or more substitutable positions with one or more substituent. For example, suitable optional substituents include alkyl (preferably lower alkyl), alkoxy (preferably lower alkoxy), nitro, monoalkylamino (preferably with one to six carbons), dialkylamino (preferably with one to six carbons), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy and lower alkyl), alkoxycarbonyl (preferably a lower alkoxycarbonyl), alkylcarbonyloxy (preferably a lower alkylcarbonyloxy), and aryl (preferably phenyl), the aryl being optionally substituted by halo, lower alkyl and lower alkoxy groups. Optional substitution is also indicated by the phrase "substituted with from 0 to X substituents," where X is the maximum number of possible substituents. Certain optionally substituted groups are substituted with from 0 to 2, 3 or 4 independently selected substituents.

A dash ("—") that is not between two letters or symbols is used to indicate a point of t attachment for a substituent. For example, —CONH2 is attached through the carbon atom. A dashed cycle that locates inside of a heterocyle ring is used to indicate a conjugated system. The bonds between two atoms may be single bond or double bond.

The term "kinase" refers to any enzyme that catalyzes the addition of phosphate groups to a protein residue; for example, serine and threonine kinases catalyze the addition of phosphate groups to serine and threonine residues.

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., reduction of tumor cell growth, induction of apoptosis, reduction of metastasis, etc.

The terms "administration of a compound" or "administering a compound" refer to the act of providing a compound according to the inventive subject matter or pharmaceutical composition to the subject in need of treatment.

The term "protected" refers that the group is in modified form to preclude undesired side reactions at the protected site. Suitable protecting groups for the compounds of the present inventive subject matter will be recognized from the present application taking into account the level of skill in the art, and with reference to standard textbooks, such as Greene, T. W. et al., Protective Groups in Organic Synthesis, John Wiley & Sons, New York (1999).

The term "pharmaceutically acceptable" refers to the fact that the carrier, diluent or excipient must be compatible with the other ingredients of the formulation and not deleterious to the recipient thereof.

The term "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC— $(CH_2)_n$—COOH where n is 0-4, and the like. Similarly, pharmaceutically acceptable cations include sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of non-aqueous media, such as ether, ethyl acetate, ethanol, isopropanol or acetonitrile, is preferred. It will be apparent that each compound of Formula I may, but need not, be formulated as a hydrate, solvate or non-covalent complex. In addition, the various crystal forms and polymorphs are within the scope of the present inventive subject matter. Also provided herein are prodrugs of the compounds of Formula I. Therefore, the compound described herein can be the compound of Formula I, a pharmaceutically-acceptable salt thereof, a hydrate thereof, a solvate thereof, a tautomer thereof, an optical isomer thereof, E-isomer thereof, Z-isomer thereof, or a combination thereof.

In one embodiment is provided a compound of Formula Ia or a pharmaceutically acceptable salt thereof:

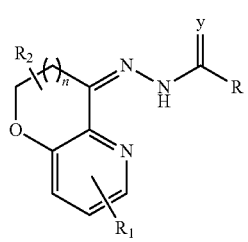

(Ia)

wherein Y is O, S and $NR_8$, and n is an integer between 0-2, inclusive. $R_1$ is hydrogen, F, Cl, Br, I, CN, $C_1$-$C_4$ alkyl, $C_1$-$C_6$ alkoxy, $C_2$-$C_6$ alkenyl, $CF_3$, $CHF_2$, $CH_2F$, $C_2$-$C_6$ alkynyl, or $CON(R_5)R_6$. $R_2$ is hydrogen, alkyl, cycloalkyl, alkenyl, alkynyl, alkylthio, aryl, arylalkyl, or oxo. R is (i), or (ii), or (iii), wherein (i) is heteroaryl or aryl, each of which is substituted with from 0 to 4 substituents independently selected from the group consisting of halogen, hydroxy, cyano, $CF_3$, $CHF_2$, $CH_2F$, —COOH, —$SO_2NH_2$, oxo, nitro, $C_1$-$C_4$ alkyl, $C_1$-$C_6$ alkoxy, $C_2$-$C_6$ alkenyl, $C_2$-$C_6$ alkynyl, $CON(R_5)R_6$, $SO_2N(R_5)R_6$, and $N(R_7)R_8$, wherein (ii) is $C_1$-$C_4$ alkyl, $C_1$-$C_6$ alkoxy, $C_2$-$C_6$ alkenyl, $C_2$-$C_6$ alkynyl, $CON(R_5)R_6$ or N(R7)R8, and wherein (iii) is a group having the formula (A):

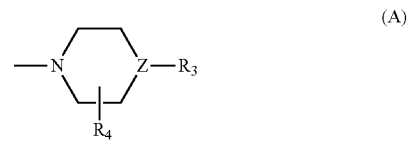

(A)

wherein $R_4$ is hydrogen, $C_1$-$C_4$ alkyl, or oxo; Z is CH, when $R_3$ is hydrogen; or Z—$R_3$ is O; or Z is N, $R_3$ is hydrogen, $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$cycloalkyl)$C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- or di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- or di-($C_1$-$C_6$ alkyl) sulfonamido, or mono- or di-($C_1$-$C_6$ alkyl)aminocarbonyl, each of which is substituted with from 0 to 4 substituents independently chosen from halogen, hydroxy, cyano, amino, —COOH, nitro, $CF_3$, and oxo. $R_5$ and $R_6$ are independently selected from hydrogen, $C_1$-$C_4$ alkyl, cycloalkyl, alkenyl, and alkynyl. $R_7$ and $R_8$ are independently selected from hydrogen, $C_1$-$C_4$ alkyl, $C_2$-$C_6$ alkenyl, $C_2$-$C_6$ alkynyl, $C_3$-$C_{10}$ aryl or heteroaryl, $C_1$-$C_6$ alkoxycarbonyl, and $C_2$-$C_6$ alkanoyloxy, each of which is substituted with from 0 to 4 substituents independently chosen from halogen, hydroxy, cyano, amino, —COOH, nitro, $CF_3$ and oxo.

In another embodiment is provided a compound of Formula Ib or a pharmaceutically acceptable salt thereof:

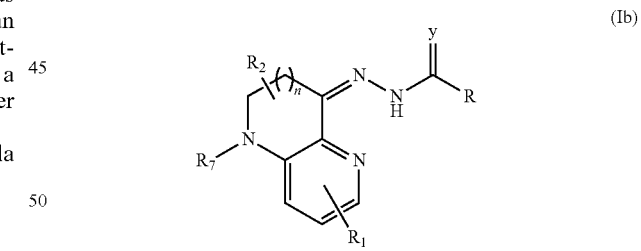

(Ib)

wherein Y is O, S and $NR_8$, and n is an integer between 0-2, inclusive. $R_1$ is hydrogen, F, Cl, Br, I, CN, $C_1$-$C_4$ alkyl, $C_1$-$C_6$ alkoxy, $C_2$-$C_6$ alkenyl, $CF_3$, $CHF_2$, $CH_2F$, $C_2$-$C_6$ alkynyl, or $CON(R_5)R_6$. $R_2$ is hydrogen, alkyl, cycloalkyl, alkenyl, alkynyl, alkylthio, aryl, arylalkyl, or oxo. R is (i), or (ii), or (iii), wherein (i) is heteroaryl or aryl, each of which is substituted with from 0 to 4 substituents independently selected from the group consisting of halogen, hydroxy, cyano, $CF_3$, $CHF_2$, $CH_2F$, —COOH, —$SO_2NH_2$, oxo, nitro, $C_1$-$C_4$ alkyl, $C_1$-$C_6$ alkoxy, $C_2$-$C_6$ alkenyl, $C_2$-$C_6$ alkynyl, $CON(R_5)R_6$, $SO_2N(R_5)R_6$, and $N(R_7)R_8$, wherein (ii) is $C_1$-$C_4$ alkyl, $C_1$-$C_6$ alkoxy, $C_2$-$C_6$ alkenyl, $C_2$-$C_6$ alkynyl, $CON(R_5)R_6$ or N(R7)R8, and wherein (iii) is a group having the formula (A):

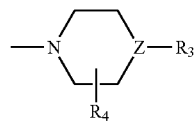

(A)

wherein $R_4$ is hydrogen, $C_1$-$C_4$ alkyl, or oxo; Z is CH, when $R_3$ is hydrogen; or Z—$R_3$ is O; or Z is N, $R_3$ is hydrogen, $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$cycloalkyl)$C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- or di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- or di-($C_1$-$C_6$ alkyl) sulfonamido, or mono- or di-($C_1$-$C_6$ alkyl)aminocarbonyl, each of which is substituted with from 0 to 4 substituents independently chosen from halogen, hydroxy, cyano, amino, —COOH, nitro, $CF_3$, and oxo. $R_5$ and $R_6$ are independently selected from hydrogen, $C_1$-$C_4$ alkyl, cycloalkyl, alkenyl, and alkynyl. $R_7$ and $R_8$ are independently selected from hydrogen, $C_1$-$C_4$ alkyl, $C_2$-$C_6$ alkenyl, $C_2$-$C_6$ alkynyl, $C_3$-$C_{10}$ aryl or heteroaryl, $C_1$-$C_6$ alkoxycarbonyl, and $C_2$-$C_6$ alkanoyloxy, each of which is substituted with from 0 to 4 substituents independently chosen from halogen, hydroxy, cyano, amino, —COOH, nitro, $CF_3$ and oxo.

In still other embodiments are provided compounds of Formula Ic-Ih, or a pharmaceutically acceptable salt thereof:

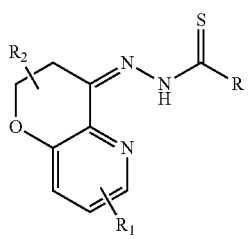

(Ic)

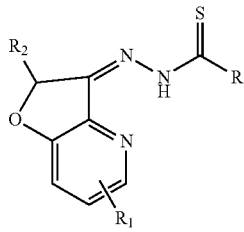

(Id)

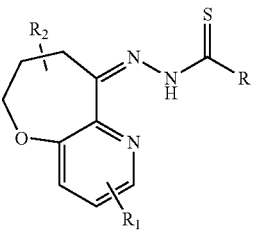

(Ie)

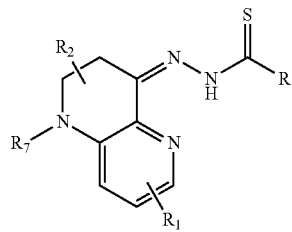

(If)

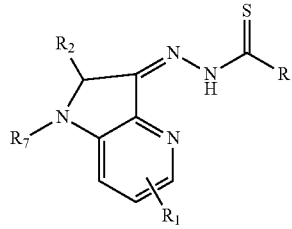

(Ig)

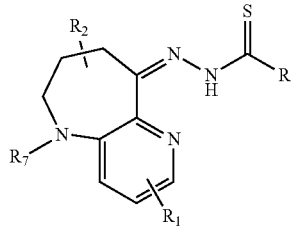

(Ih)

wherein $R_1$, $R_2$, $R_7$, and R for the compounds Ic-Ih are defined as for the compounds I, Ia, and Ib above.

Therefore, in certain embodiments of formula I, Y is O and X is O, or in certain embodiments of formula I, Y is O and X is NH, or in certain embodiments of formula I, Y is S, or in certain embodiments of formula I, Y is S and X is O, or in certain embodiments of formula I, Y is S and X is NH, or in certain embodiments of formula I, Y is S and X is NMe, or in certain embodiments of formula I, Y is NH and X is O, or in certain embodiments of formula I, Y is NH and X is NH, or in certain embodiments of formula I, Y is NH and X is NMe, and/or in certain embodiments of formula I $R_1$ is hydrogen, F, Cl, Br, —$CH_3$, or —$OCH_3$, and/or in certain embodiments of formula I $R_2$ is hydrogen, or $C_1$-$C_6$ alkyl.

In still further contemplated embodiments of formula I R is heteroaryl or aryl, each of which is substituted with from 0 to 4 substituents independently chosen from F, Cl hydroxy, cyano, $CF_3$, $CHF_2$, $CH_2F$, —COOH, —$SO_2NH_2$, oxo, nitro, $C_1$-$C_4$ alkyl, $C_1$-$C_6$ alkoxy, $C_2$-$C_6$ alkenyl, and $C_2$-$C_6$ alkynyl. In other embodiments, R is heteroaryl or aryl, each of which is substituted with CON($R_5$)$R_6$, $SO_2$N($R_5$)$R_6$ and N($R_7$)$R_8$, while in still other embodiments R is pyridine, which is substituted with N($R_7$)$R_8$ and $R_7$ and $R_5$ is a 5-6 member heterocycle. In addition, it is contemplated that in certain embodiments R is a group of the formula (A):

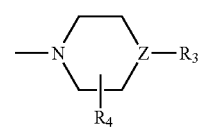

(A)

wherein $R_4$ is hydrogen or $C_1$-$C_4$ alkyl, Z is N, $R_3$ is hydrogen, $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$cycloalkyl)$C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- or di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- or di-($C_1$-$C_6$ alkyl) sulfonamido, or mono- or di-($C_1$-$C_6$ alkyl)aminocarbonyl, each of which is substituted with from 0 to 4 substituents independently chosen from halogen, hydroxy, cyano, amino, —COOH, nitro, $CF_3$ and oxo.

In further contemplated aspects, preferred R groups of formula (I) include

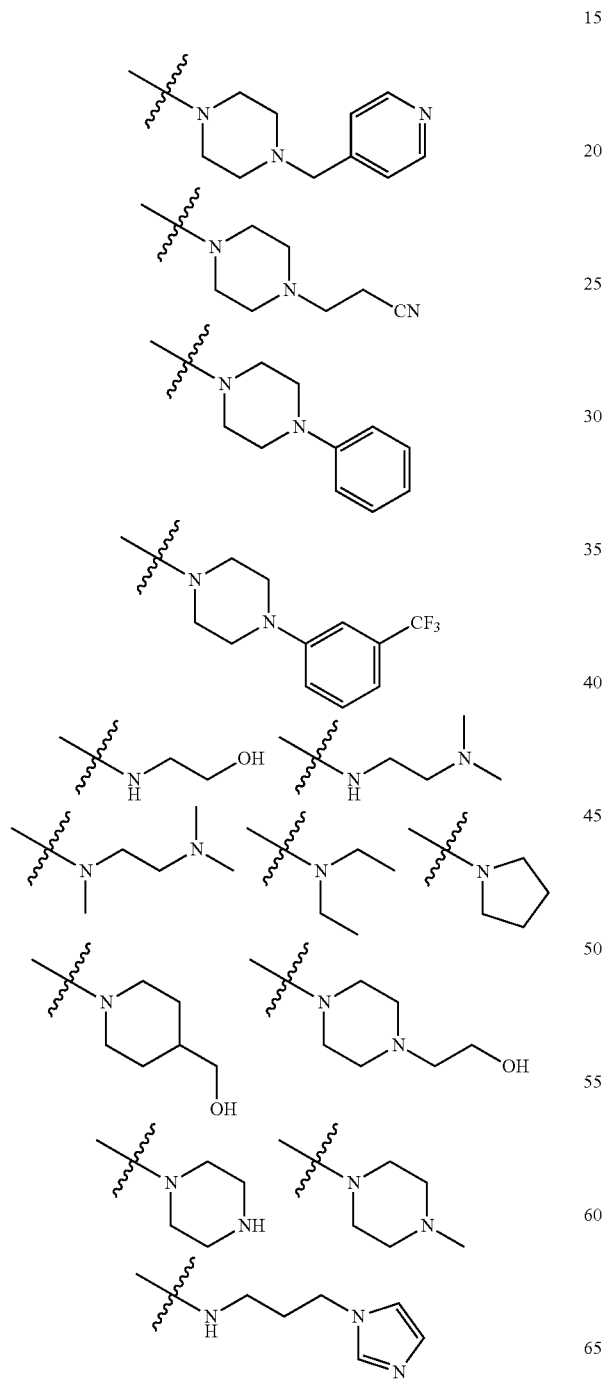

-continued

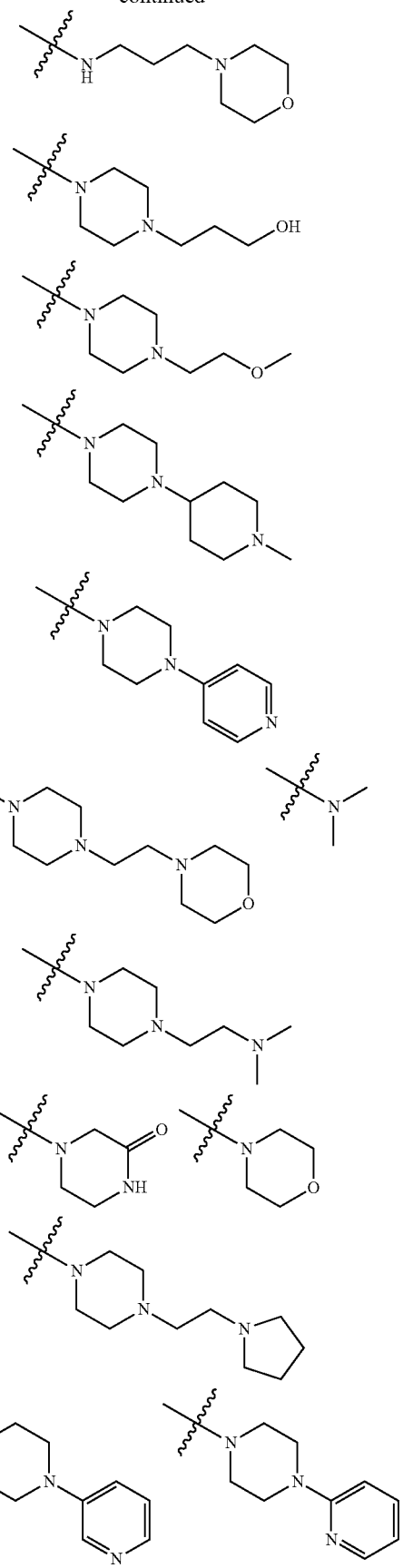

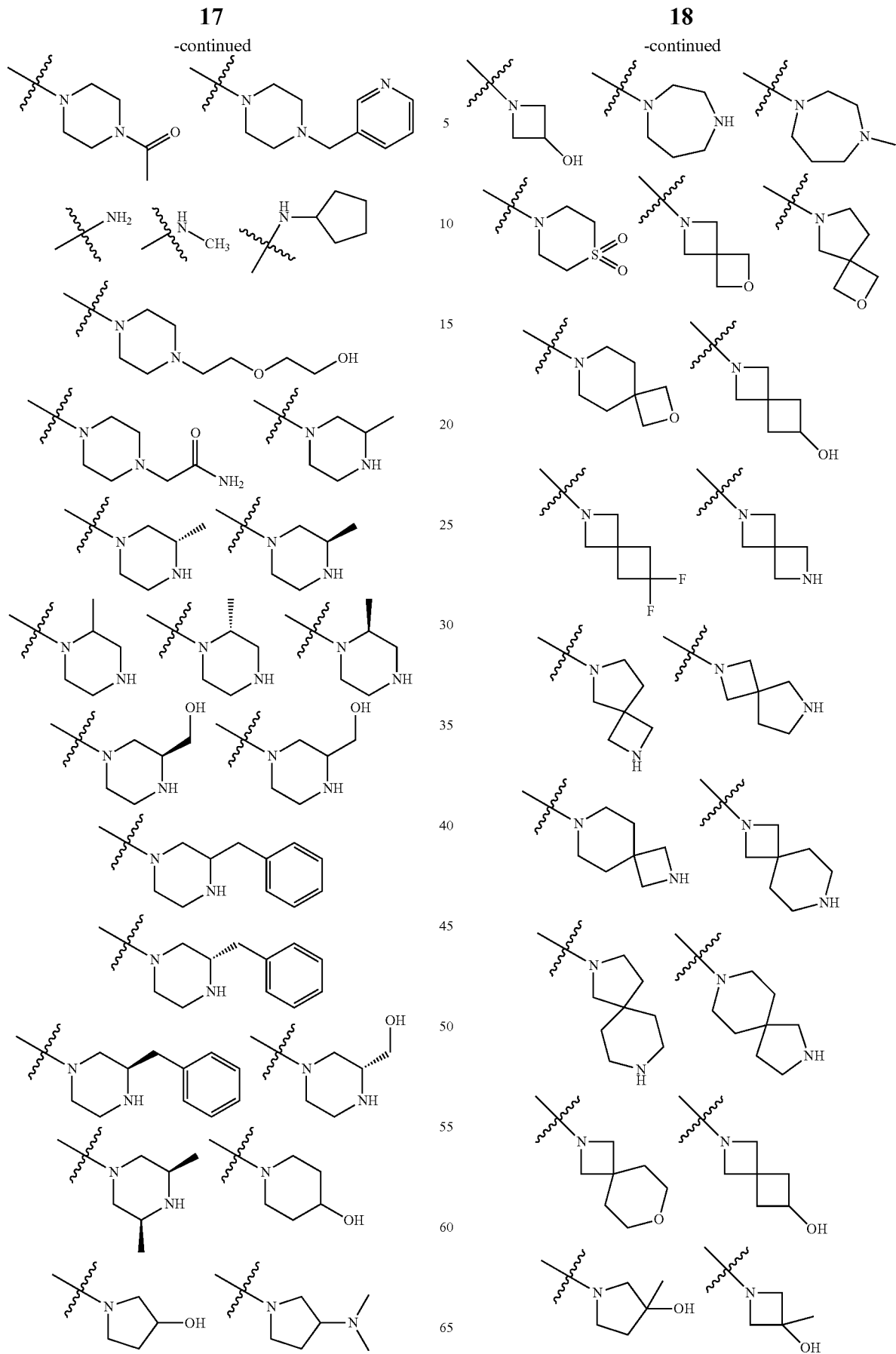

-continued
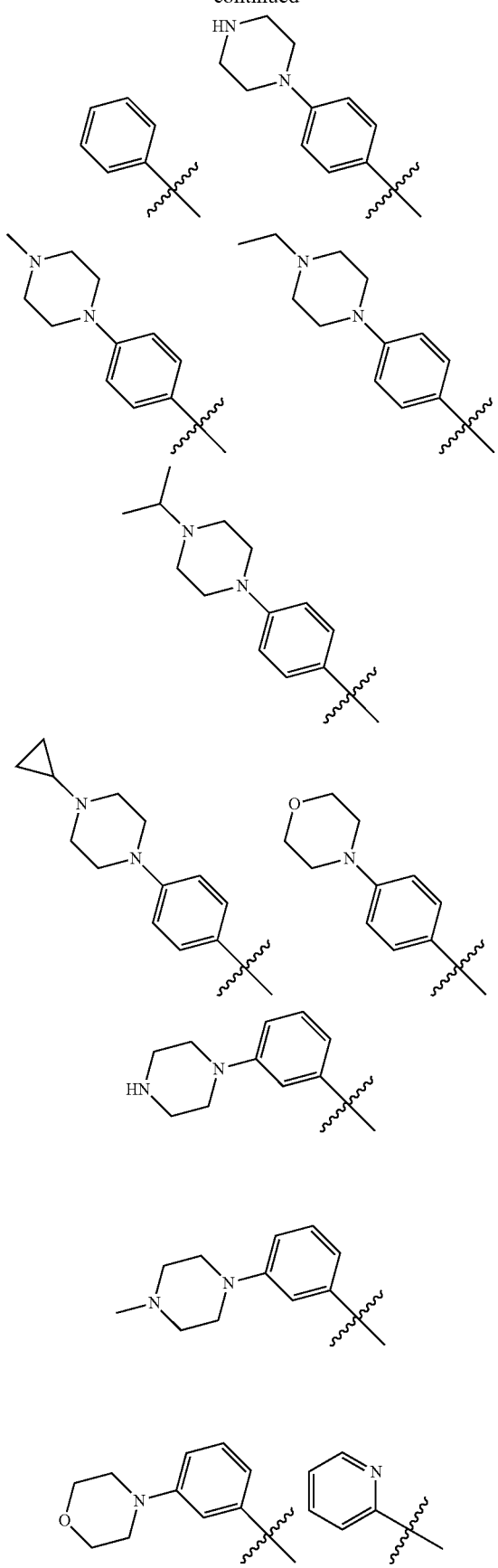
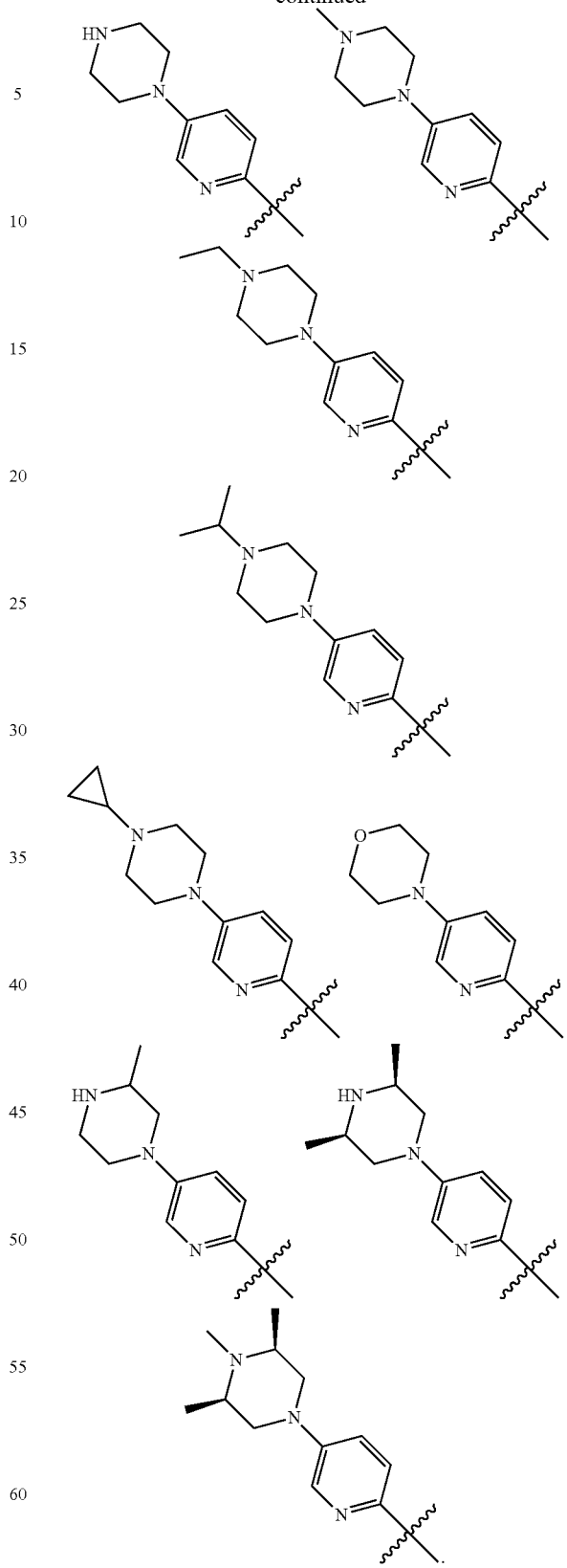
In further contemplated aspects, preferred $R_1$ groups of formula (I) include F, Cl, Br, CN, $CF_3$, $CF_2H$, $CFH_2$, $CH_3$ and $OCH_3$.

Therefore, and viewed from a different perspective, contemplated compounds include
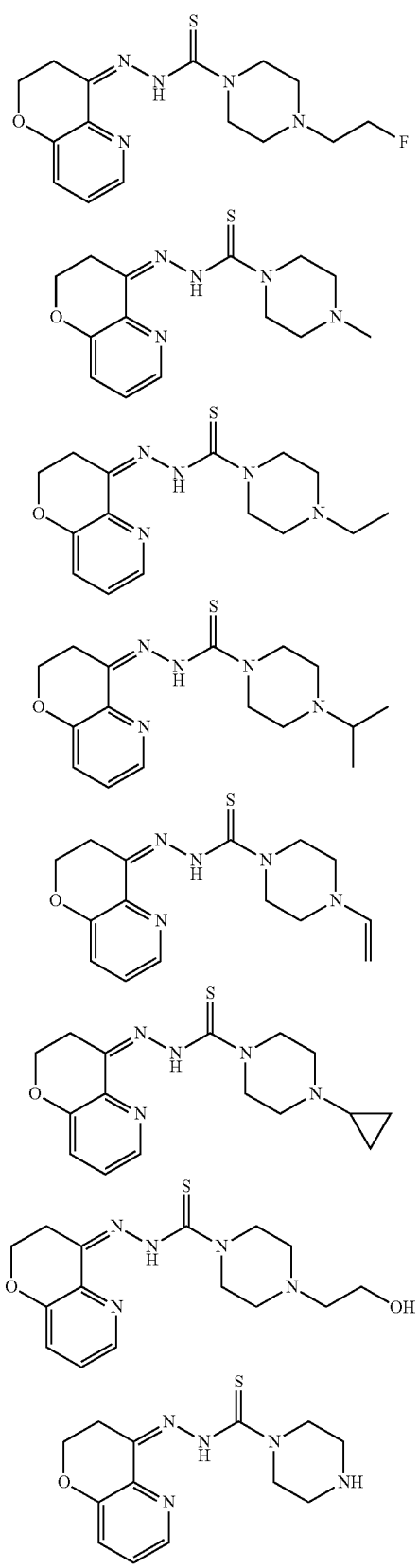
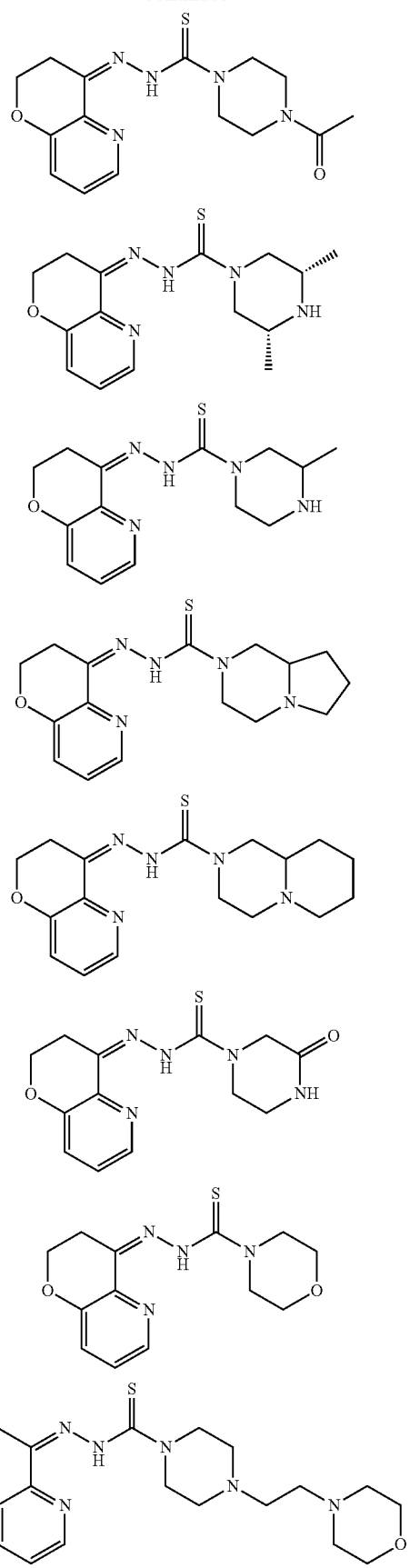

-continued
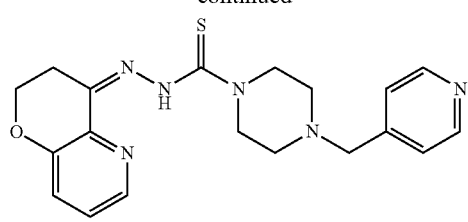
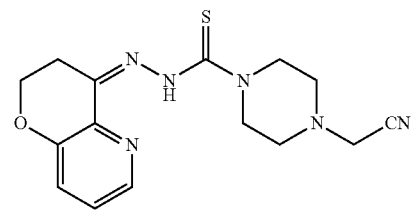
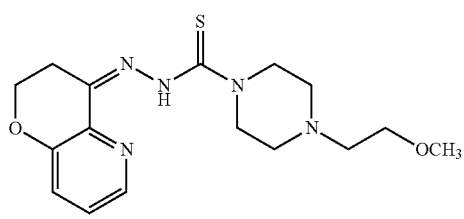
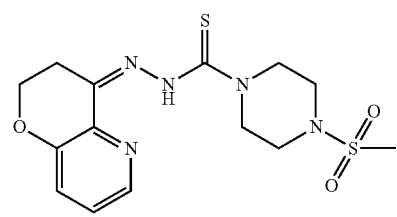
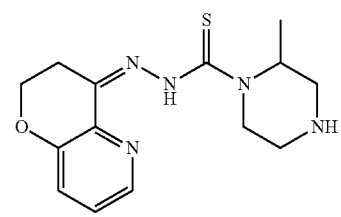
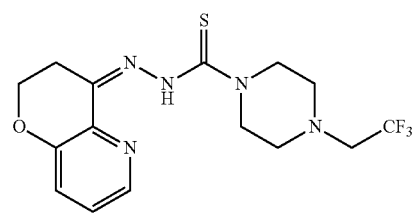
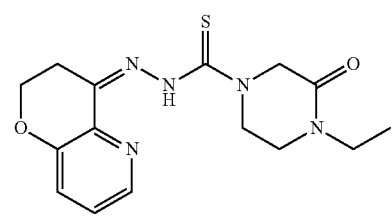
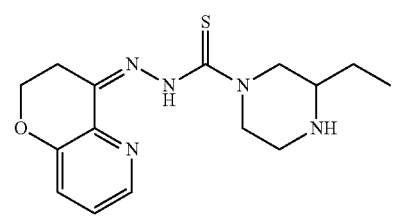
-continued
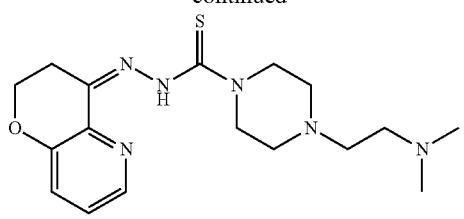
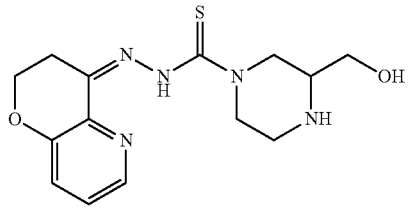
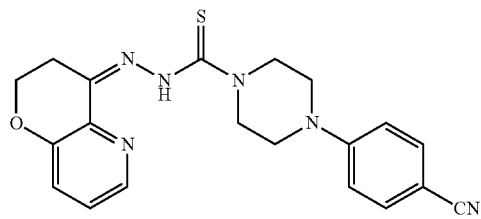
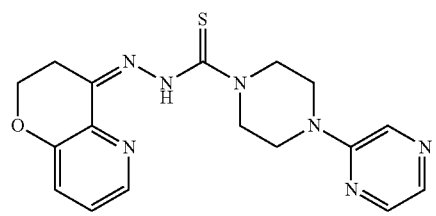
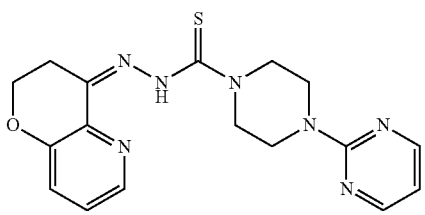
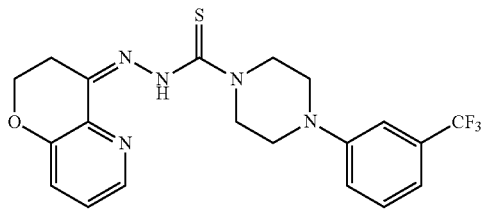
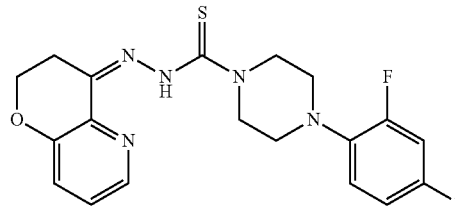
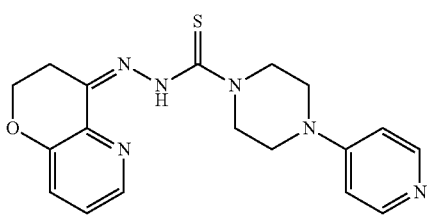

-continued
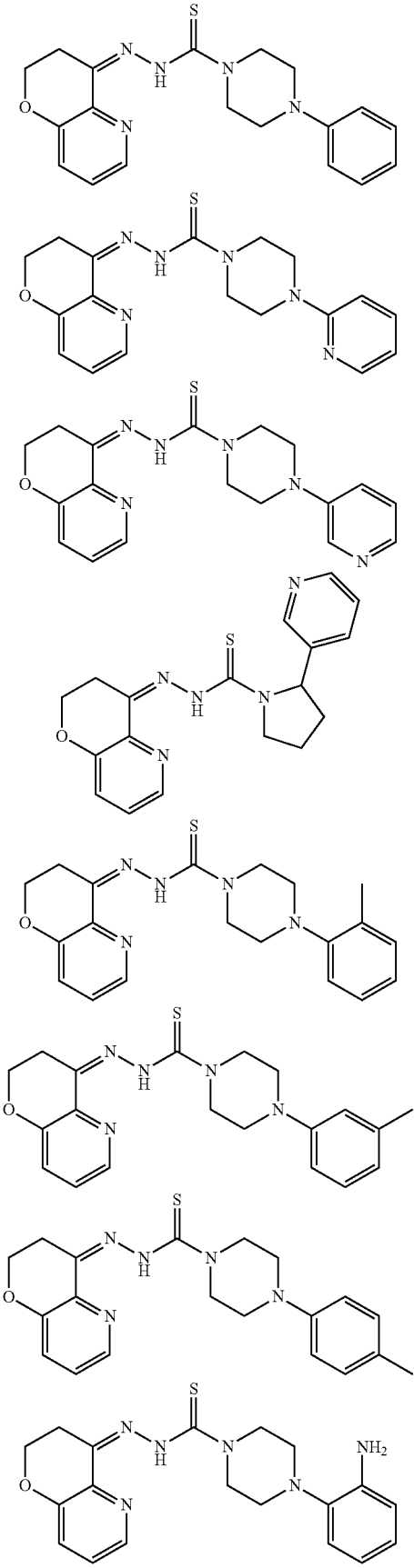
-continued
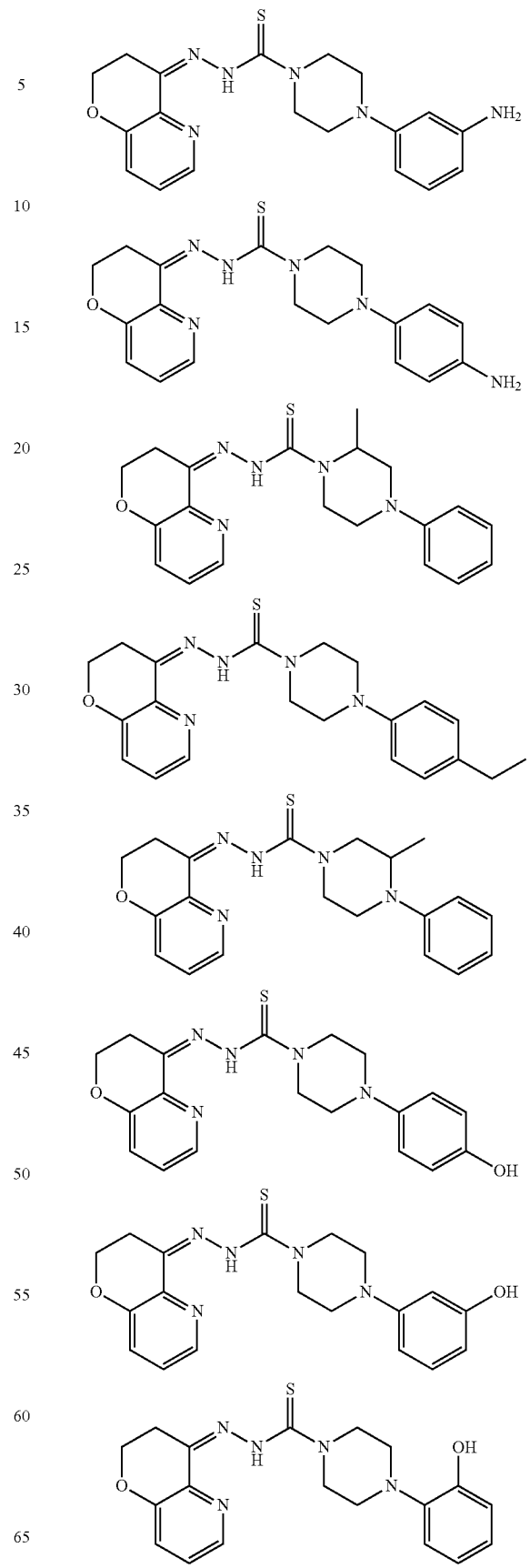

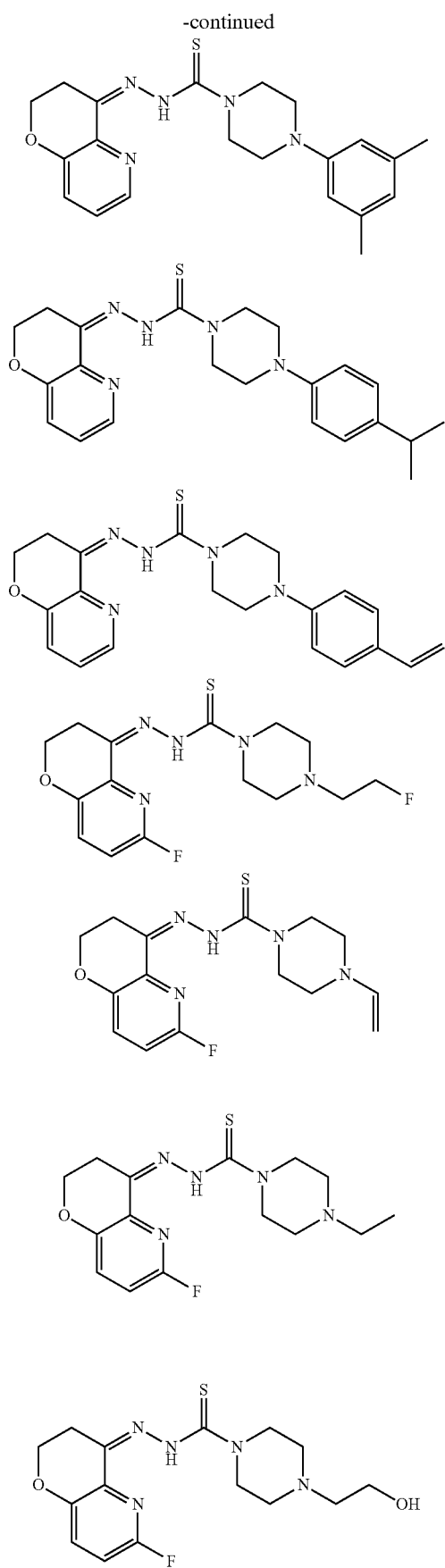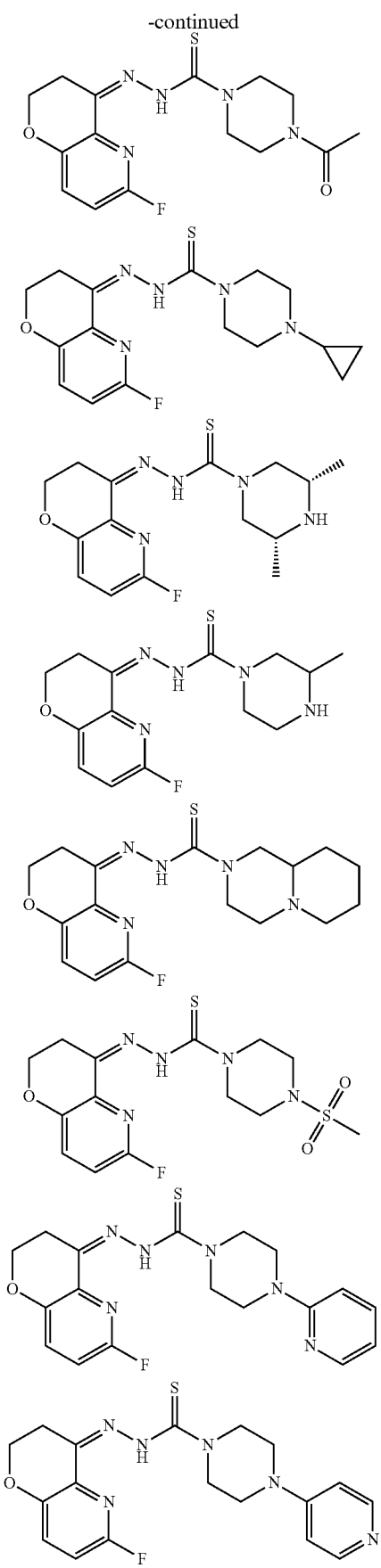

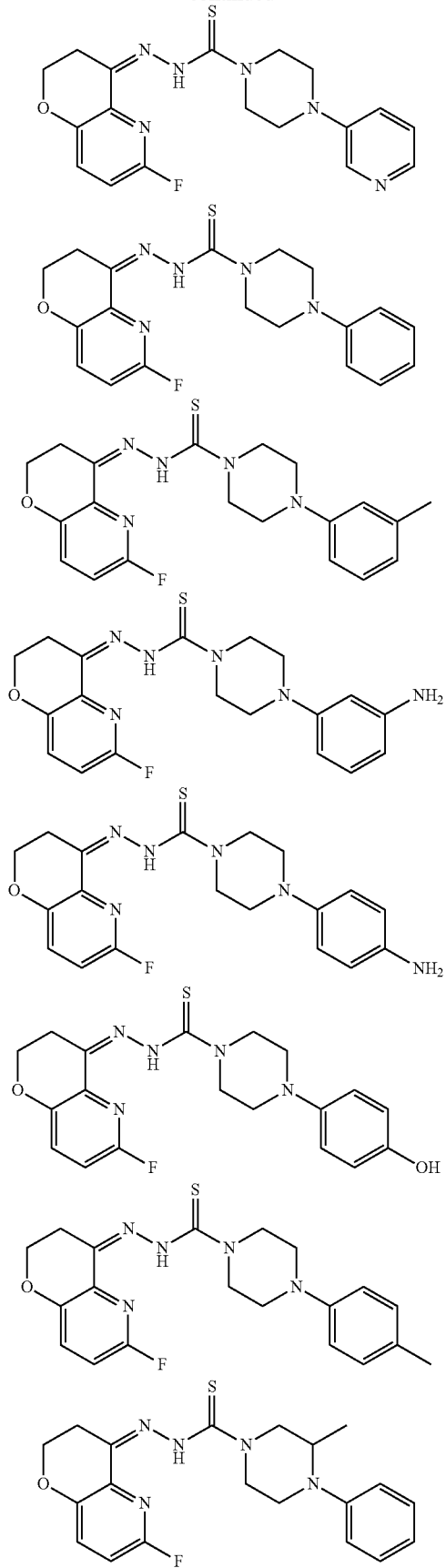
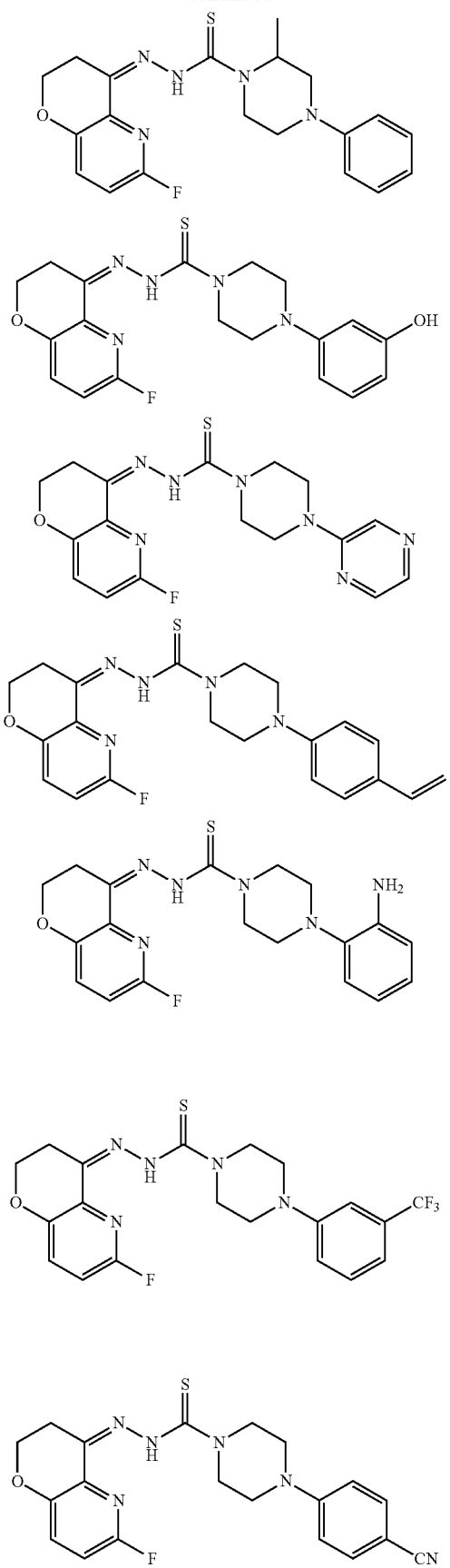

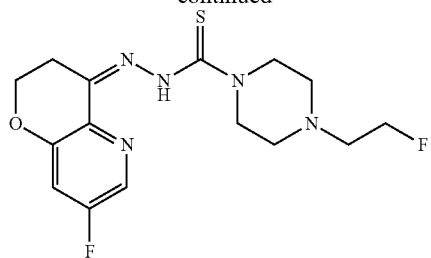
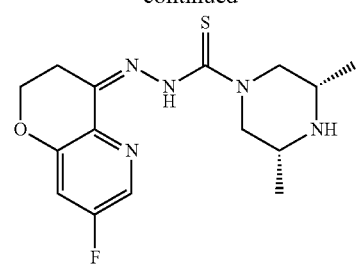
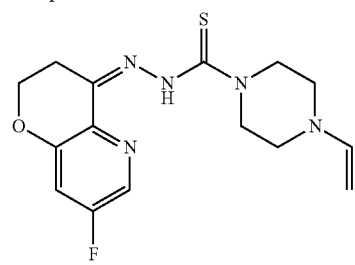
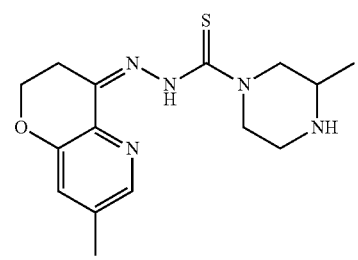
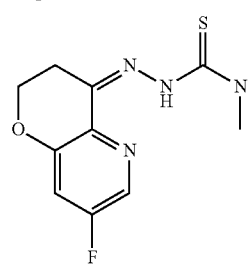
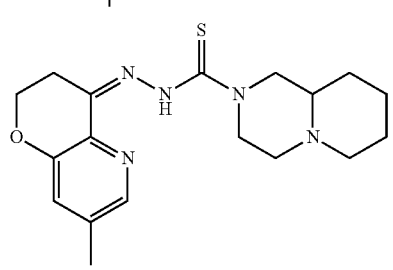
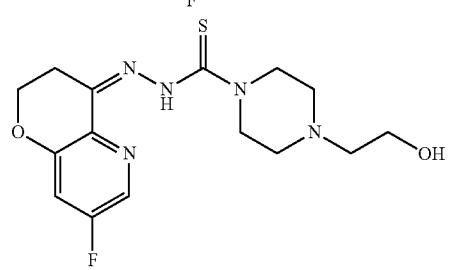
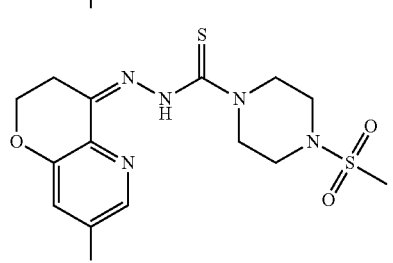
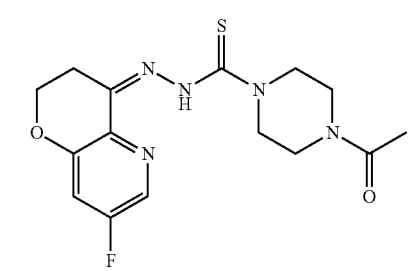
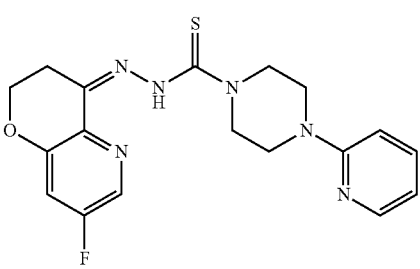
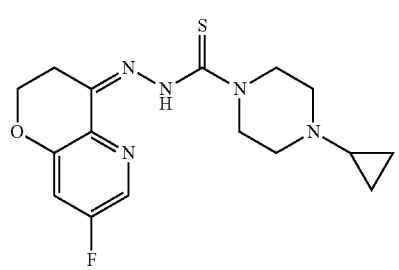
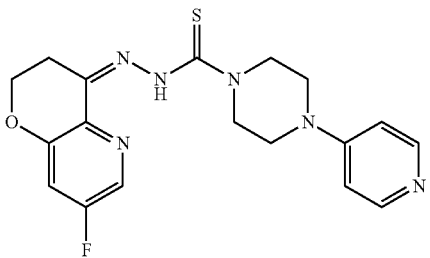

-continued
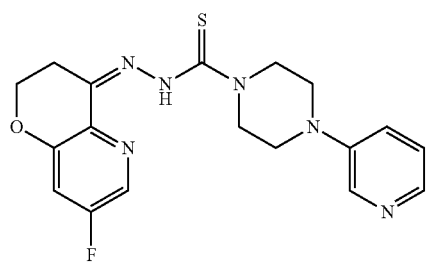
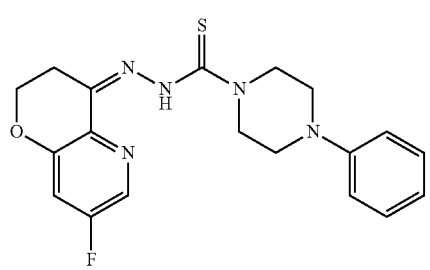
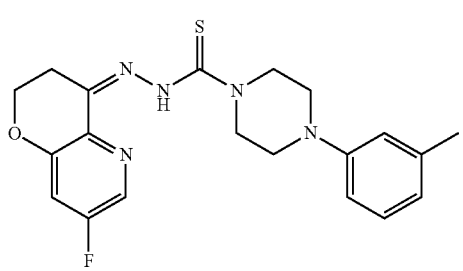
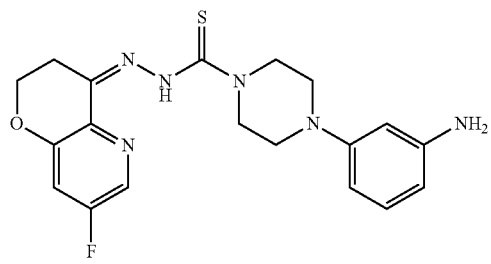
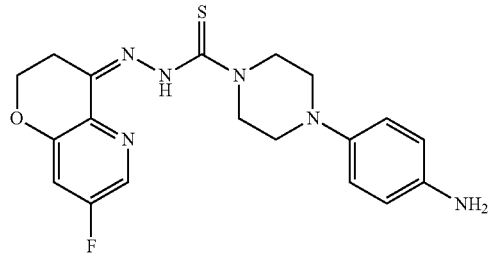
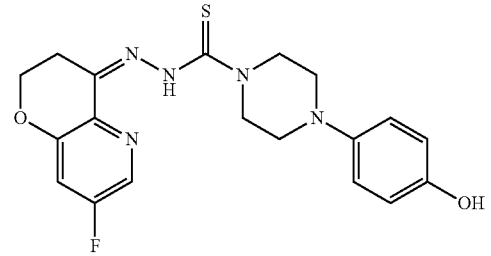
-continued
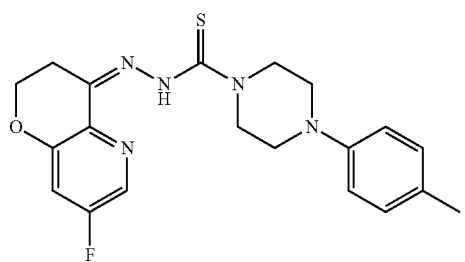
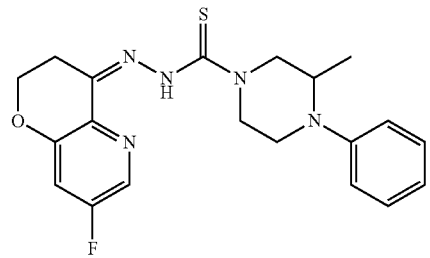
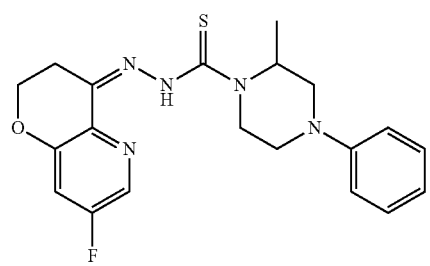
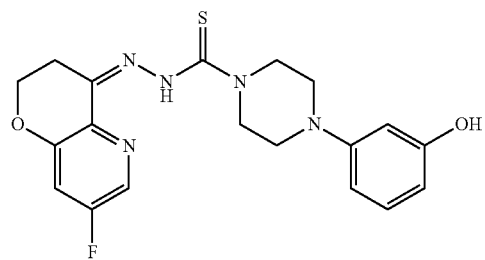
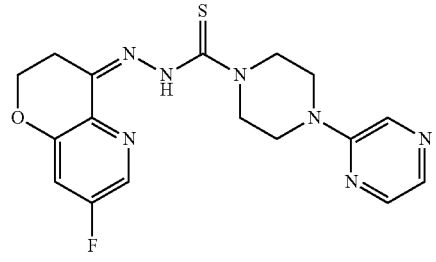
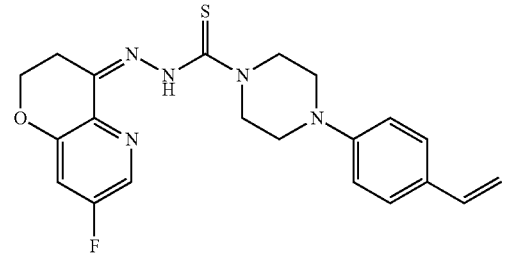

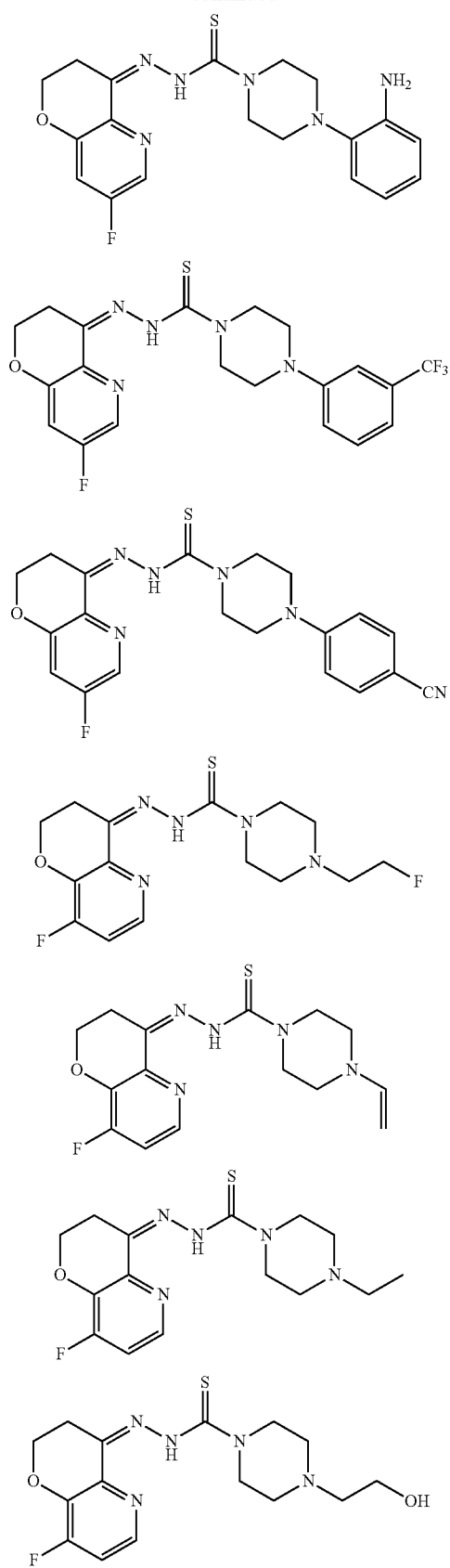
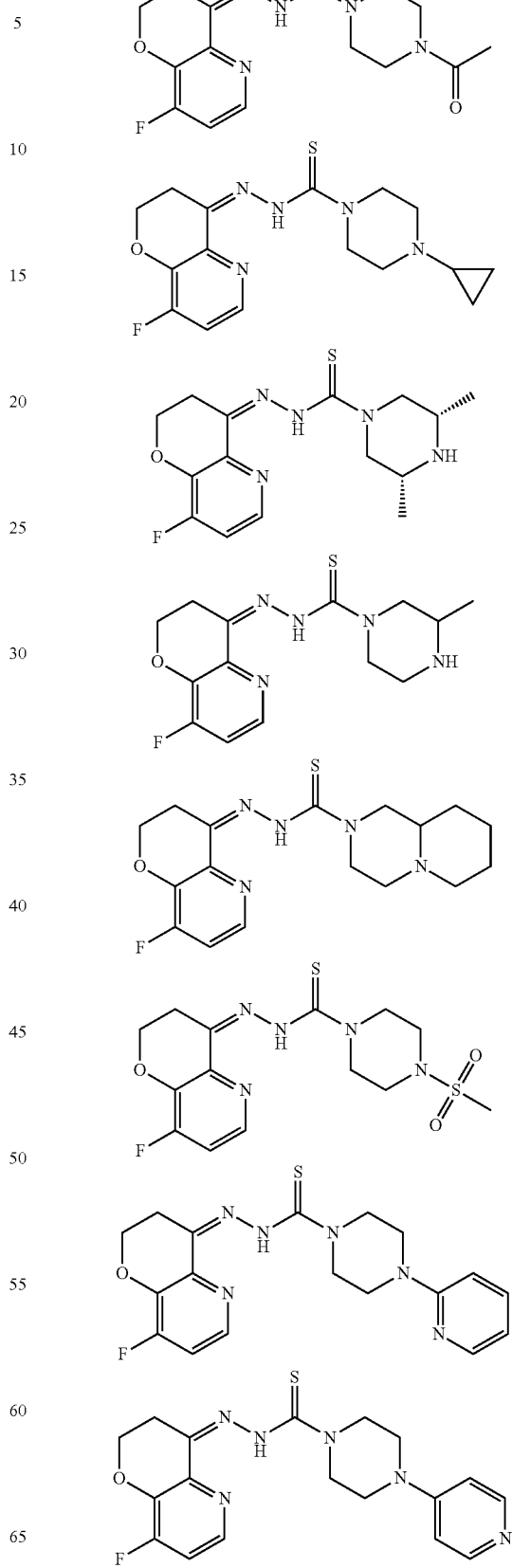

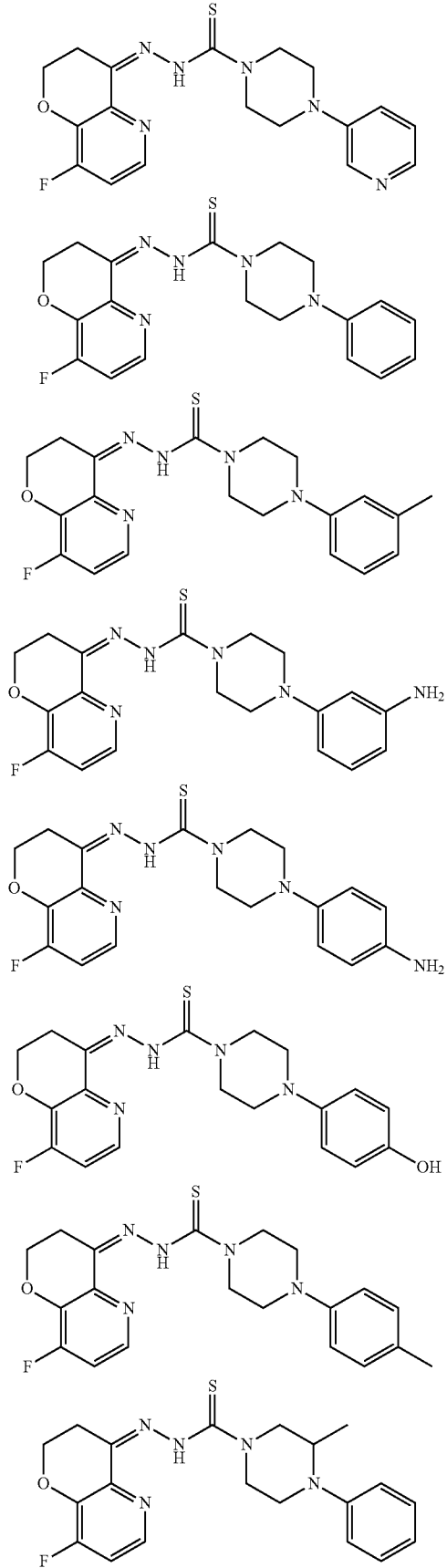
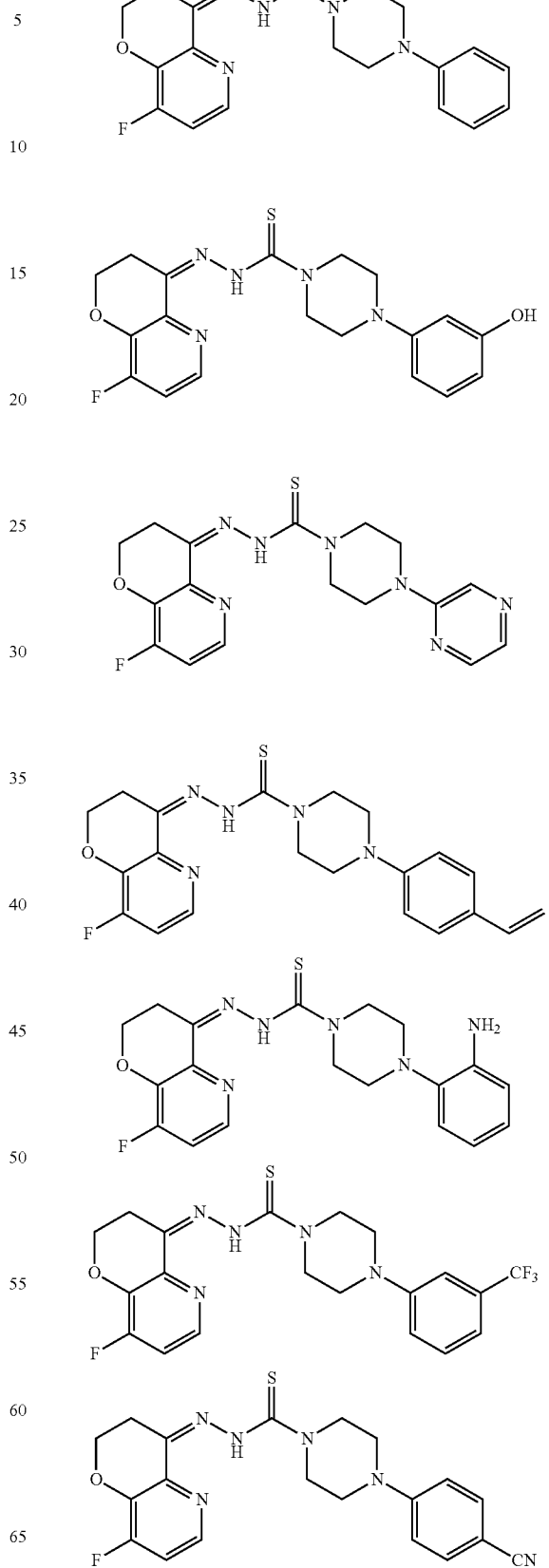

39
-continued
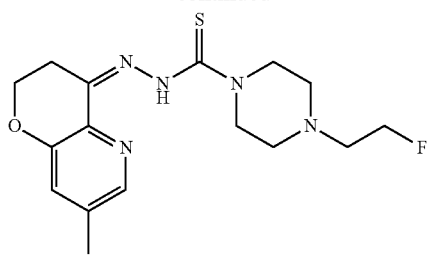
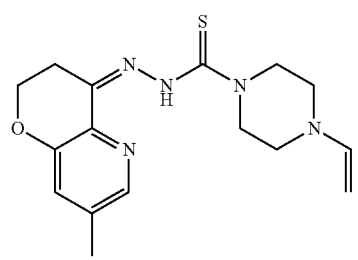
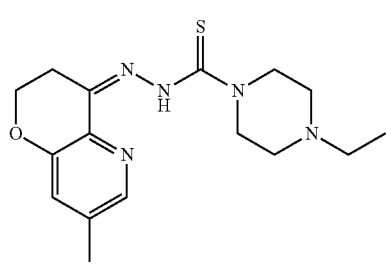
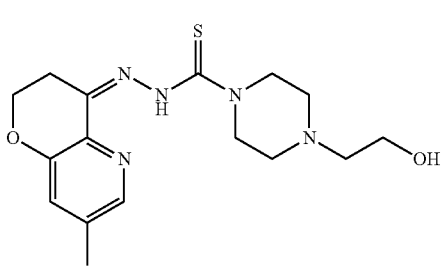
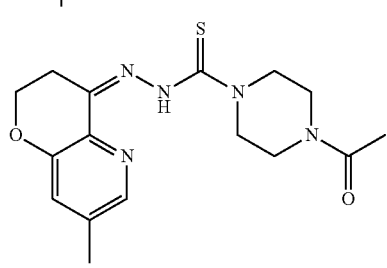
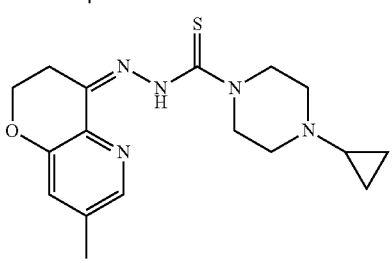
40
-continued
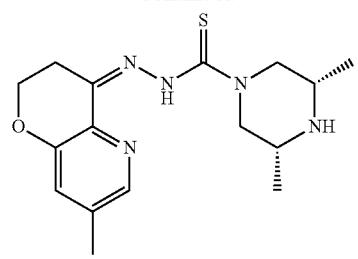
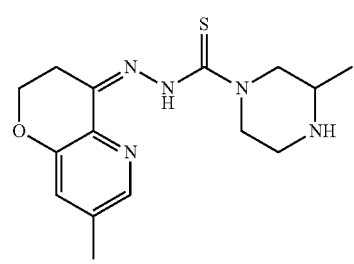
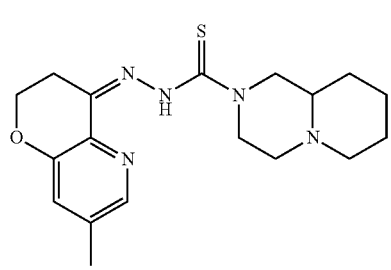
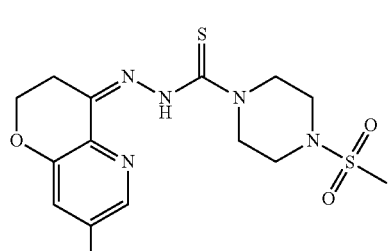
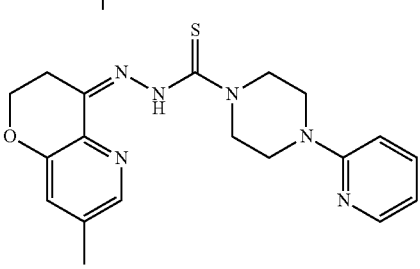
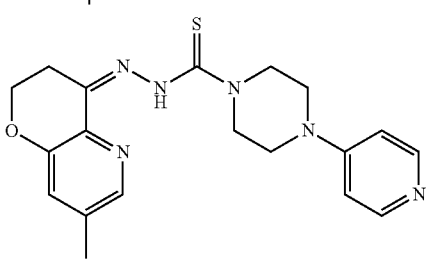

41
-continued
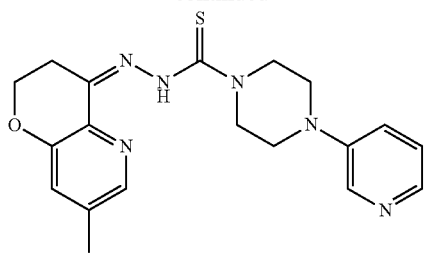
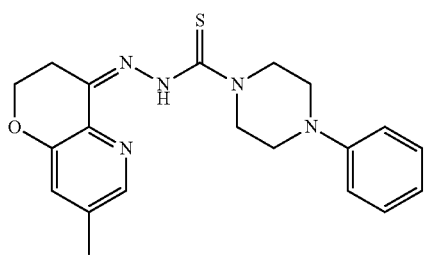
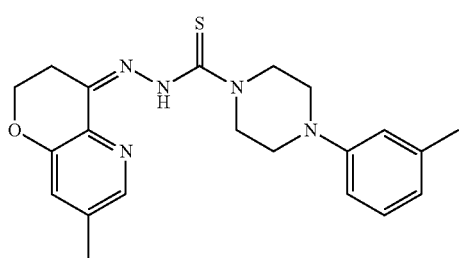
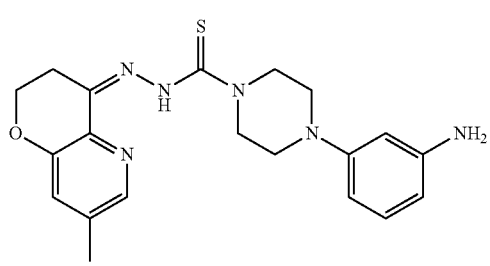
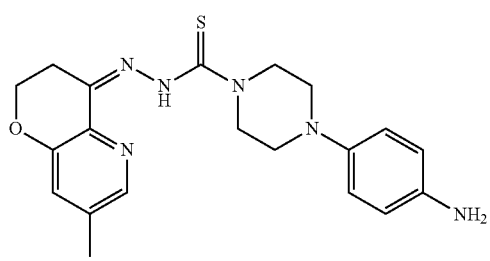
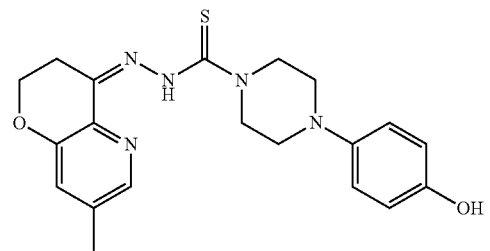
42
-continued
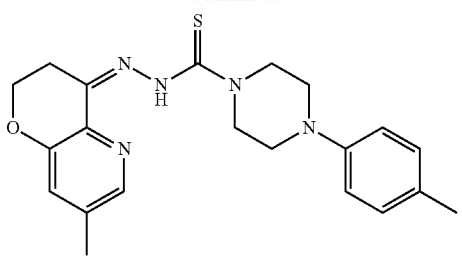
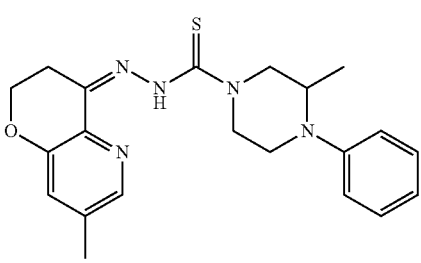
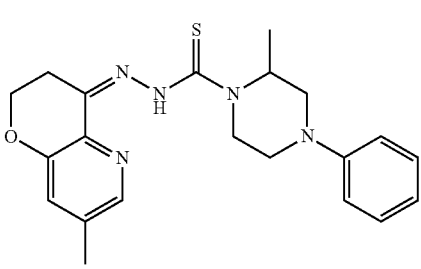
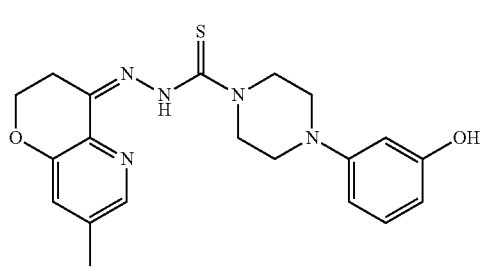
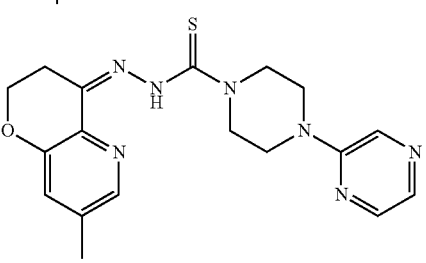
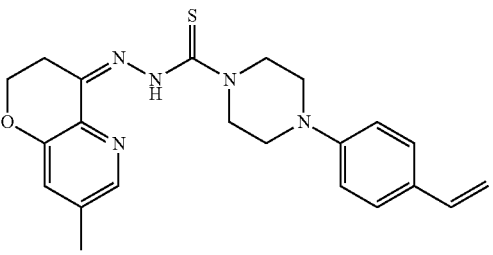

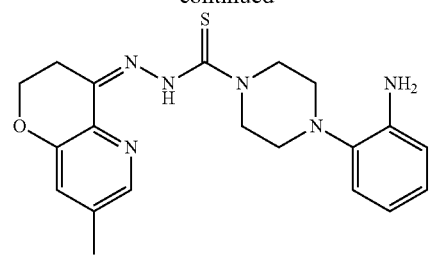
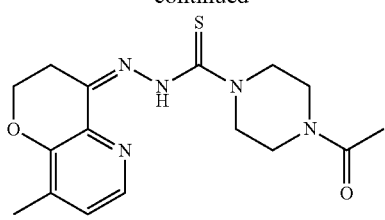
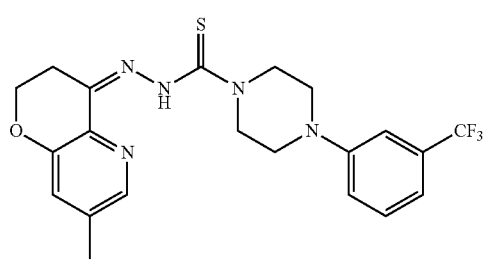
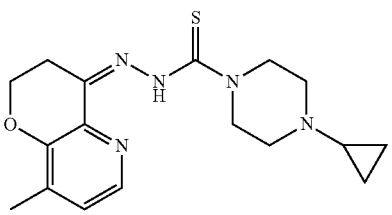
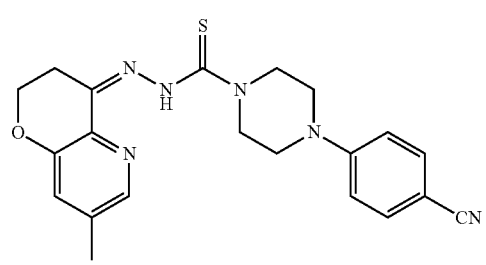
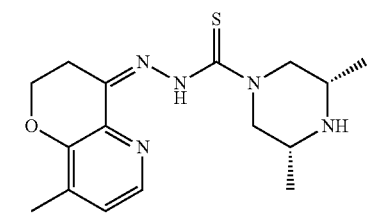
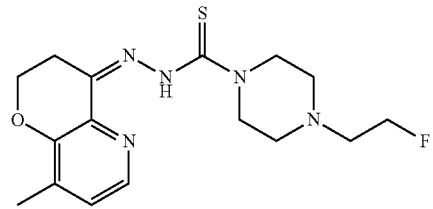
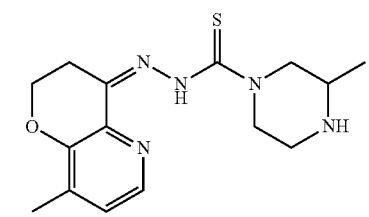
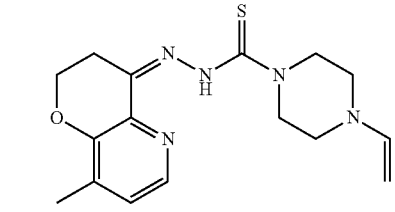
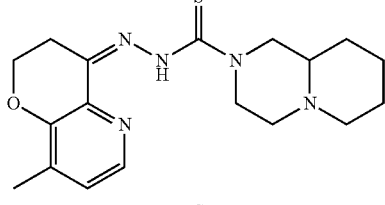
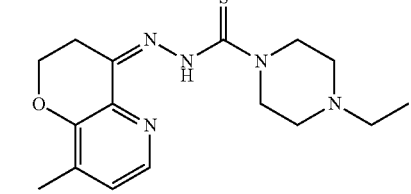
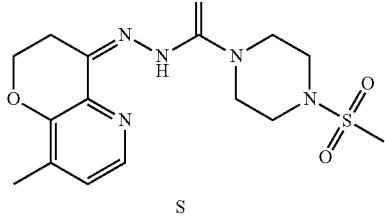
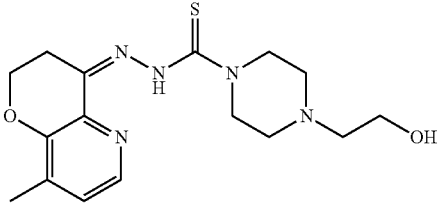
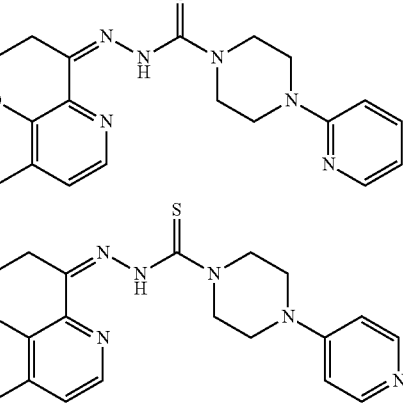

-continued

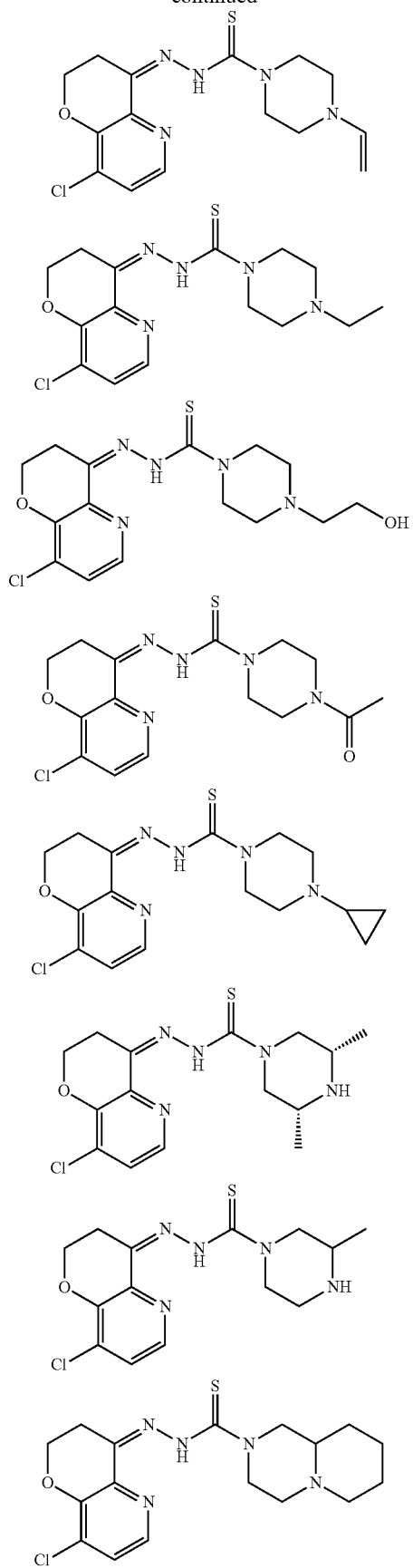
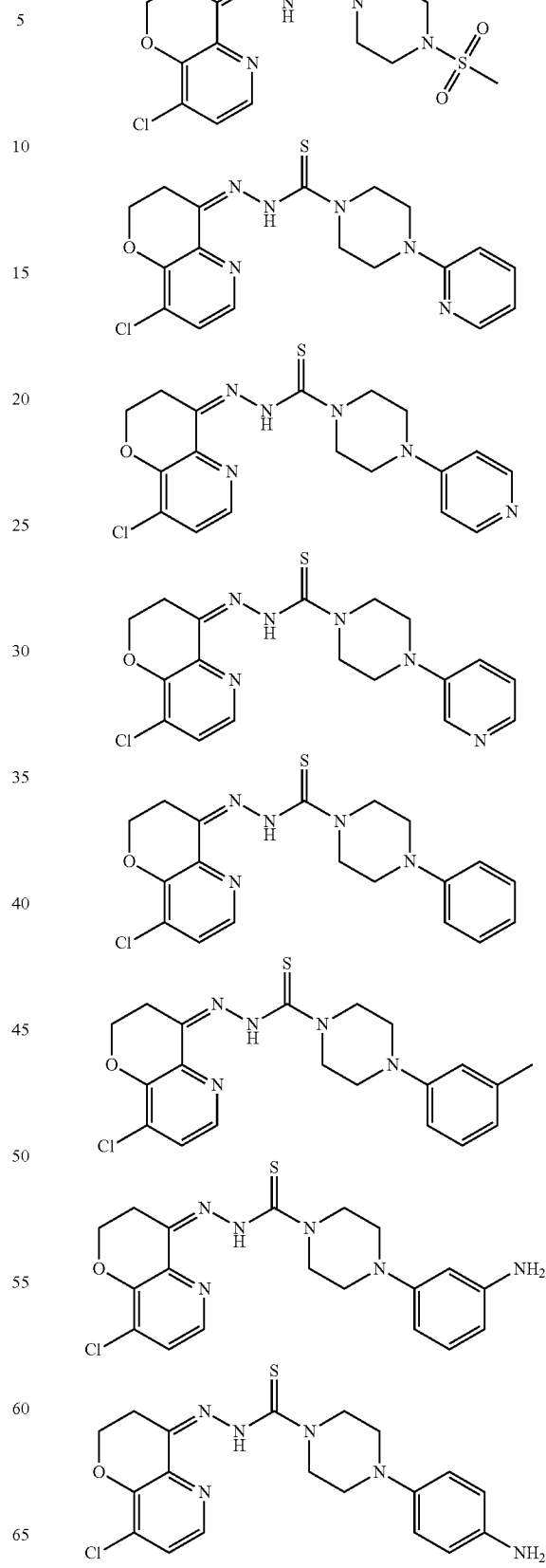

-continued
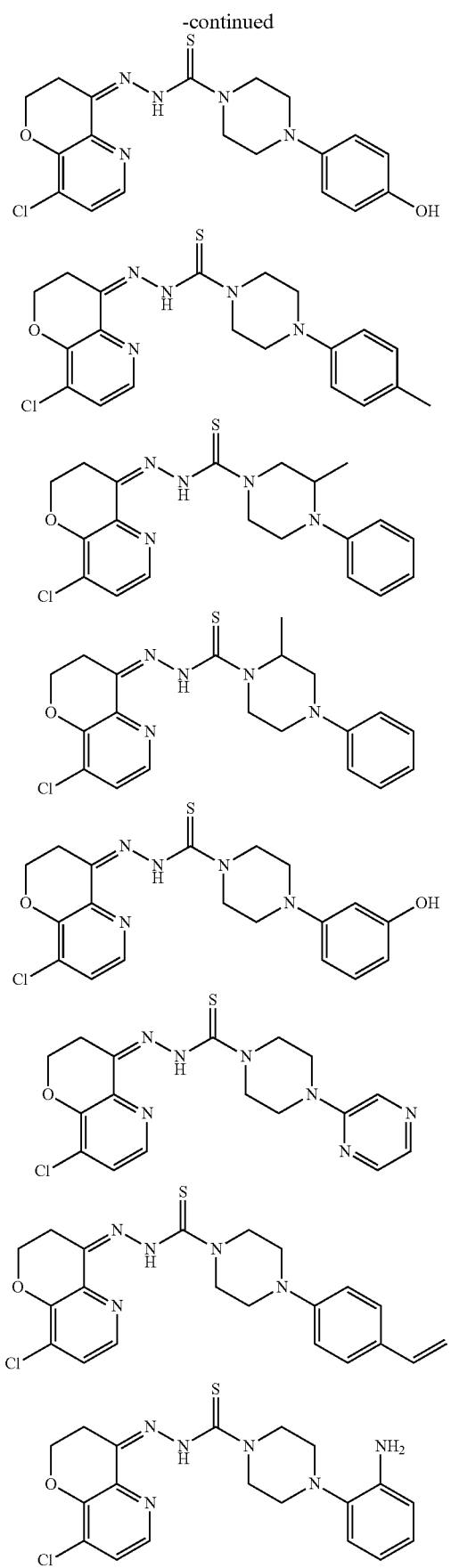
-continued
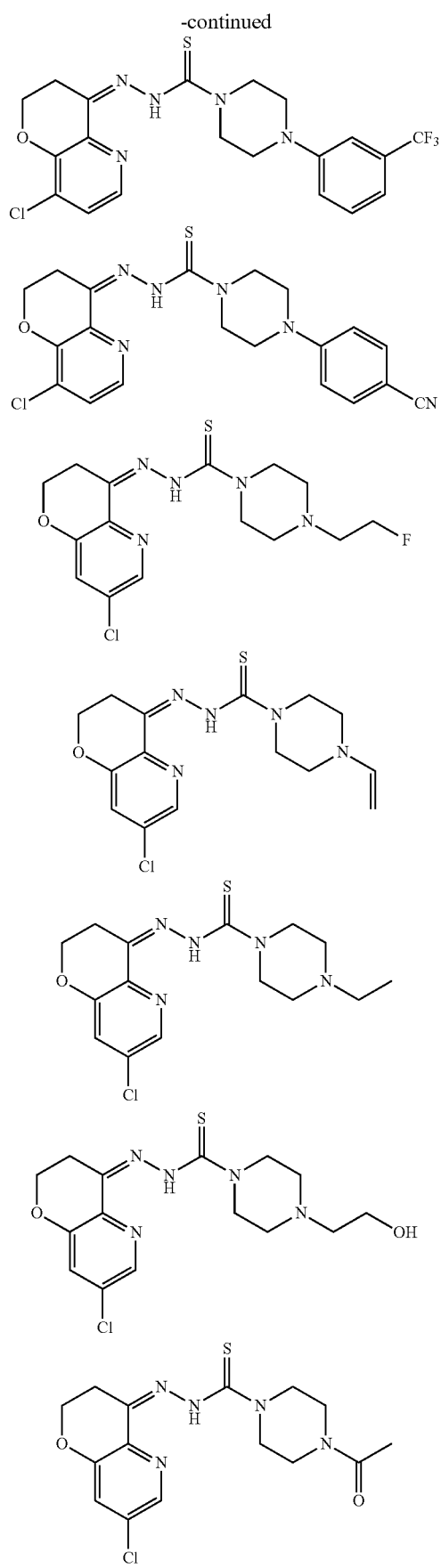

51
-continued
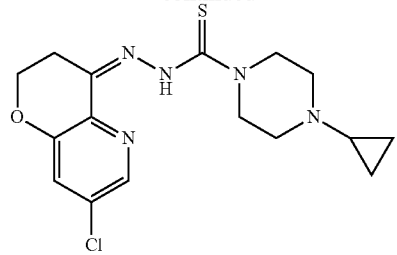
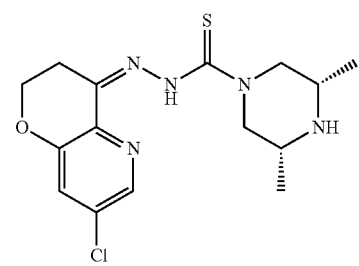
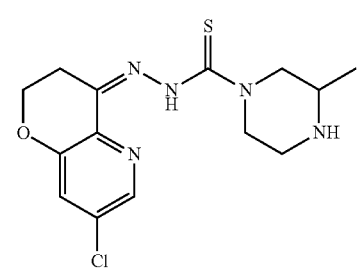
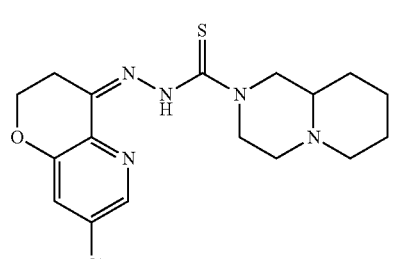
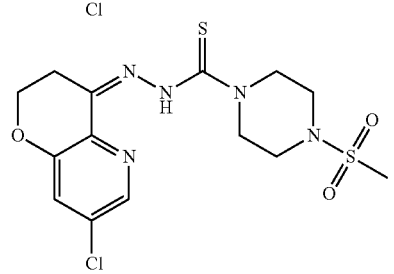
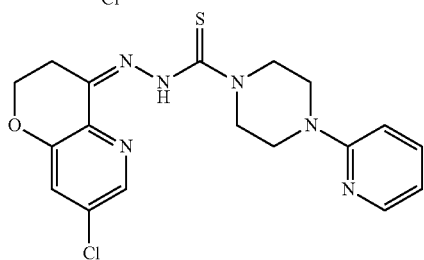
52
-continued
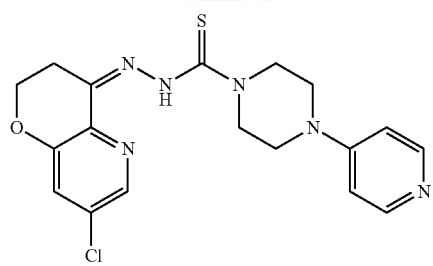
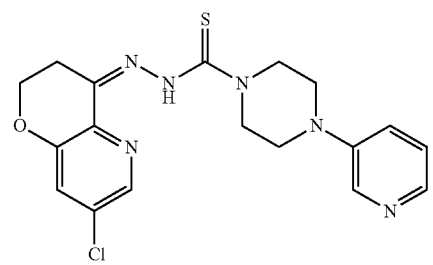
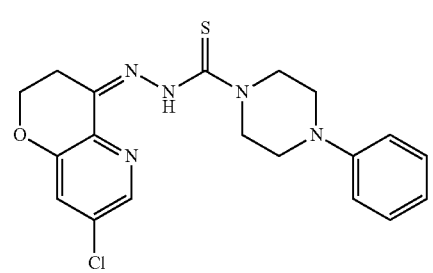
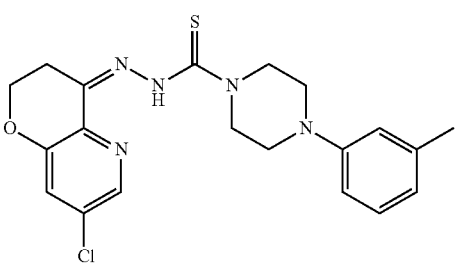
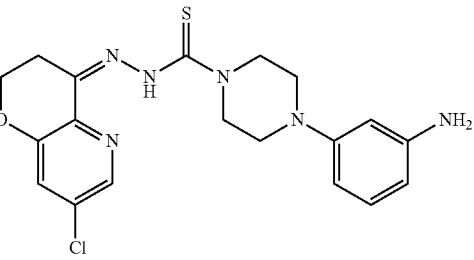
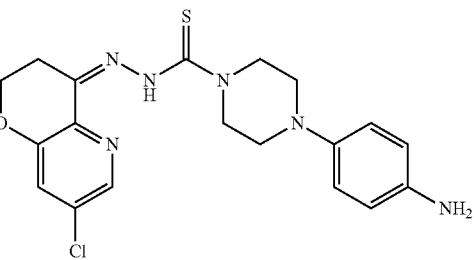

-continued
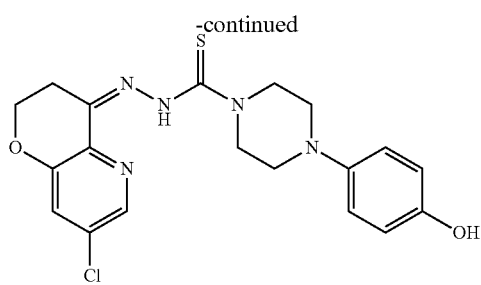
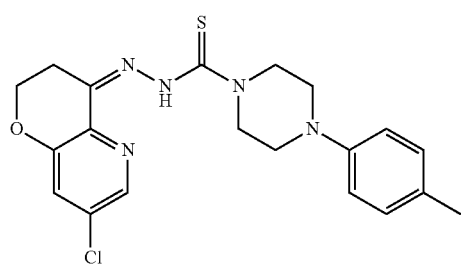
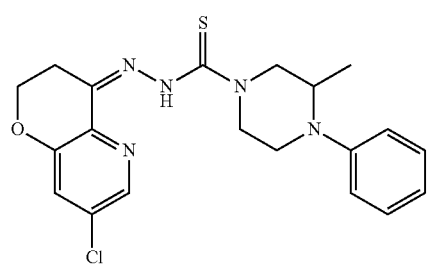
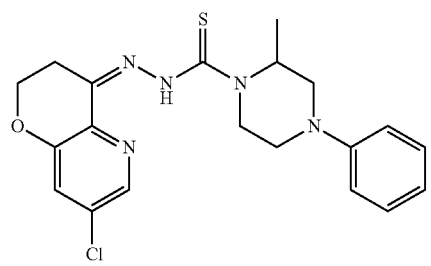
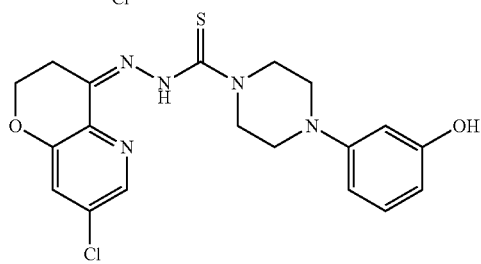
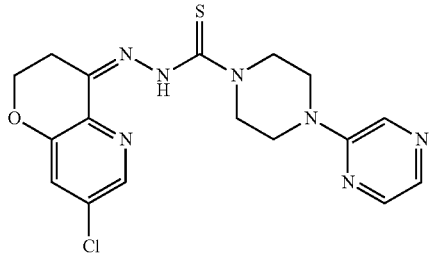
-continued
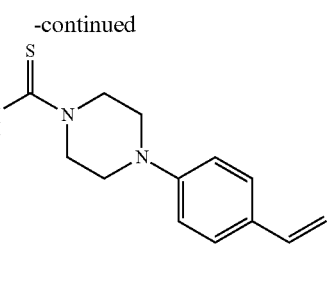
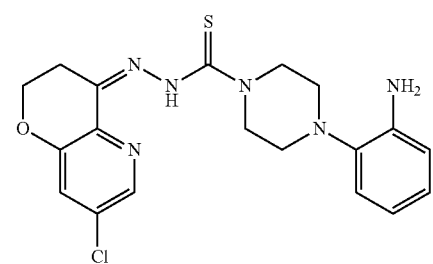
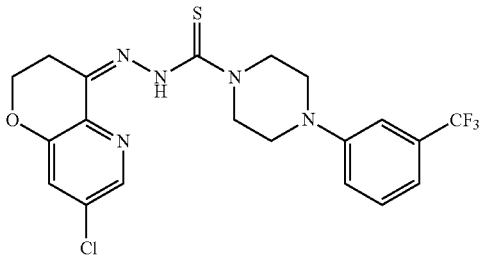
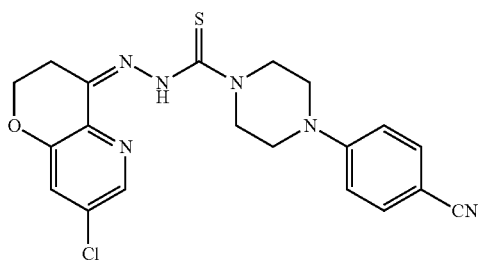
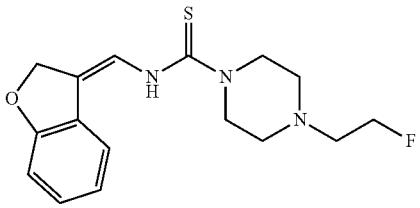
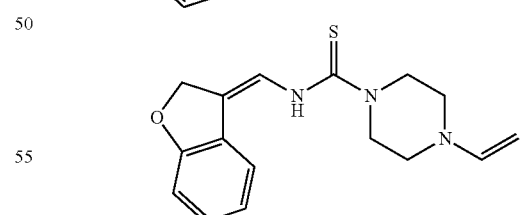
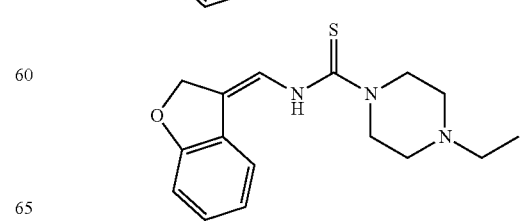

-continued
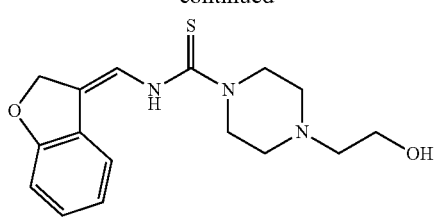
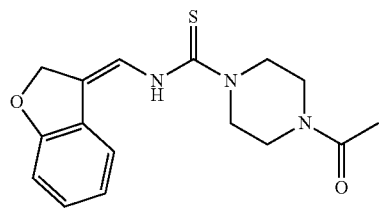
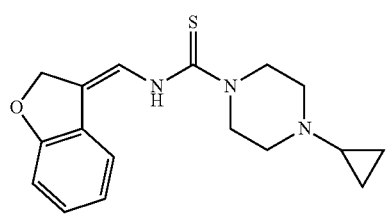
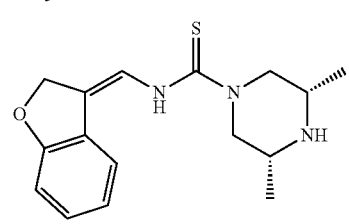
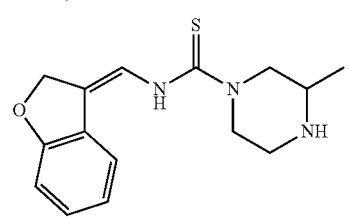
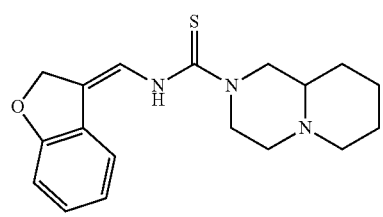
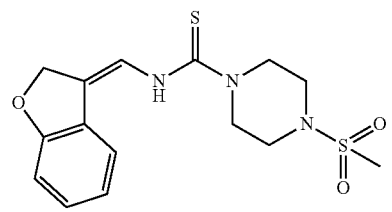
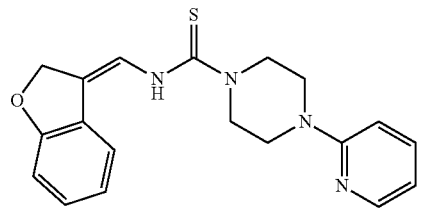
-continued
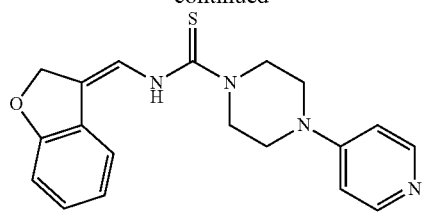
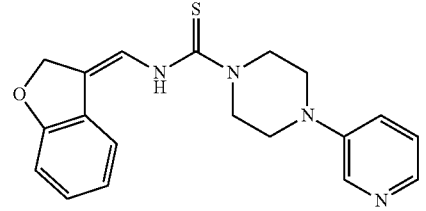
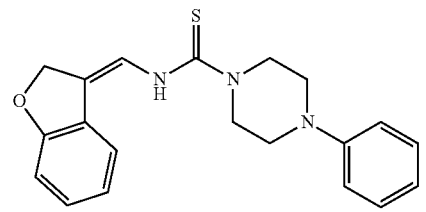
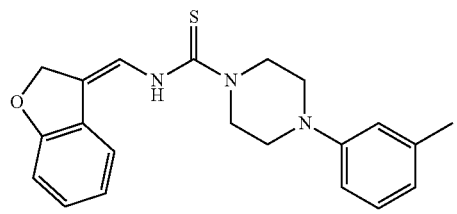
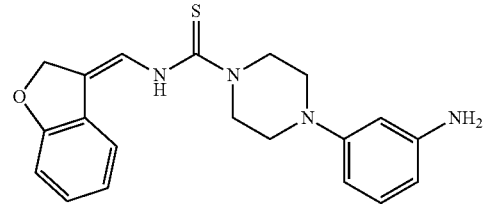
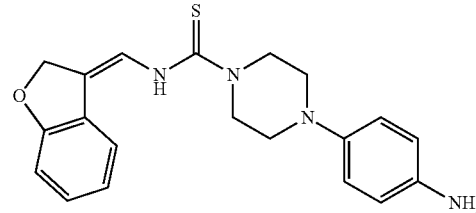
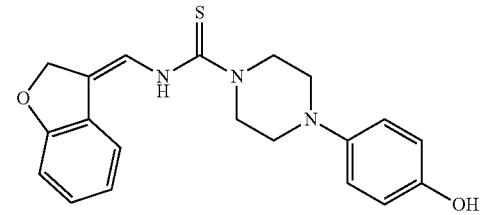
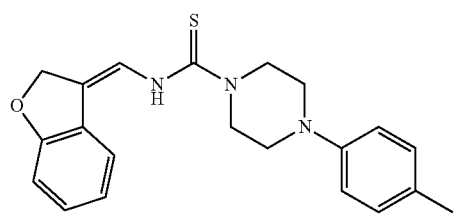

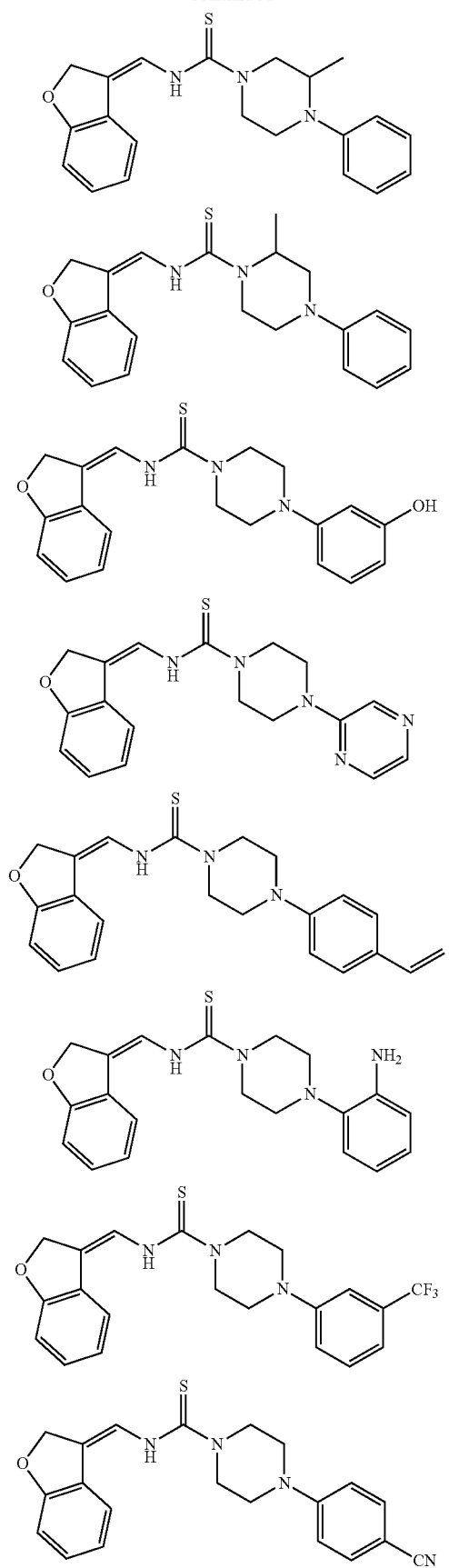
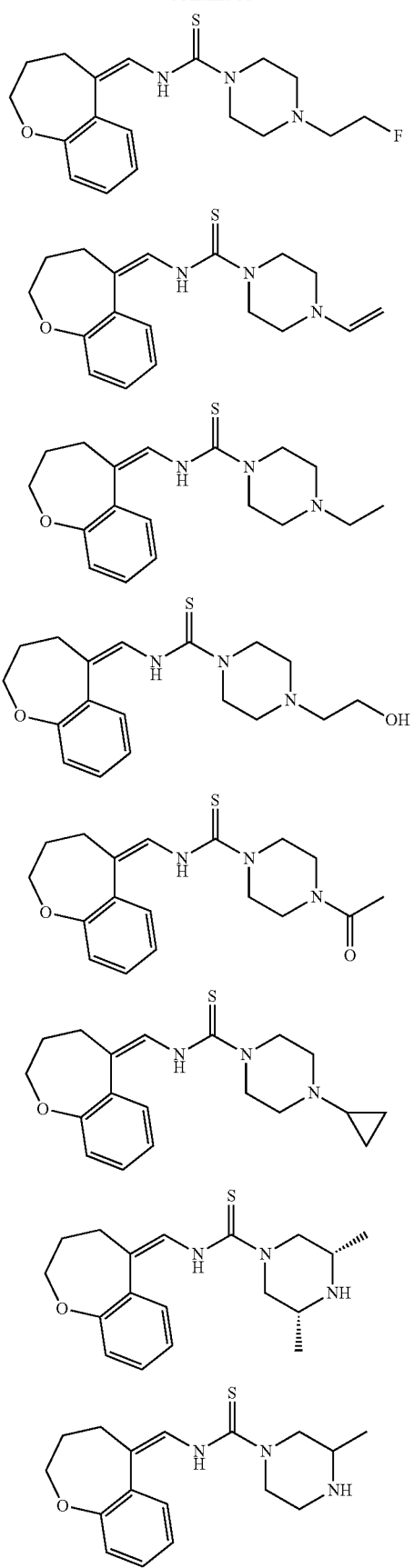

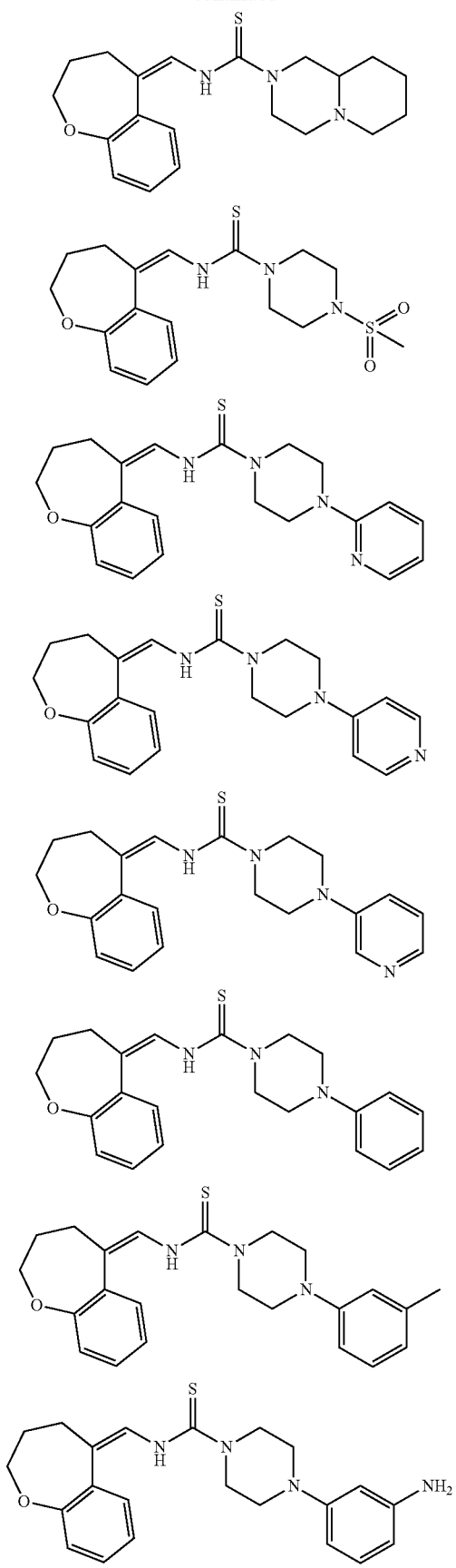
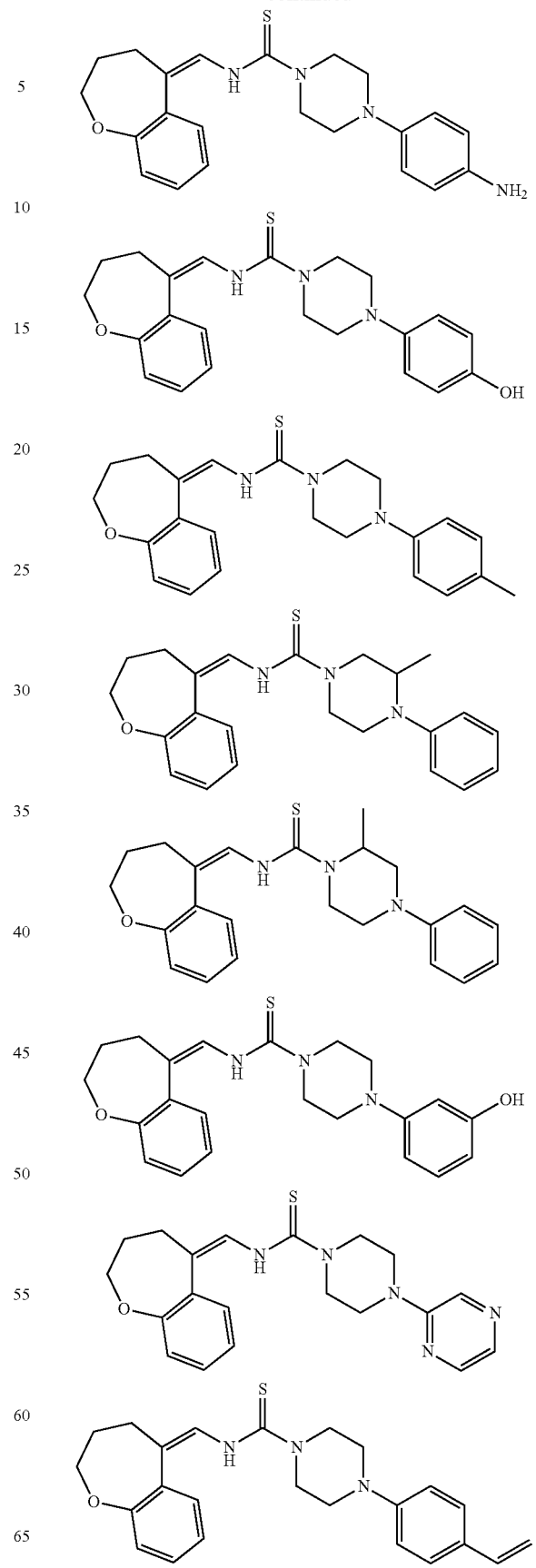

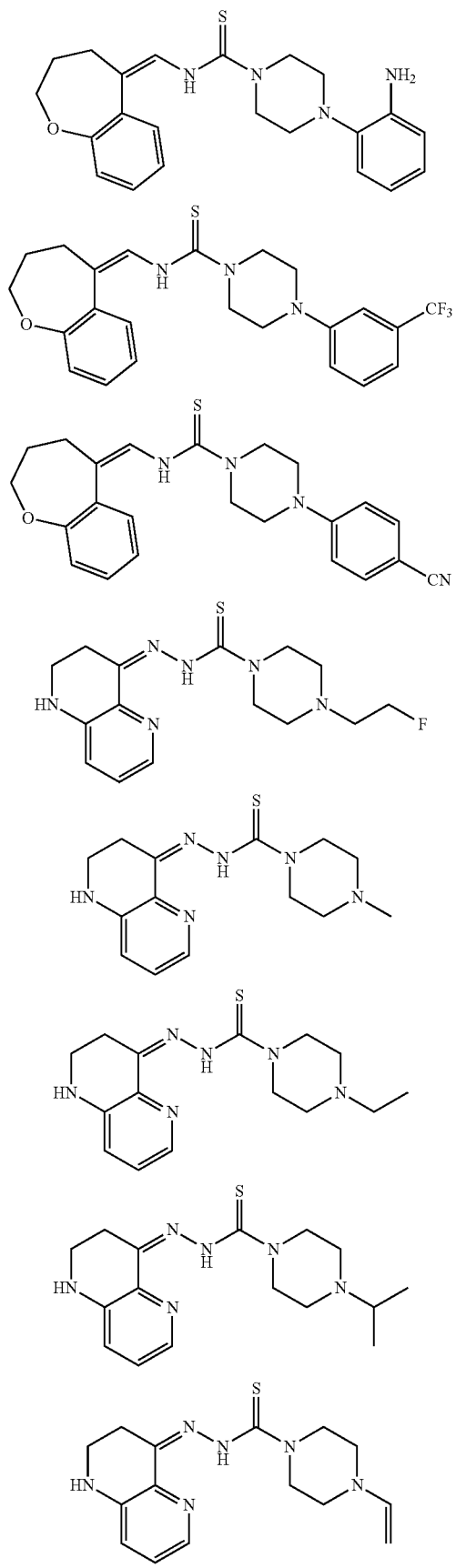
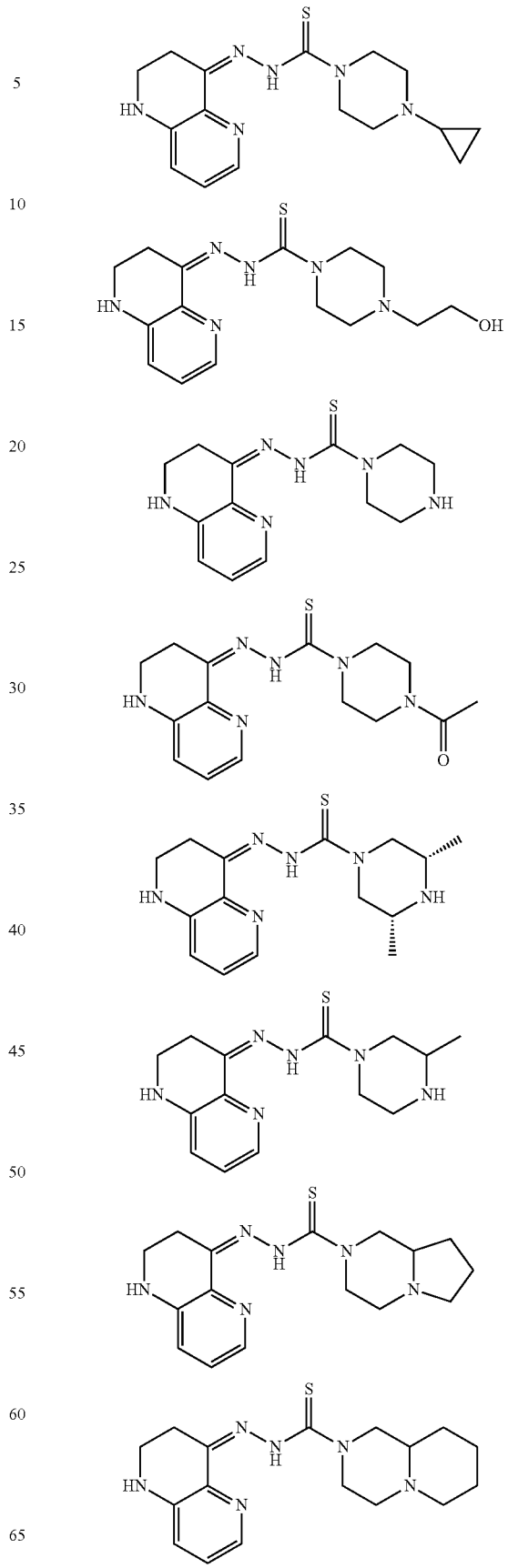

-continued
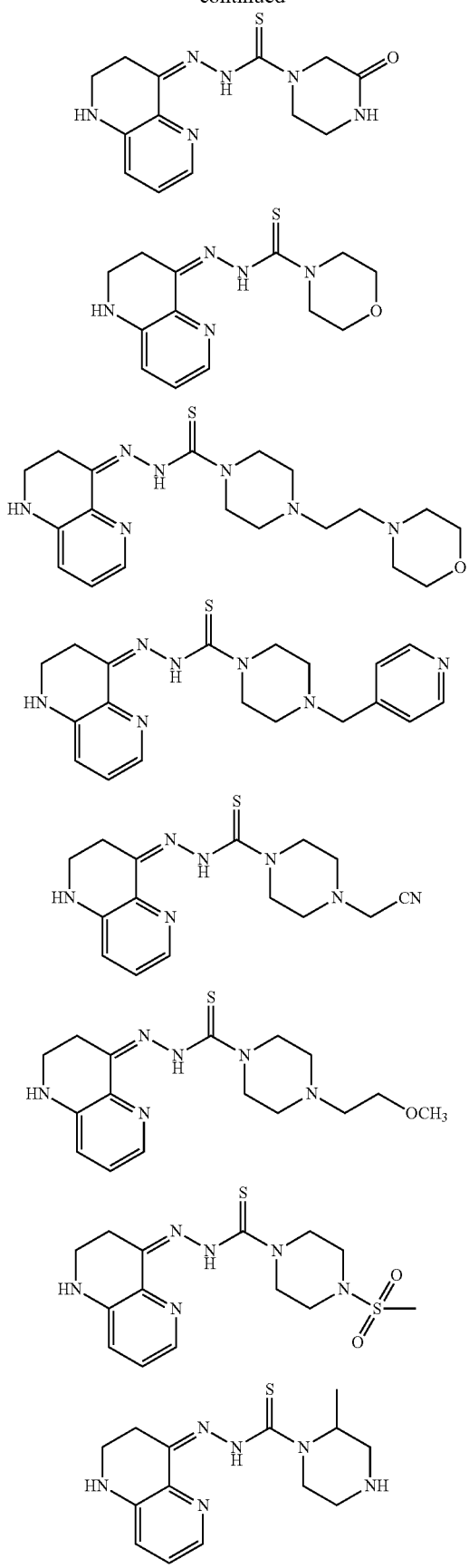
-continued
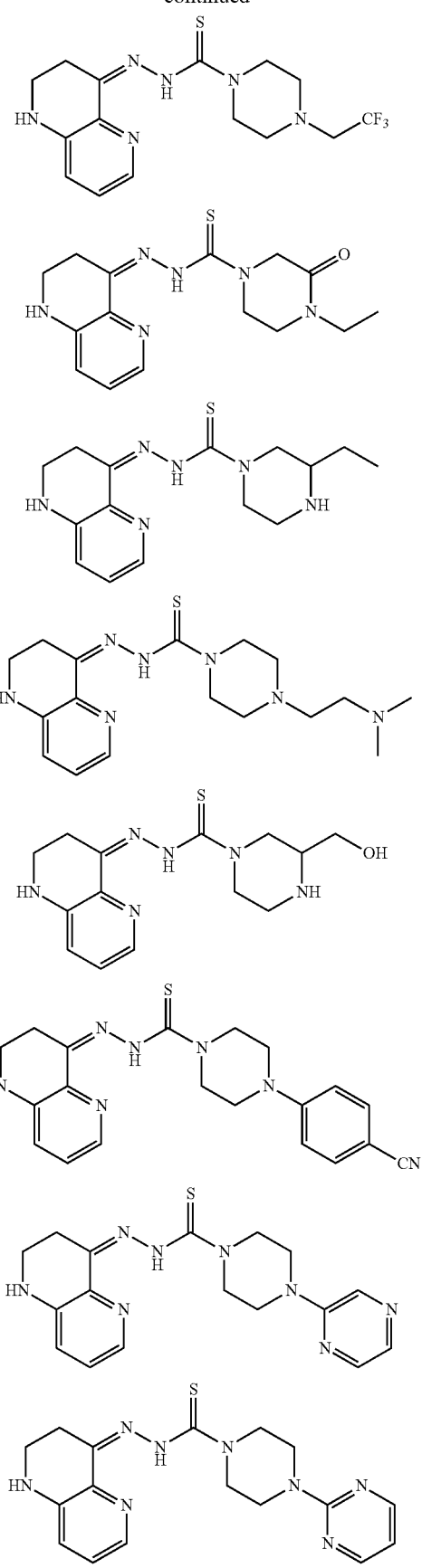

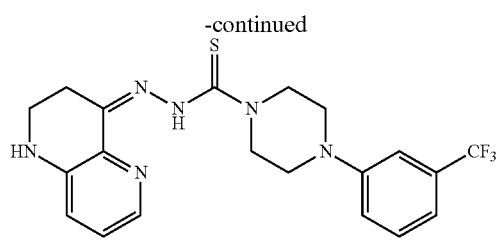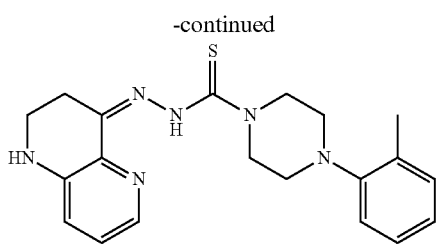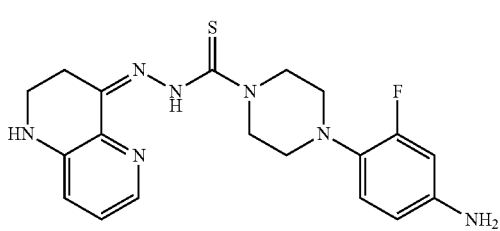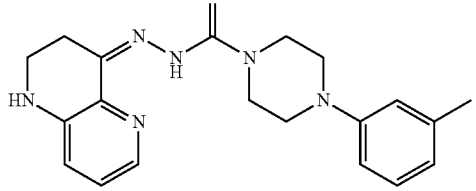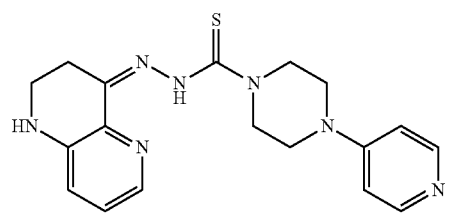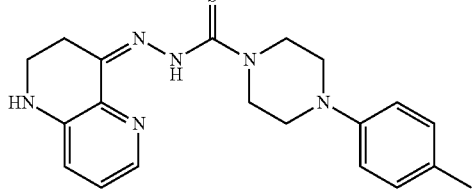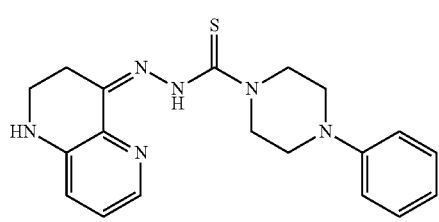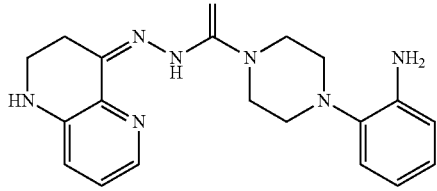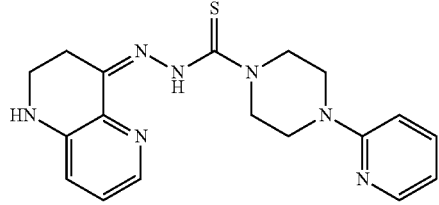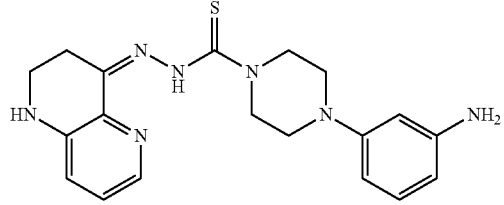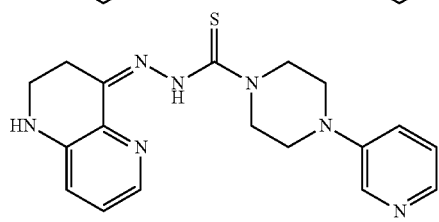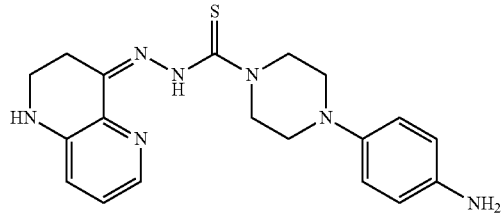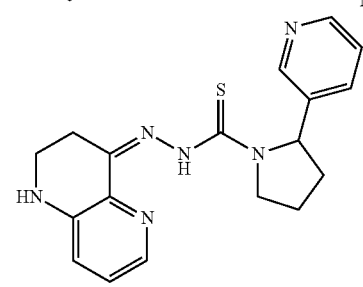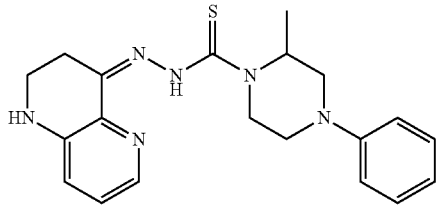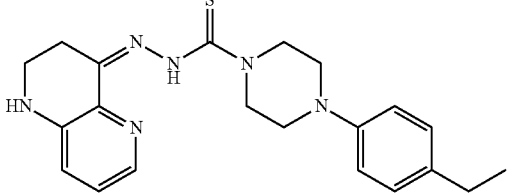

-continued

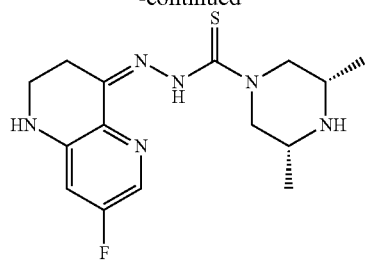
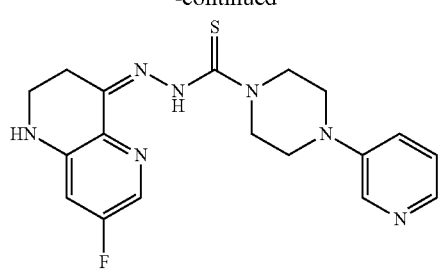
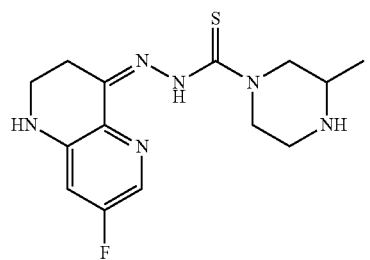
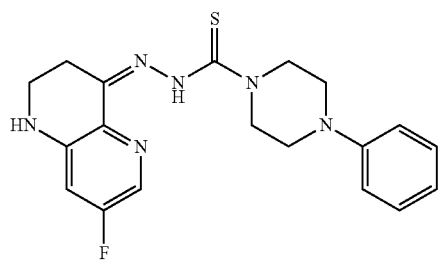
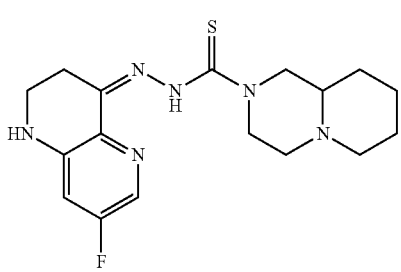
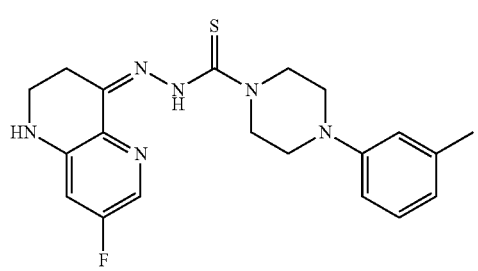
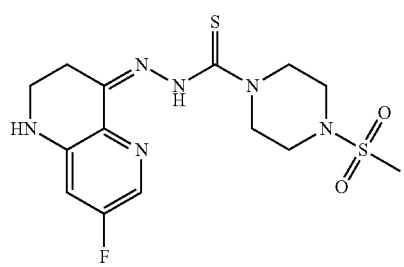
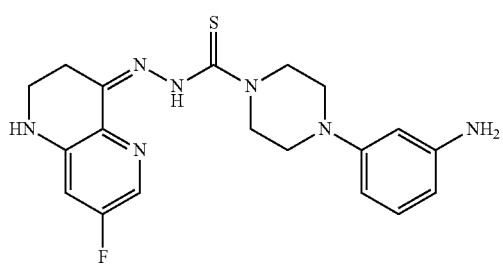
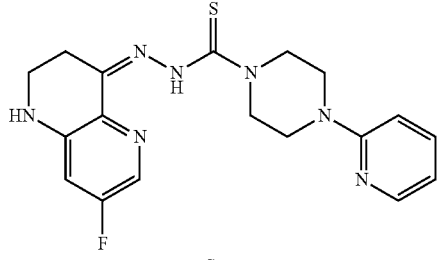
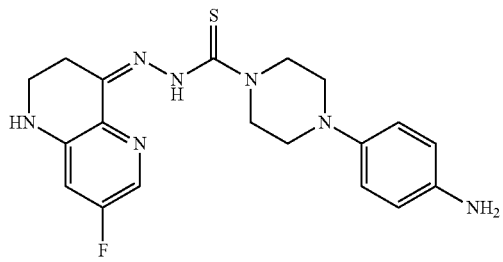
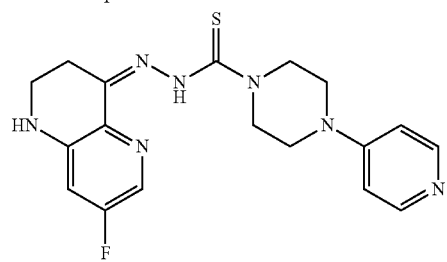
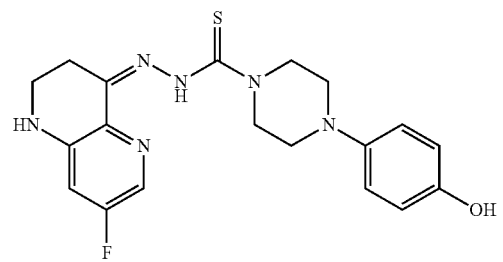

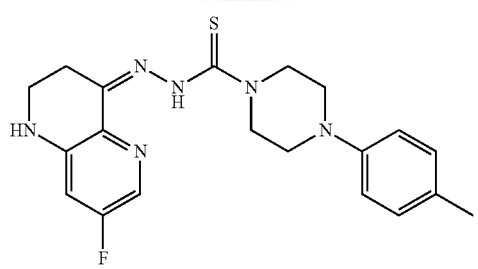
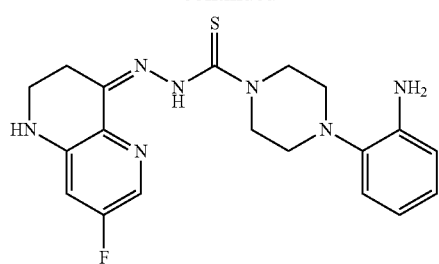
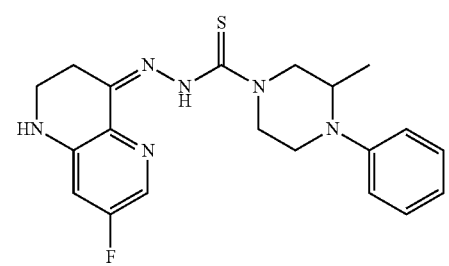
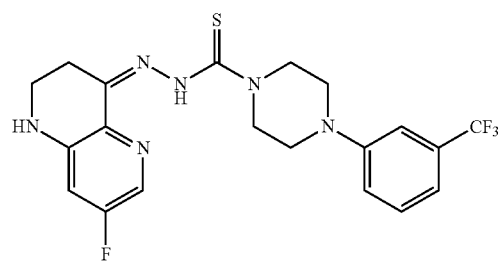
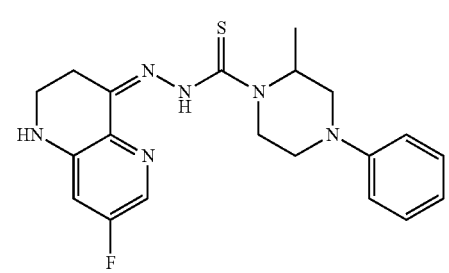
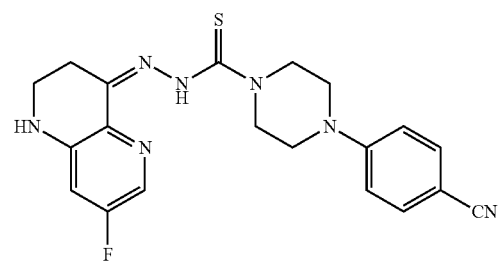
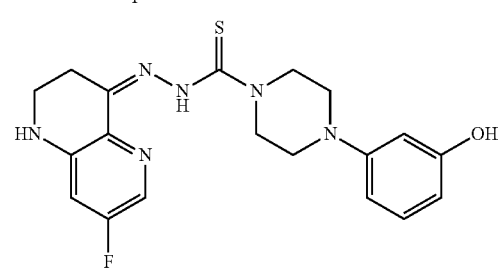
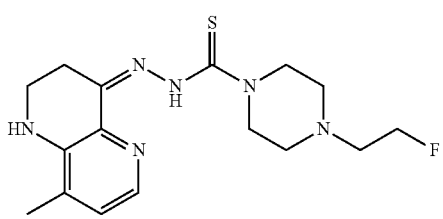
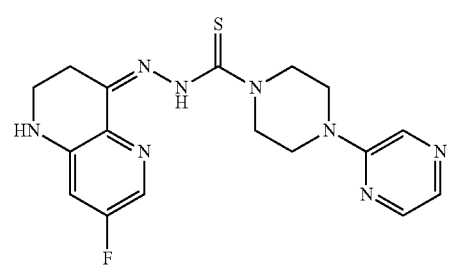
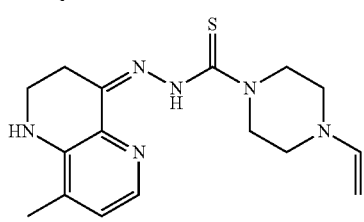
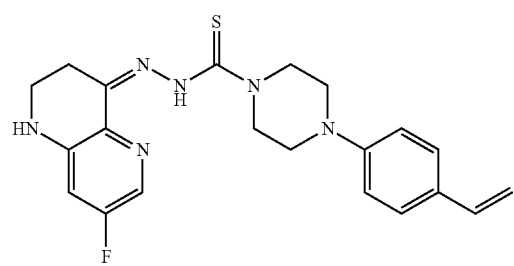
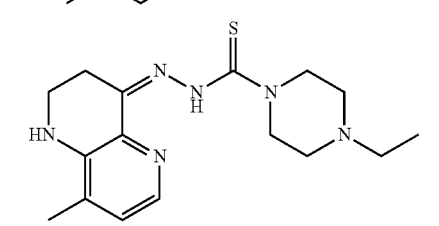

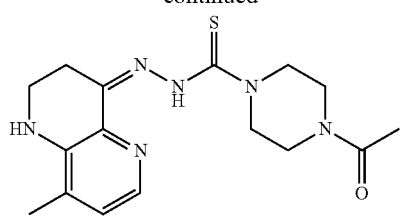
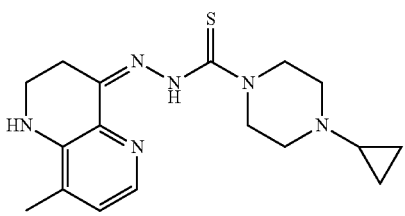
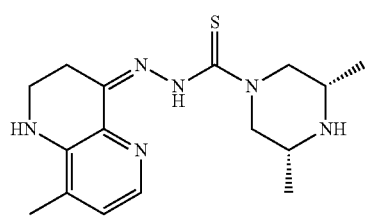
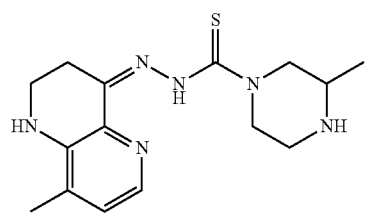
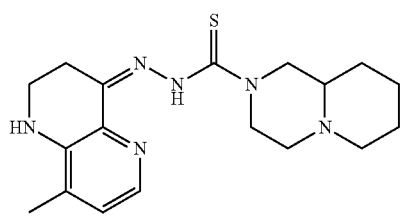
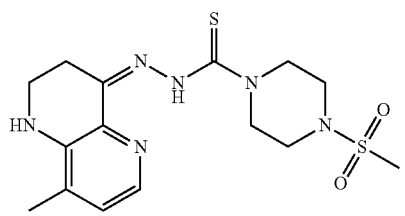
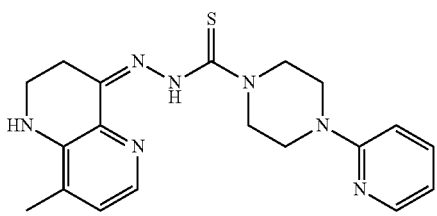
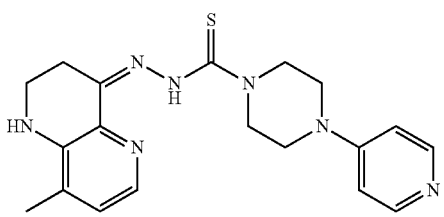
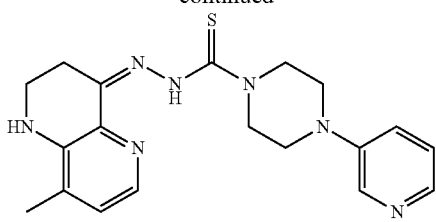
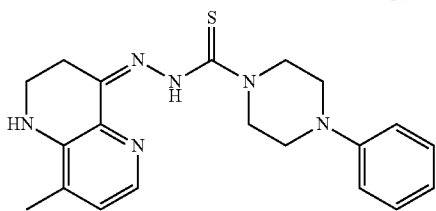
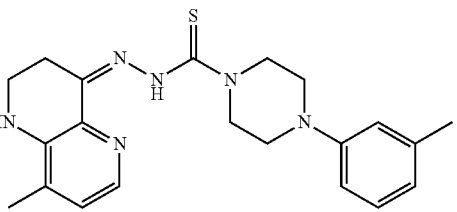
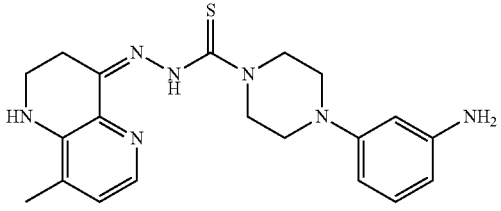
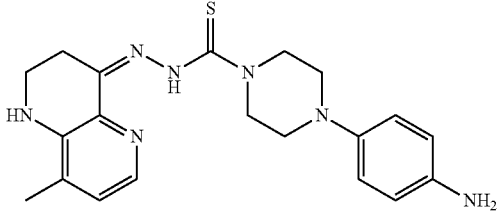
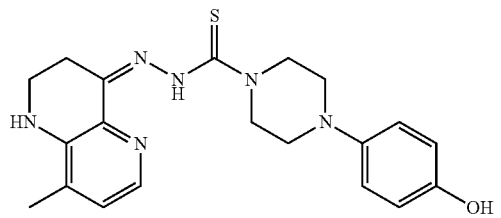
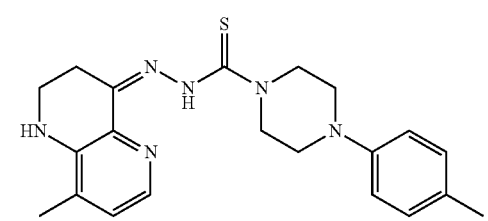
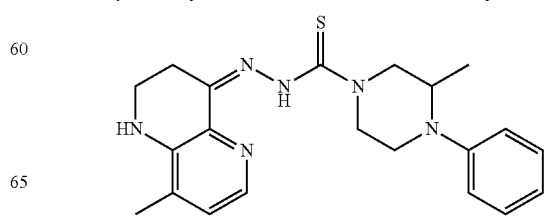

75
-continued
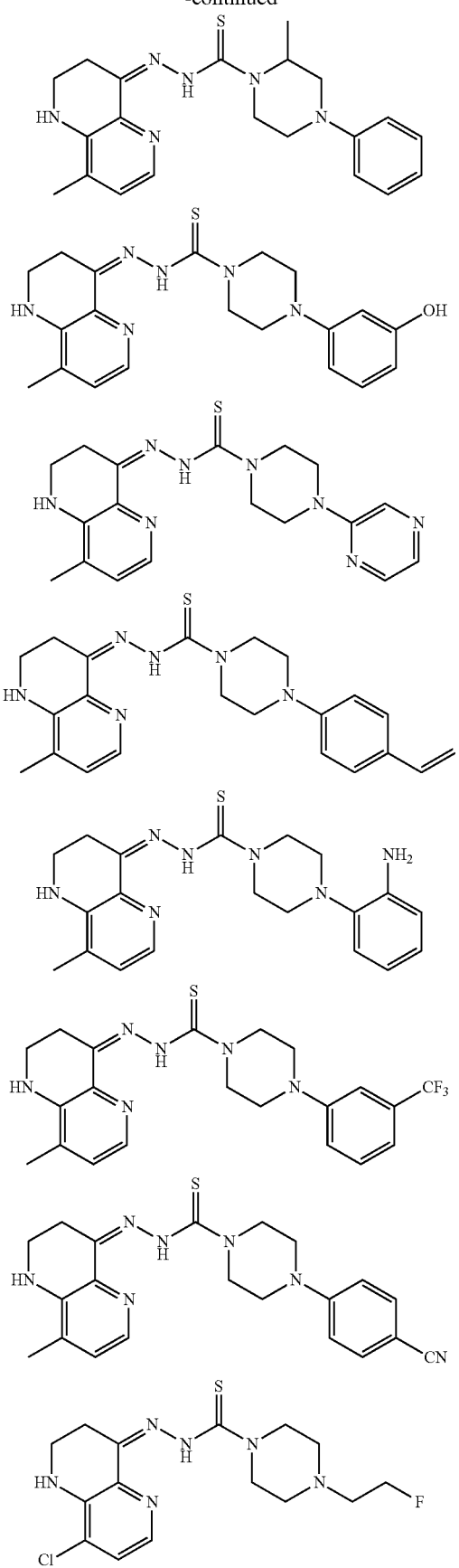
76
-continued
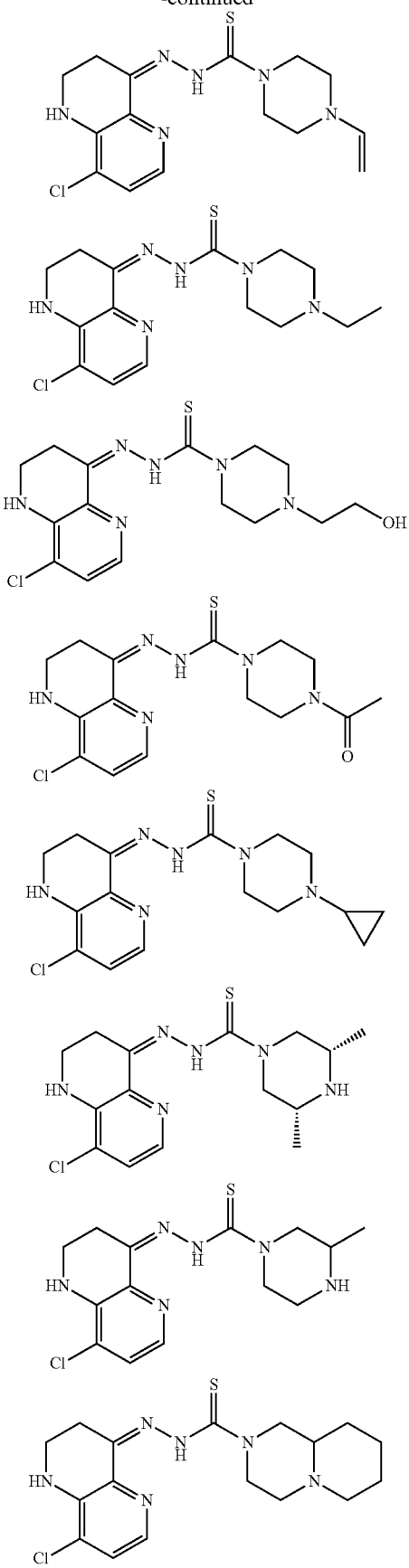

77
-continued
78
-continued
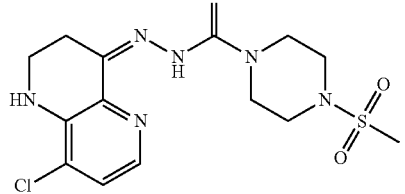
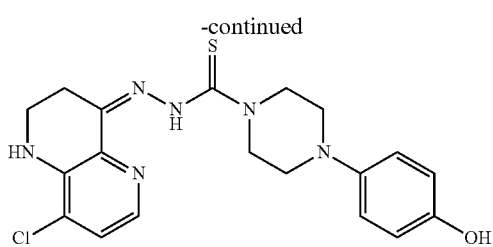

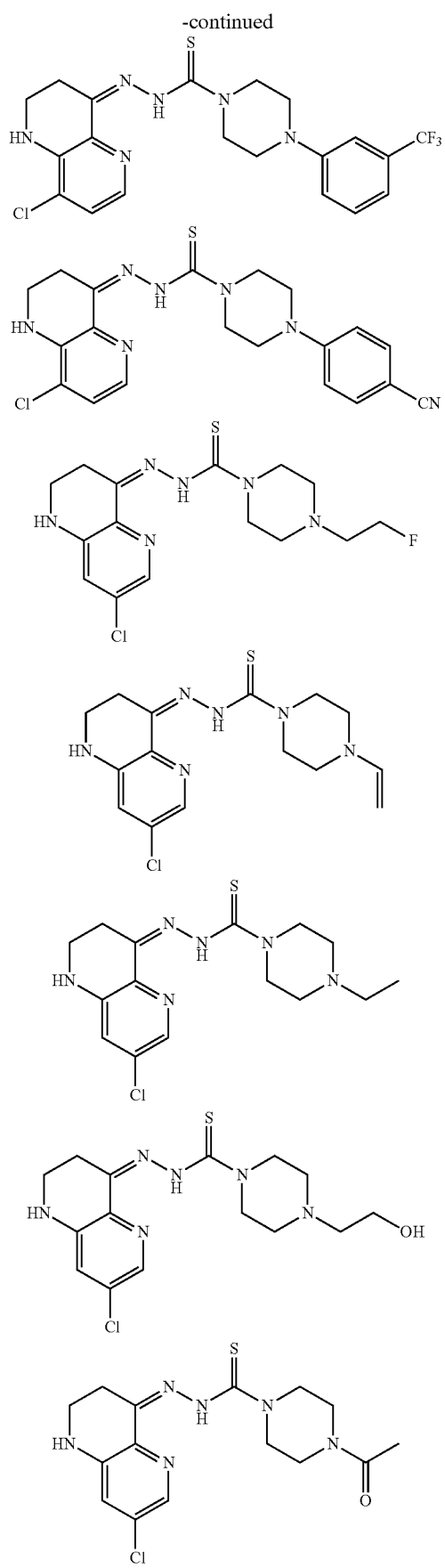
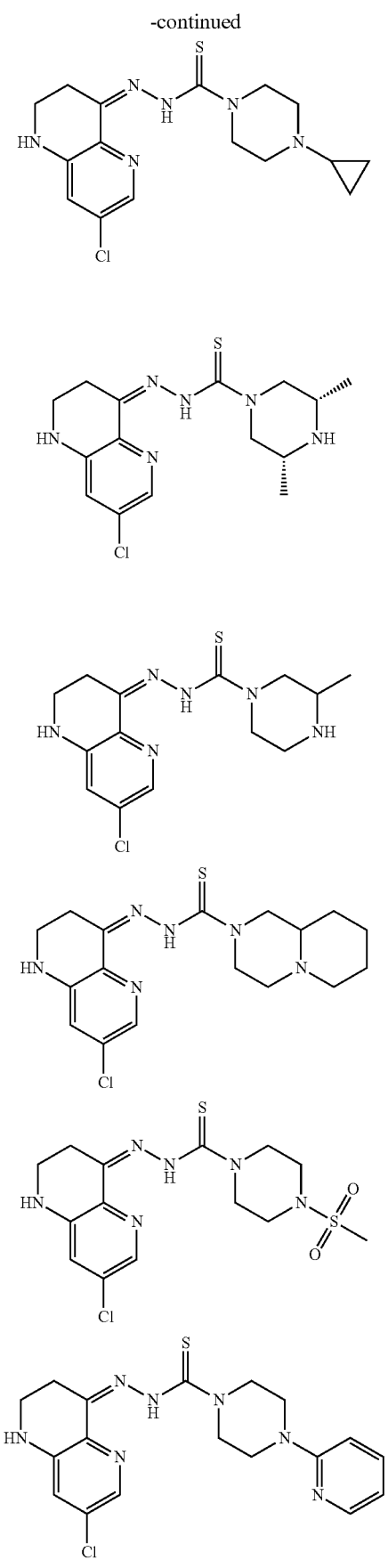

-continued
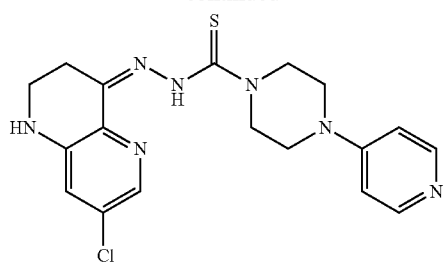
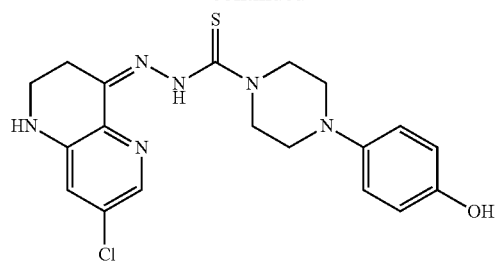
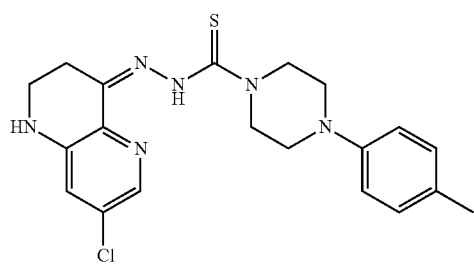
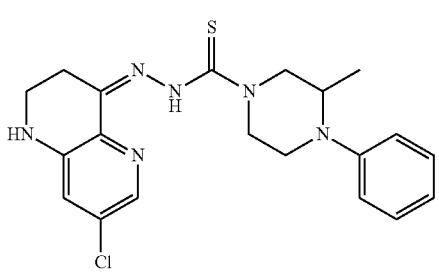
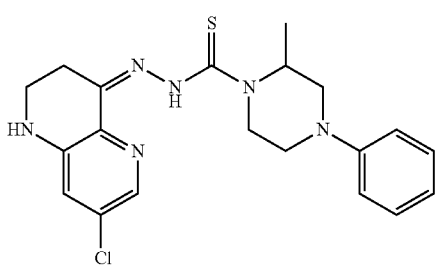
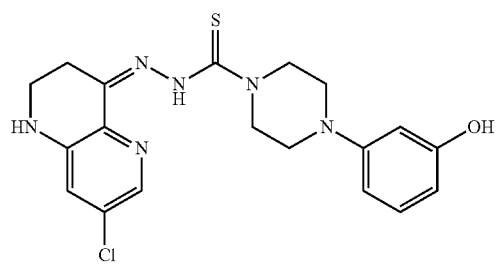
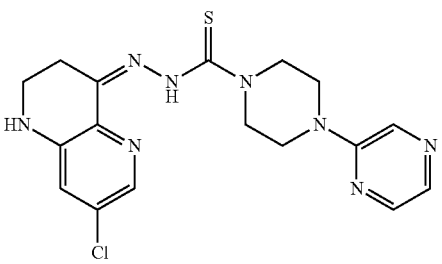

83
-continued
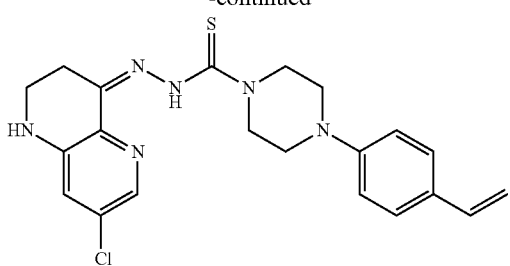
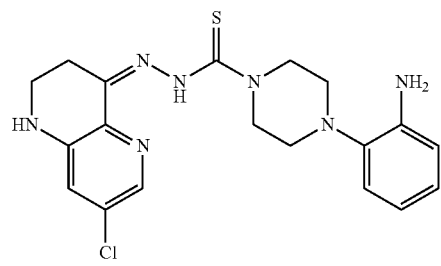
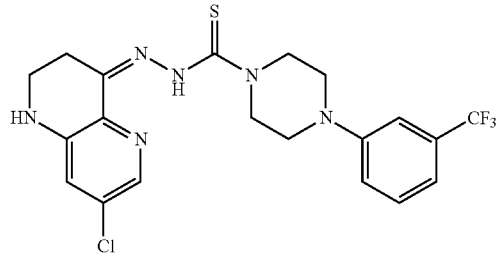
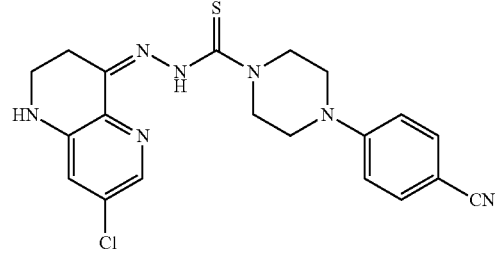
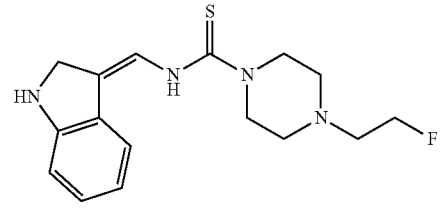
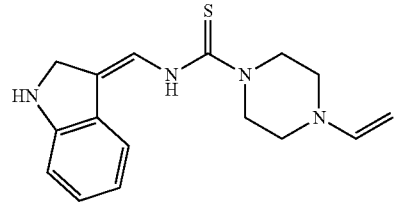
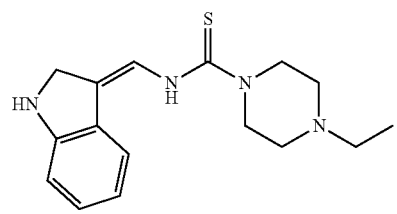
84
-continued
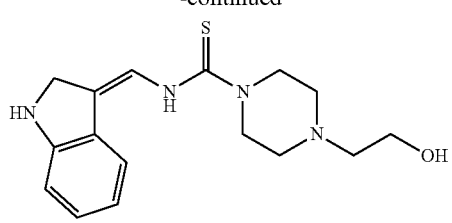
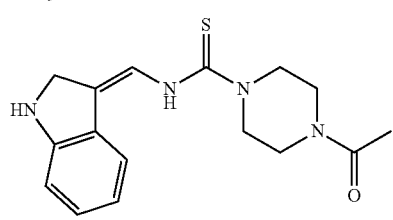
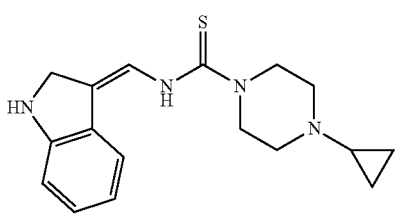
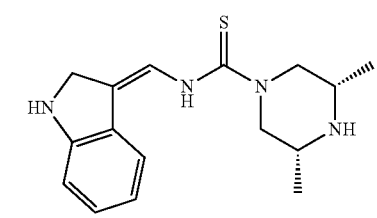
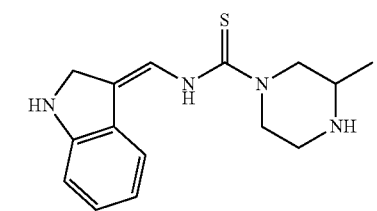
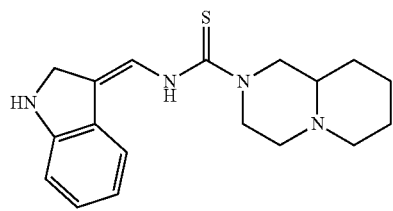
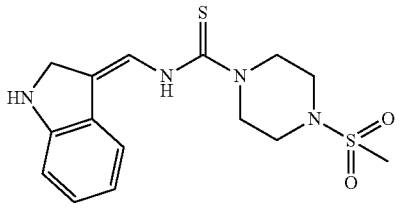
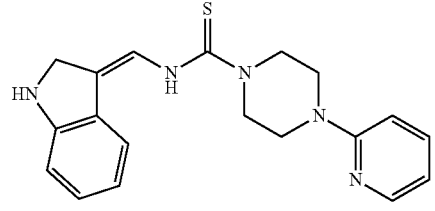

85
-continued
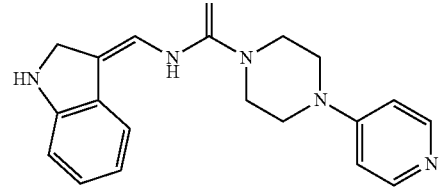
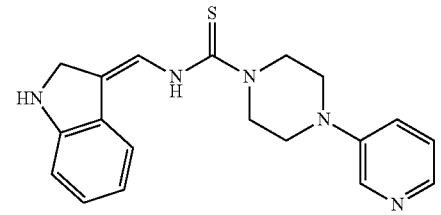
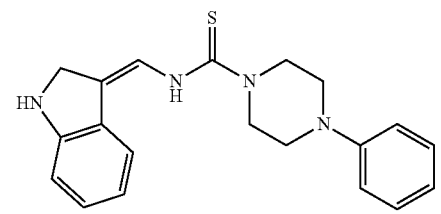
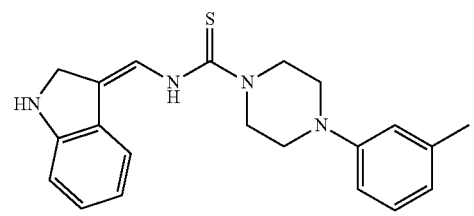
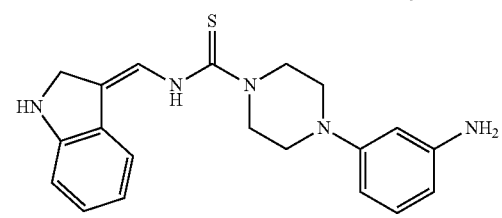
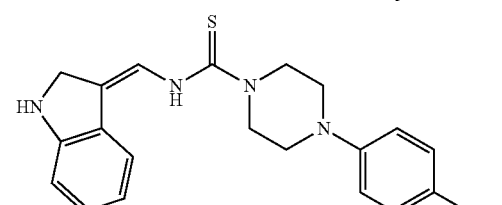
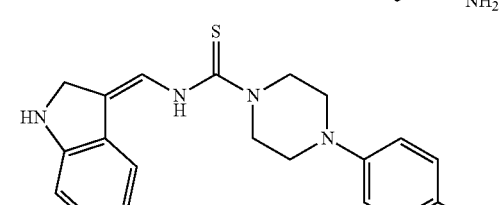
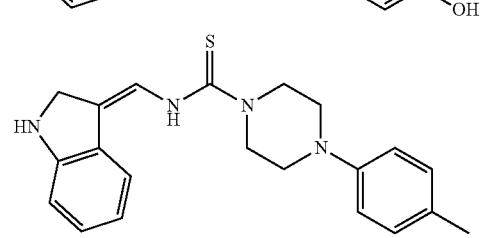
86
-continued
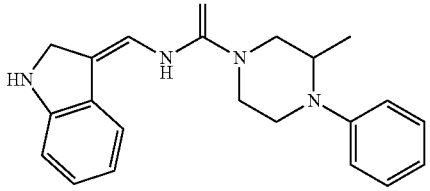
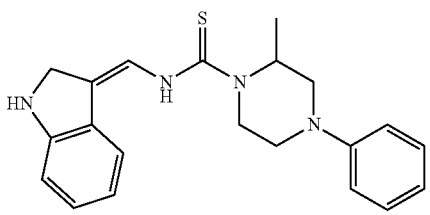
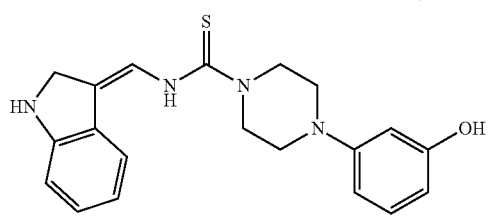
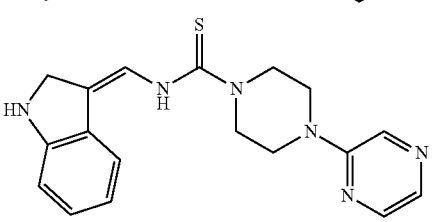
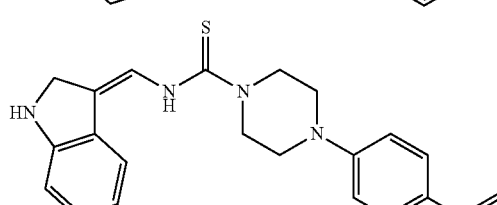
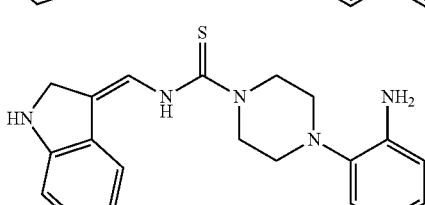
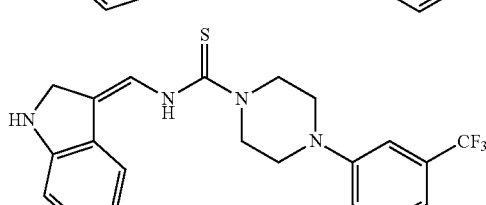
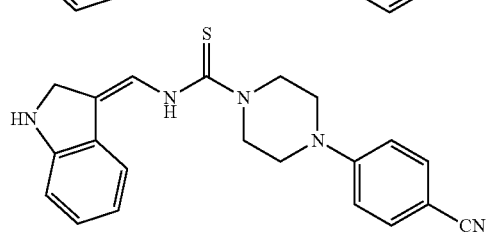

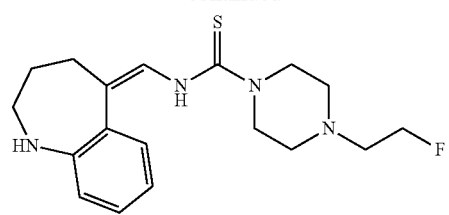
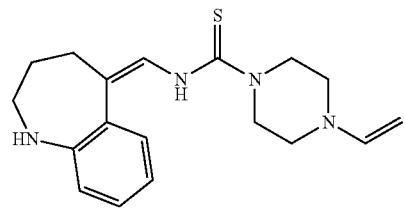
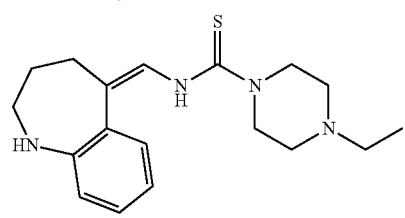
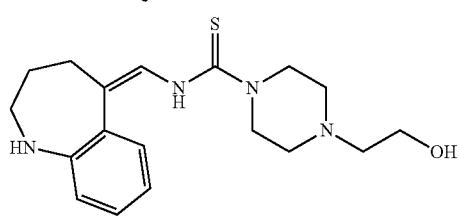
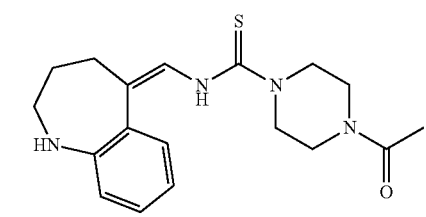
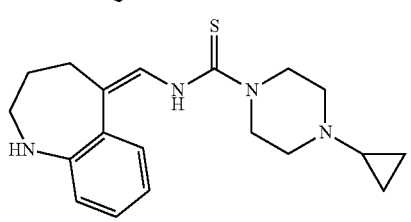
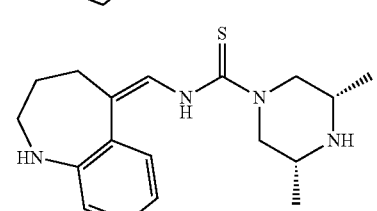
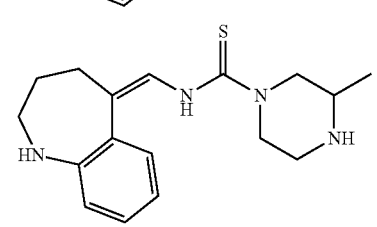
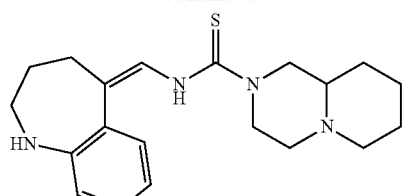
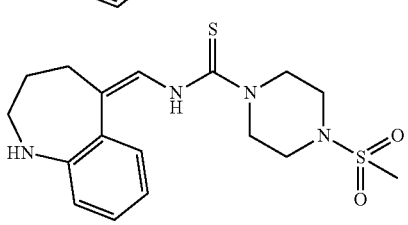
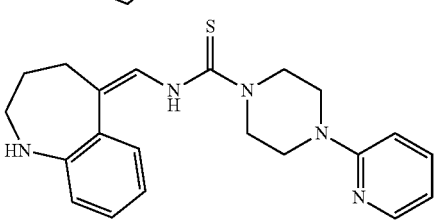
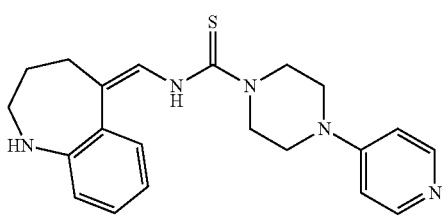
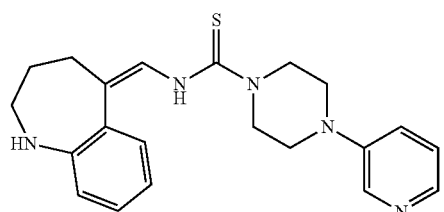
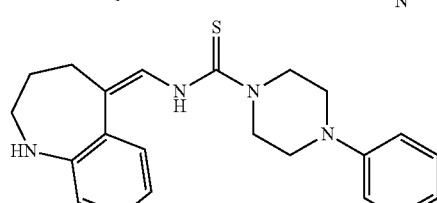
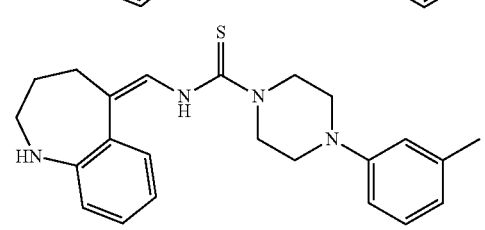
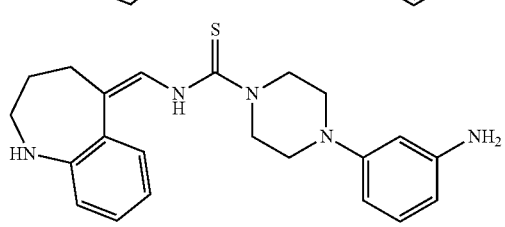

89
-continued
90
-continued
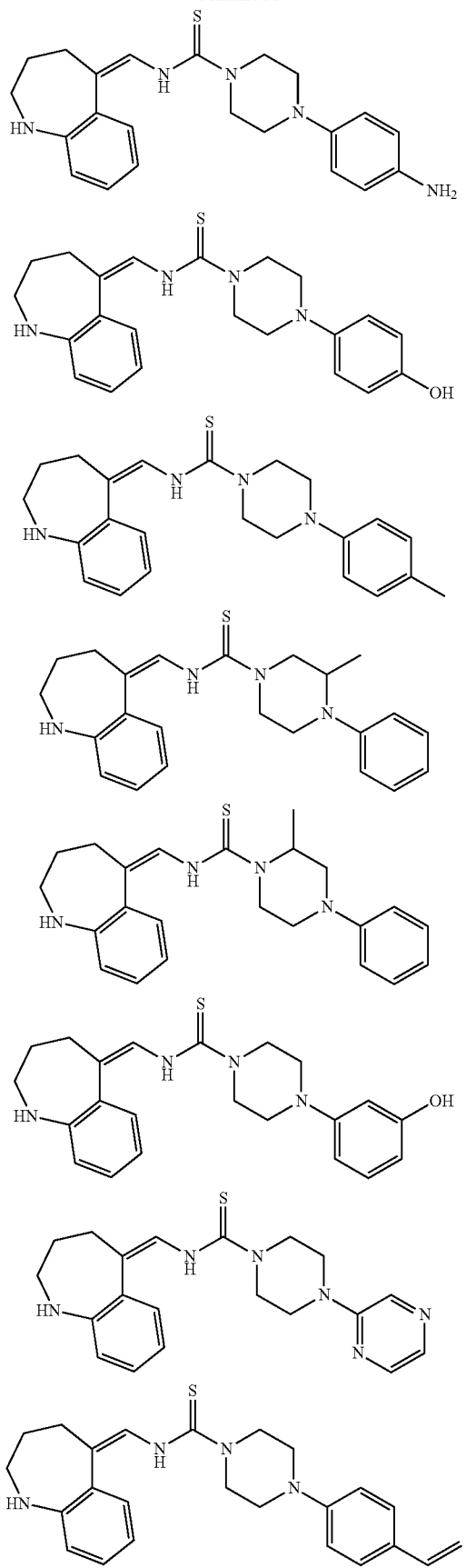
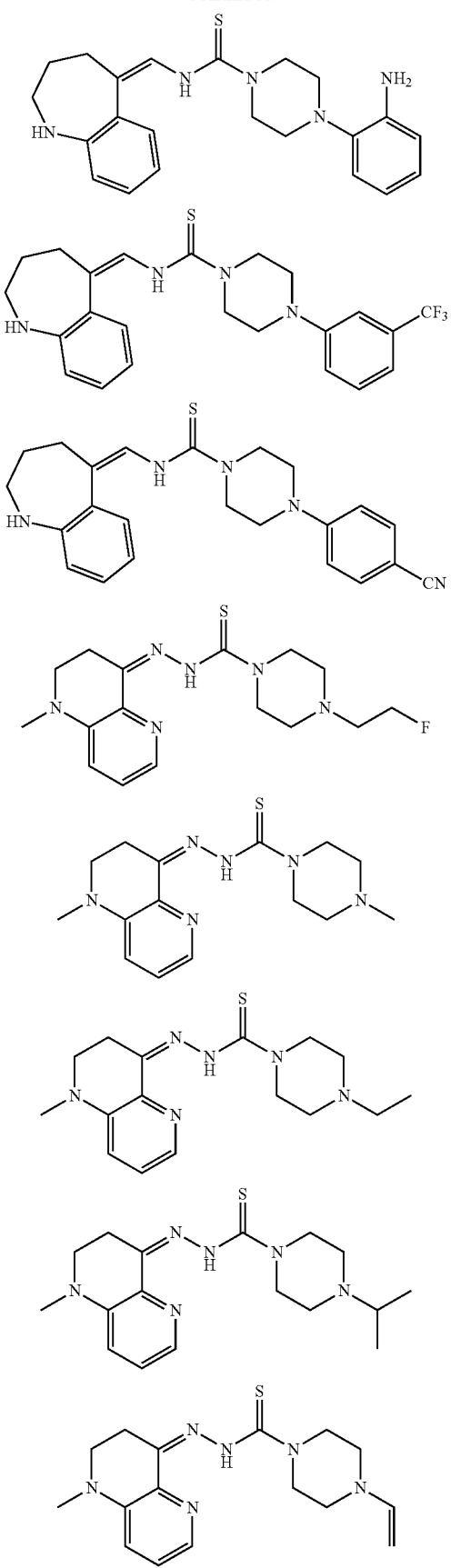

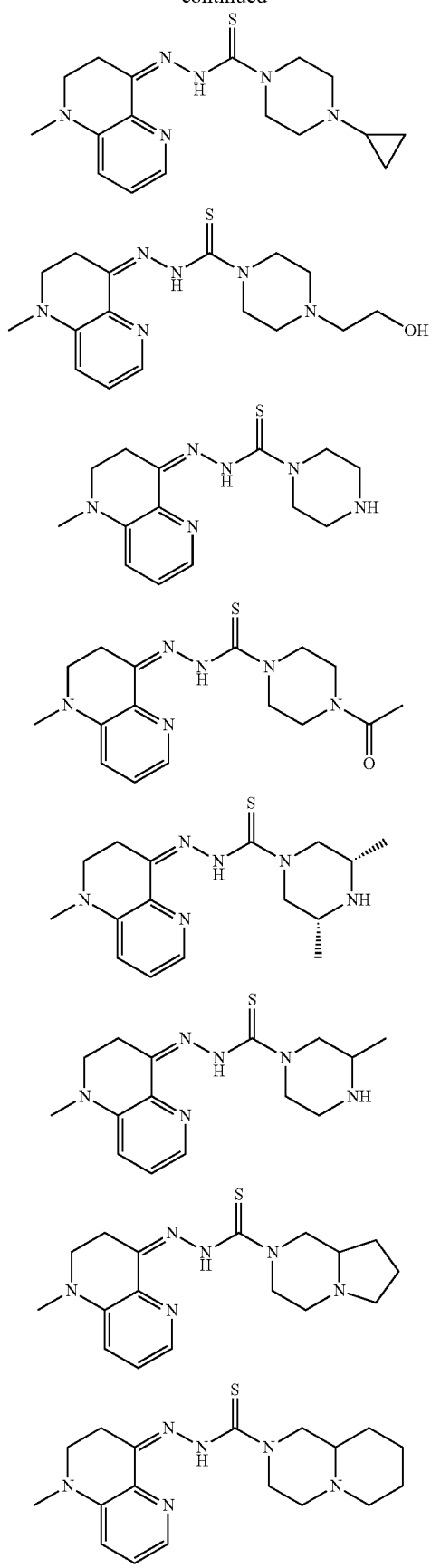
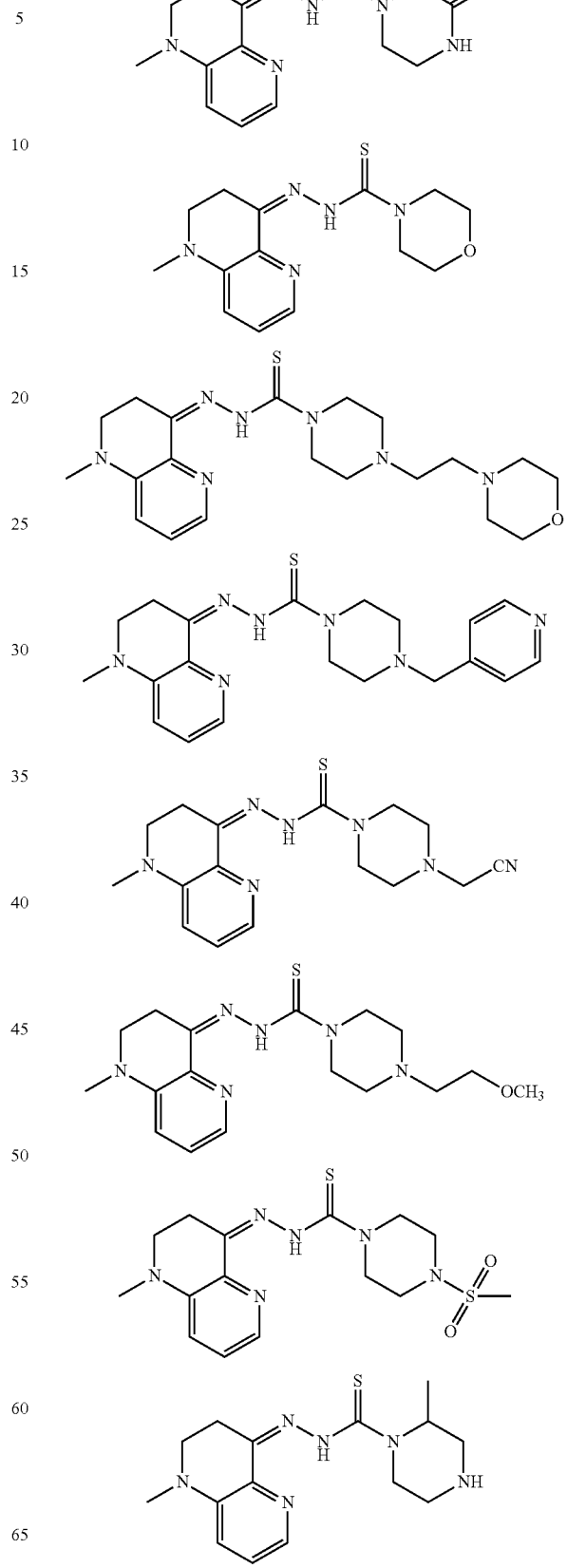

93
-continued
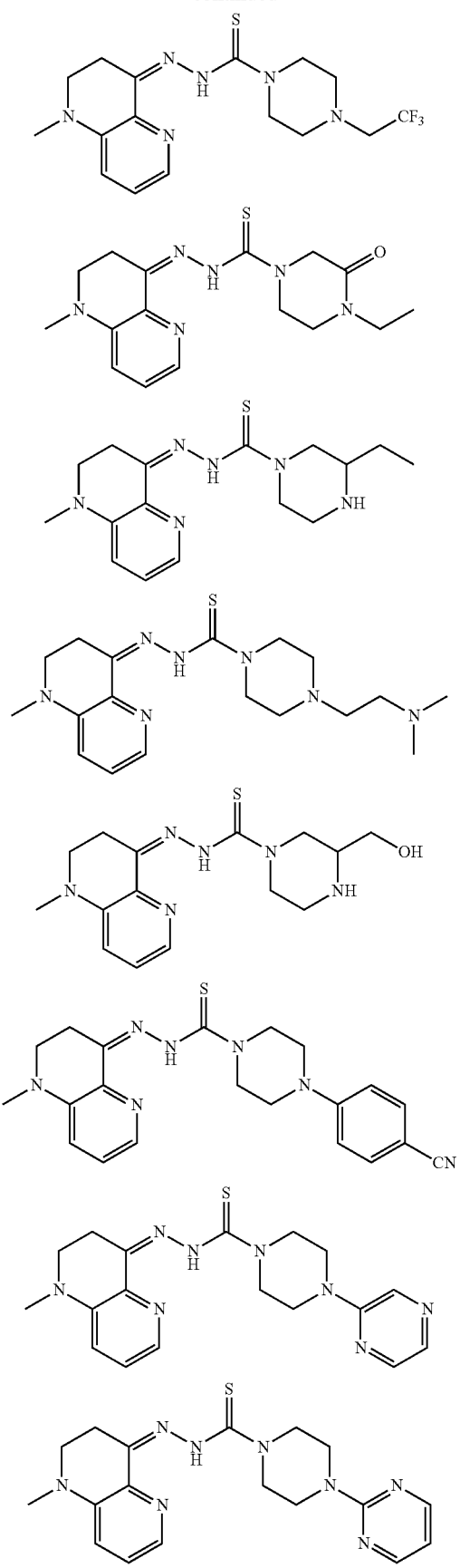
94
-continued
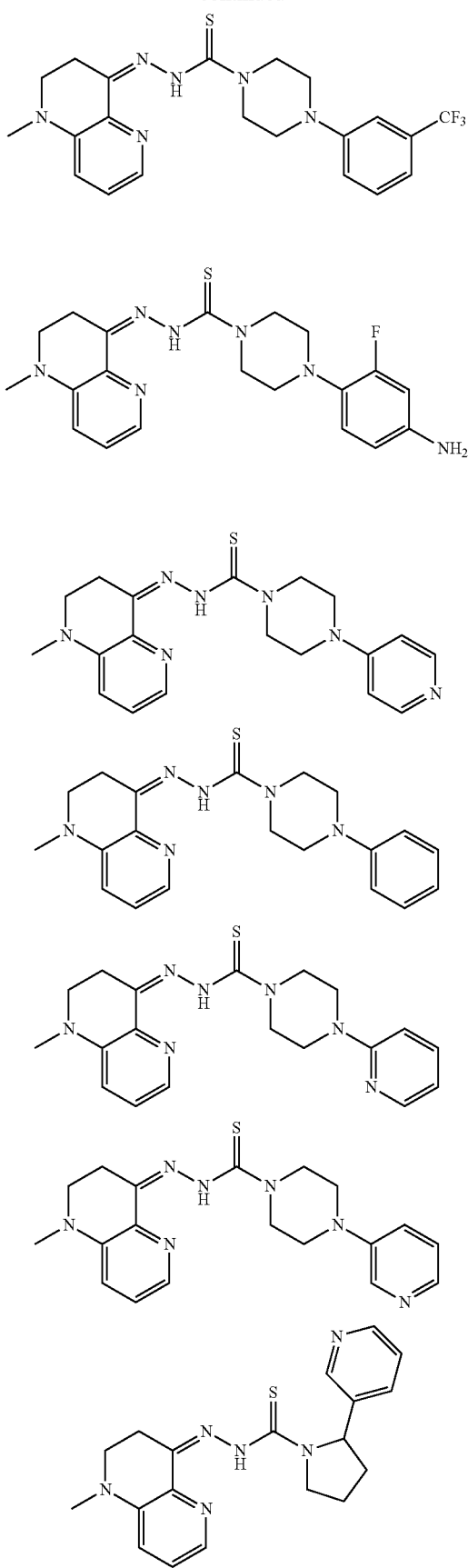

95
-continued
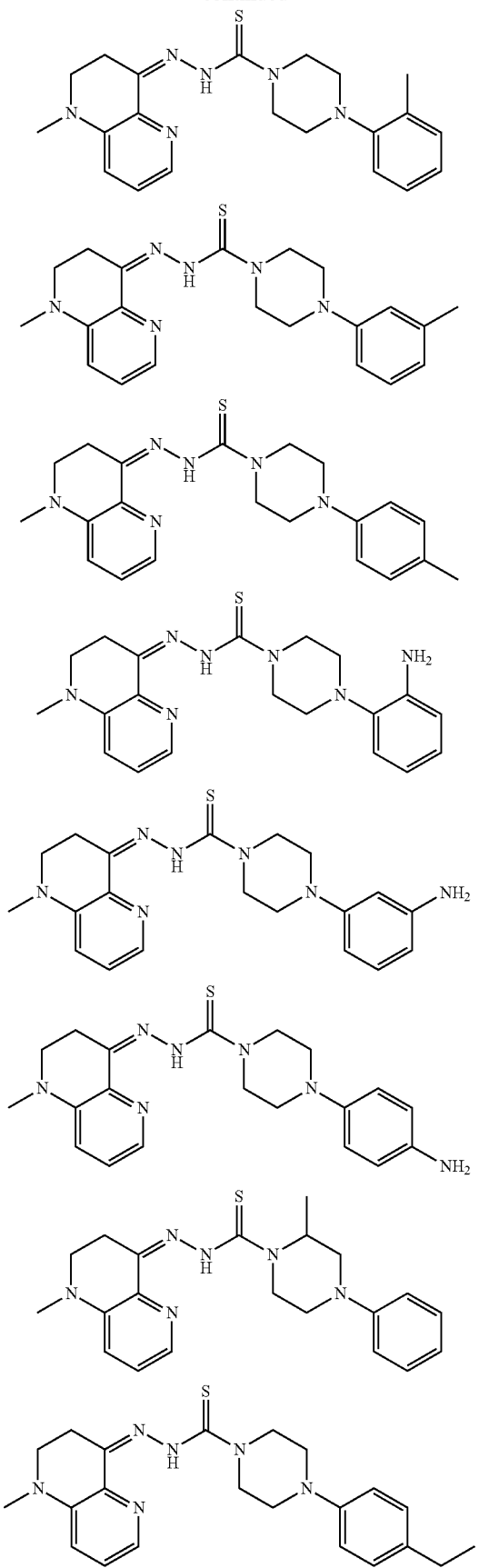
96
-continued
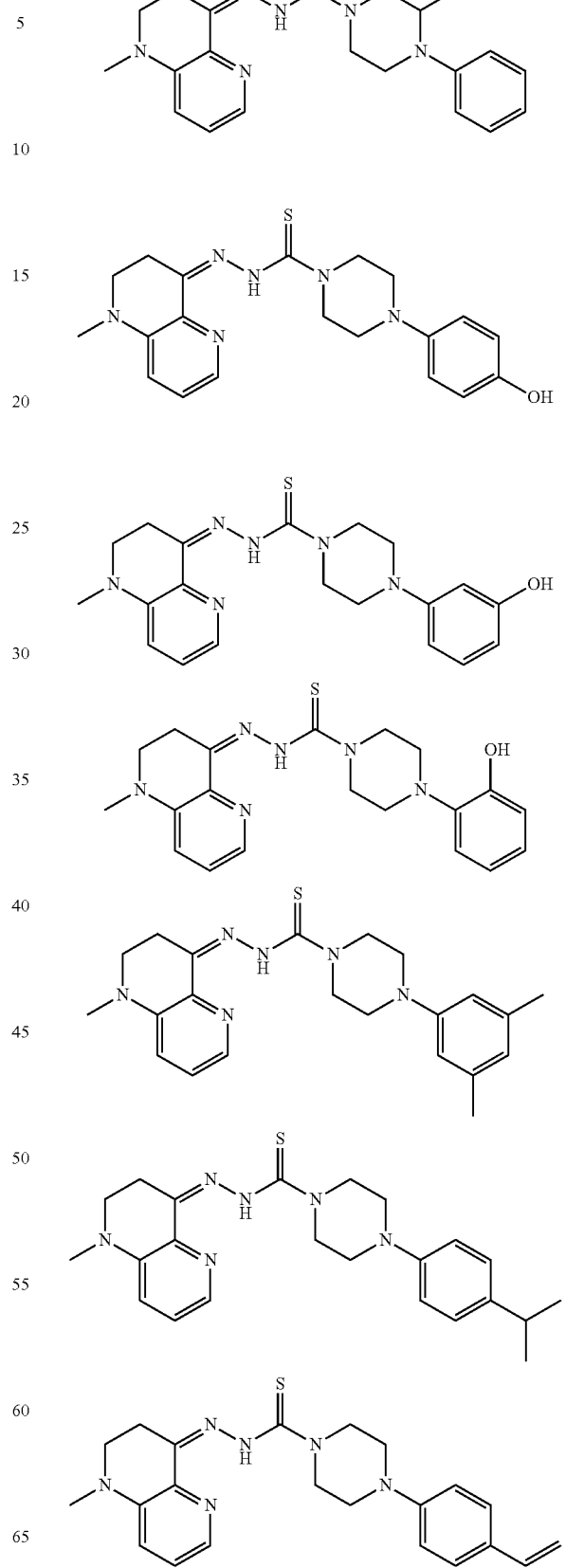

97
-continued
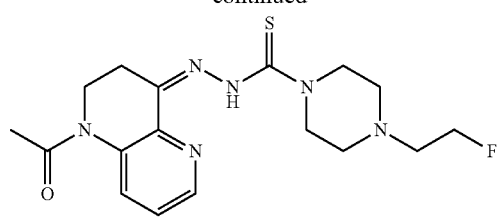
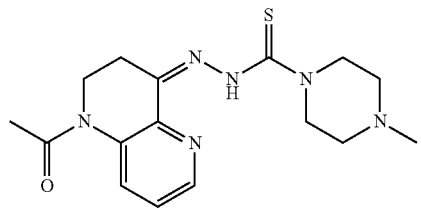
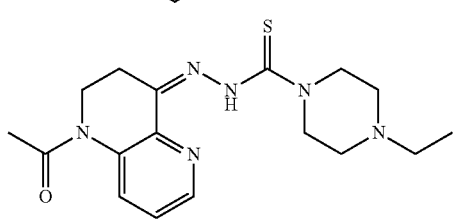
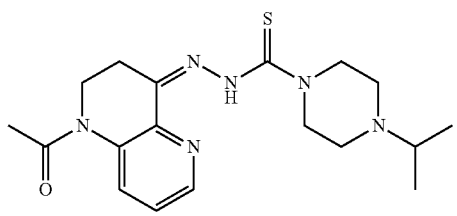
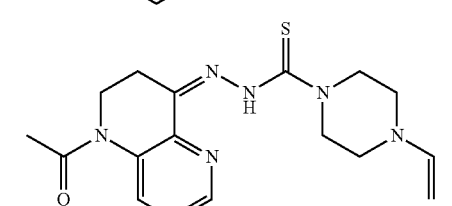
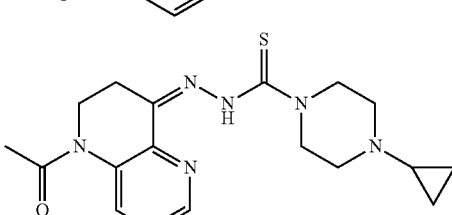
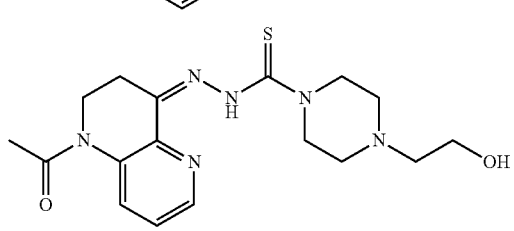
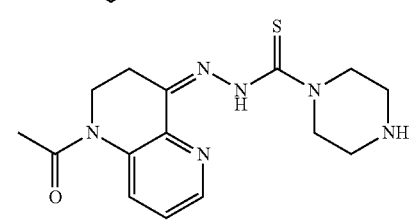
98
-continued
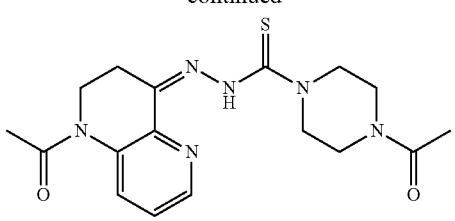
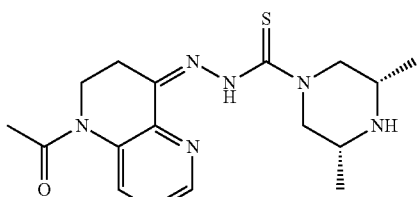
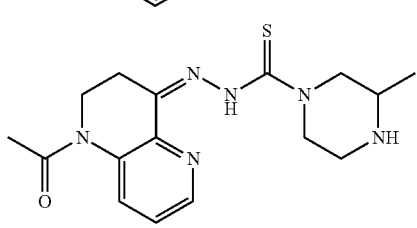
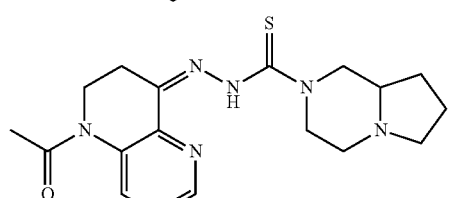
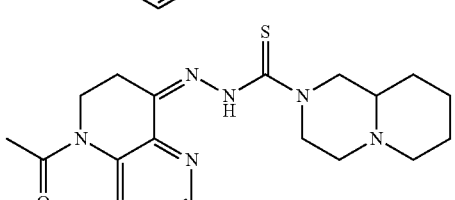
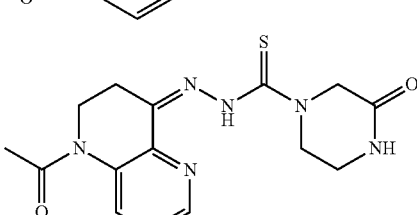
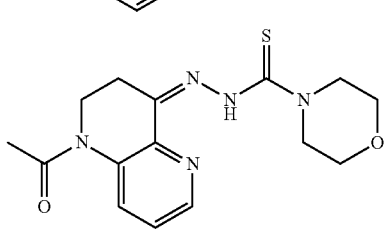
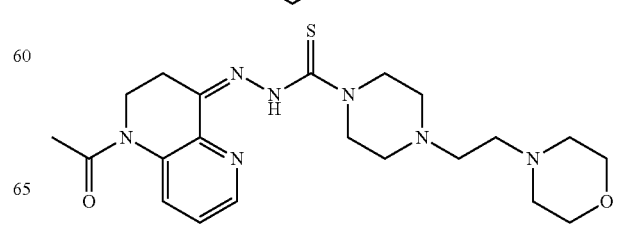

99 | 100
---|---
-continued | -continued
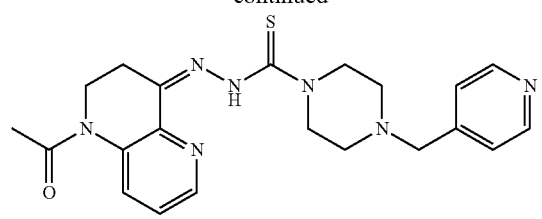 | 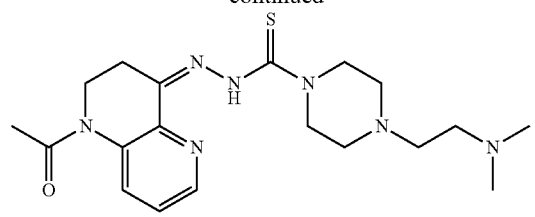
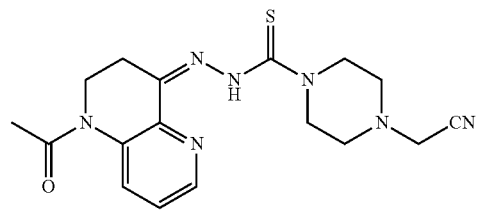 | 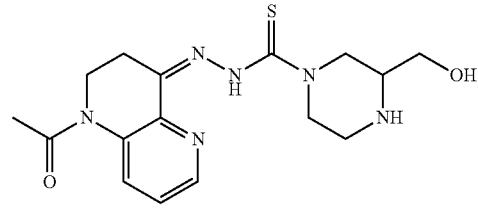
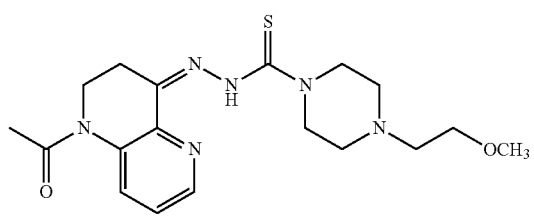 | 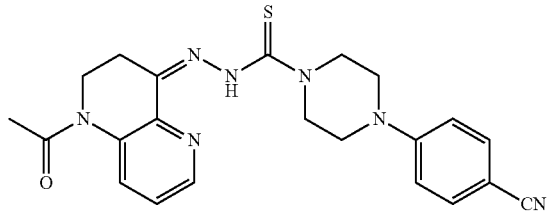
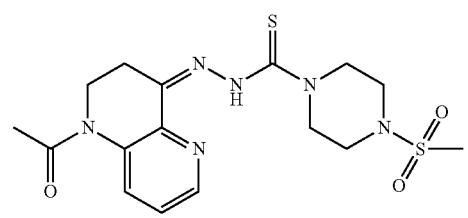 | 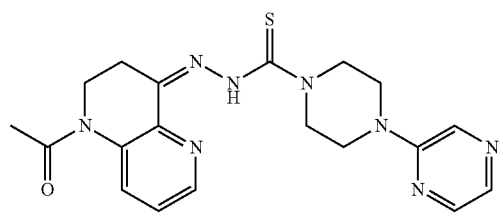
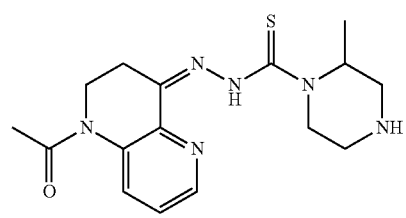 | 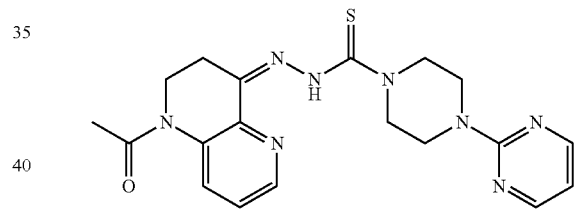
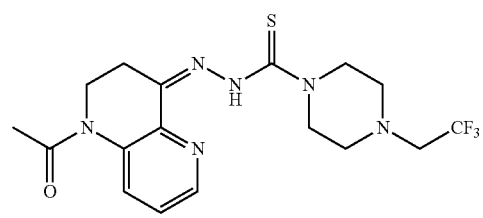 | 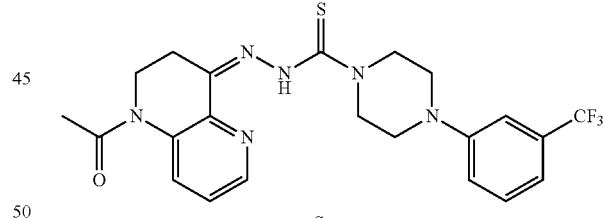
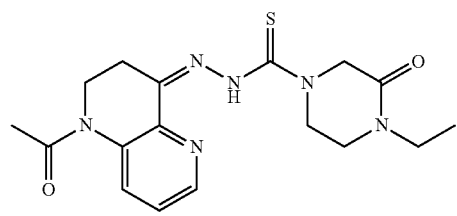 | 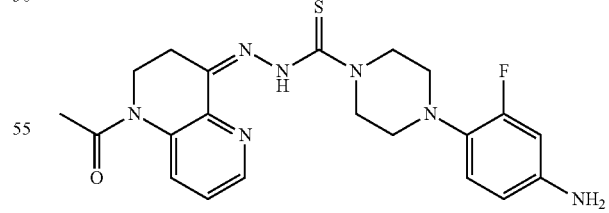
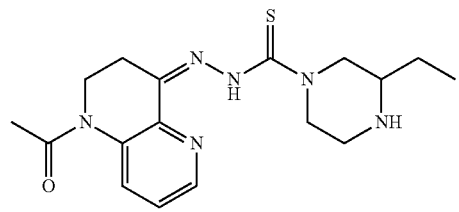 | 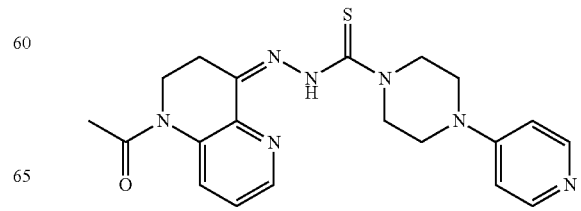

101
-continued
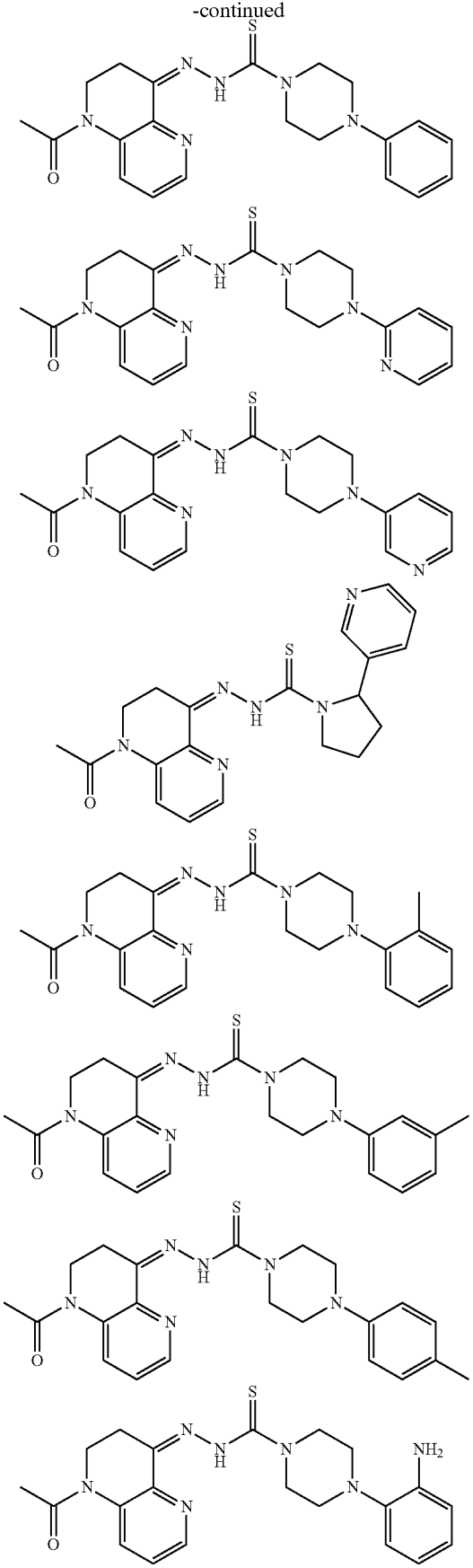
102
-continued
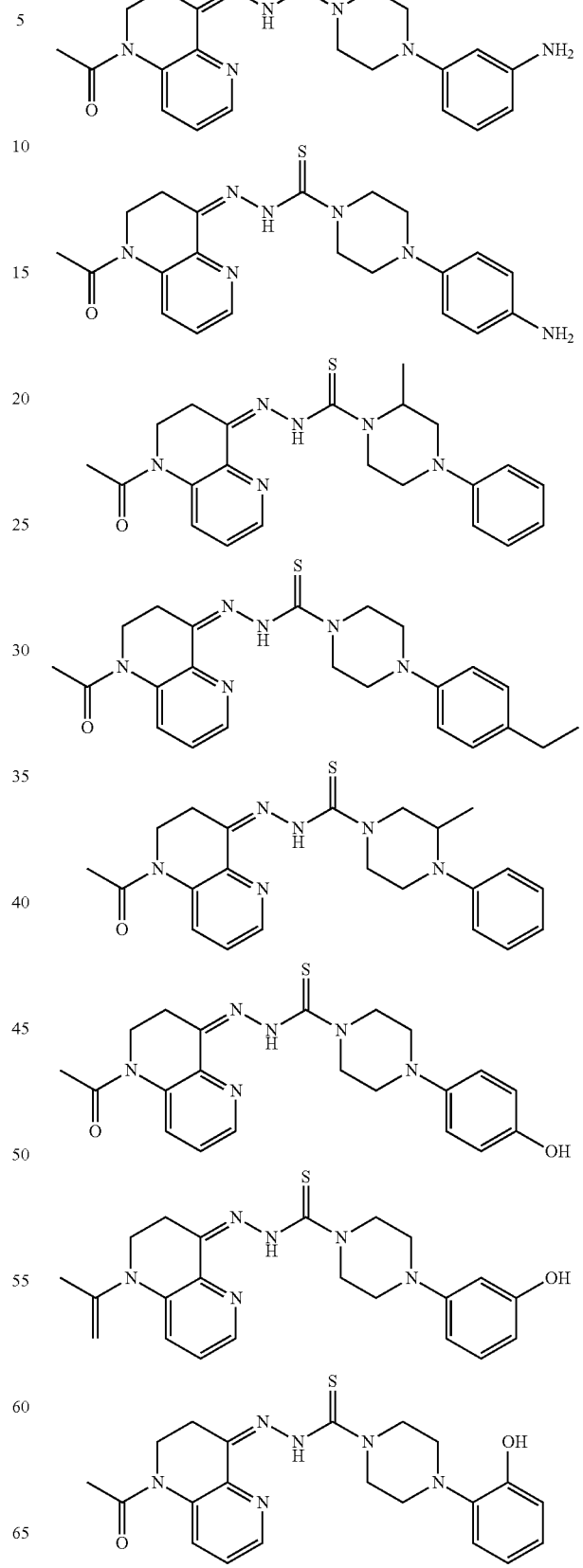

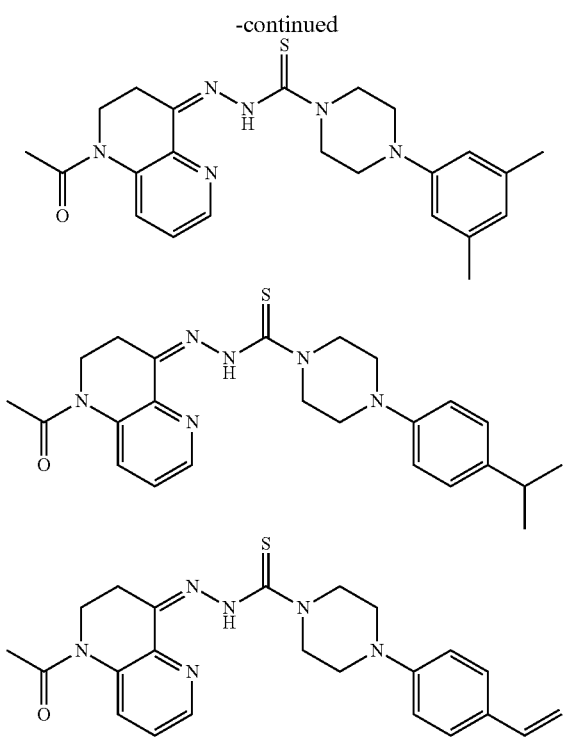

Contemplated Syntheses

Compounds of Formulas Ia-Ih may be synthesized by synthetic routes described herein. In certain embodiments, processes well-known in the chemical arts can be used, in addition to, or in light of, the description contained herein. Starting materials are generally available from commercial sources such as Aldrich Chemicals (Milwaukee, Wis.) or are readily prepared using methods well known to those skilled in the art.

Libraries of compounds of Formulas Ia-Ih may be prepared by a combinatorial 'split and mix' approach or by multiple parallel syntheses using either solution phase or solid phase chemistry, by procedures known to those skilled in the art. Thus according to a further aspect of the inventive subject matter, there is provided a compound library comprising at least 2 compounds of Formulas Ia-Ih, enantiomers, diastereomers or pharmaceutically acceptable salts thereof.

In the preparation of compounds of the present inventive subject matter, protection of various groups (e.g., primary or secondary amine) of intermediates may be necessary. The need for such protection will vary depending on the nature of the remote functionality and the conditions of the preparation methods. For example, sitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The use and need for such protection is readily determined by one skilled in the art.

Thiosemicarbazone derivative compounds of Formula (I) and Ia-Ih can be synthesized from commercially available precursors using established protocols. By way of example, a synthetic route similar to that shown in any of the following schemes may be used, together with synthetic methods known in the art of synthetic organic chemistry, or variations thereon as appreciated by those skilled in the art. Each variable in the following schemes refers to any group consistent with the description of the compounds provided herein.

For illustrative purposes, reaction Schemes A-B depicted below provide routes for synthesizing the compounds of Formulas Ia-Ih, as well as key intermediates. For a more detailed description of the individual reaction steps, see the Examples section below. Those skilled in the art will appreciate that other synthetic routes may be available and used. Although specific starting materials and reagents are depicted in the schemes and discussed below, other starting materials and reagents may be available for substitution to provide a variety of derivatives and/or reaction conditions. In addition, many of the compounds prepared by the methods described below can be further modified in light of this disclosure using conventional chemistry well known to those skilled in the art.

Synthetic procedures deemed to be useful for preparing the thiosemicarbazone derivatives contemplated herein may also be taken from various published sources, including Journal of Medicinal Chemistry (2004), 47(12), 3212-3219; Bioorganic & Medicinal Chemistry Letters (2013), 23(11), 3304-3307; Medicinal Chemistry Research (2013), 22(6), 2802-2808; WO 2009/079797, WO 2008/083491, CN 1224005, or CN 103058995.

One exemplary synthetic scheme is depicted below as Scheme A, where condensation of ketone 1 with semicarbazide 2 in ethanol at reflux temperature provided the designed thiosemicarbazone derivatives I.

Scheme A

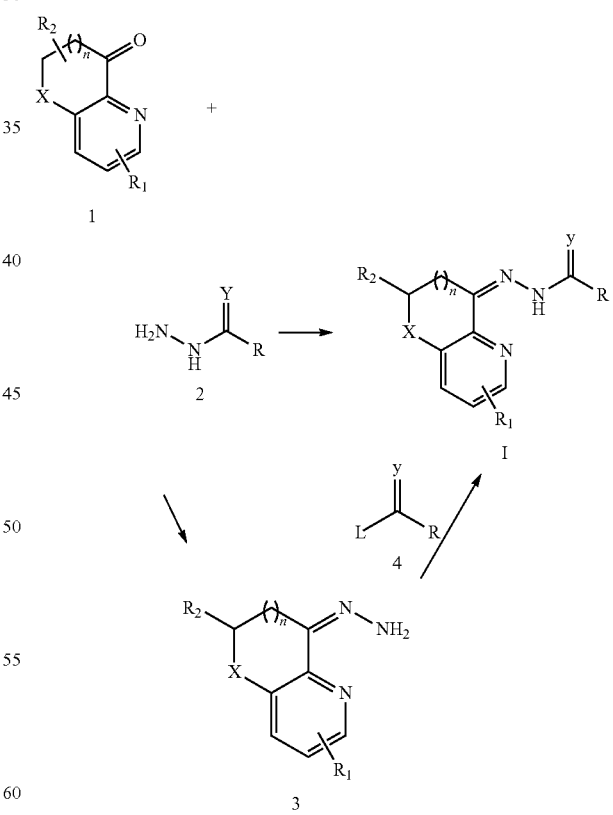

Alternatively, treatment of ketone 1 with hydrazine produced hydrazone 3, which can generate the final product I when reacted with intermediate 4, wherein L could be either methylthio or imidazoyl or other leaving substituents (e.g., *Journal of Medicinal Chemistry* (1979), 22(11), 1367-1373.

*American Chemical Science Journal*, 3(3), 203-220; 2013; *Organometallics*, 28(13), 3916-3921; 2009)

General methods to make intermediates I are described (e.g., WO 2014/025651) in Scheme B. The reaction of commercially available bromopyridine 5 with related the bromide 6 in the present of the catalyst in anhydrous solvent, such as THF, produced intermediate 7. When X is O, the diethyl azodicarboxylate and PPh$_3$ were used as catalysts; while X is NR$_7$, the reactions were carried out in the presence of a base, such as NaH, in DMF. The reaction mixture can be carried out in the 0-100° C., and reaction progress was monitored by TLC or HPLC.

Scheme B

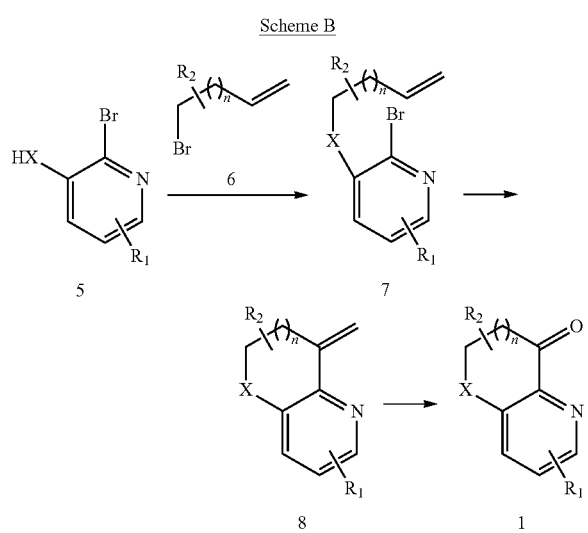

The cyclization of 7 gave pyridyl alkene 8 in the presence of PPh$_3$, Pd(OAc)$_2$, KOAc and tetraethyl ammonium chloride hydrate in DMF under argon atmosphere. The flask was purged with argon and then the resulting reaction mixture was stirred at 80-150° C. for 10-20 h. The desired product 1 was obtained when 7 was treated with O$_3$ in a mixture of solvents, such as MeOH:CHCl$_3$, and a catalytic amount of NaHCO$_3$ at −78° C.

Alternatively, the conversion of intermediate 8 to 1 can be performed by two step procedure: first treatment of pyridyl alkene 8 provided diol in the presence of NMO and catalytic osmium tetraoxide in dichloromethane, then diol gave the desired ketone 1 when it reacted with sodium periodate in the mixture of THF and H2O (see e.g., WO2010033495).

The intermediate 2 can be prepared with the known reported methodologies (see e.g., *Journal of Medicinal Chemistry* (2004), 47(12), 3212-3219; *Bioorganic & Medicinal Chemistry Letters* (2013), 23(11), 3304-3307; *Medicinal Chemistry Research* (2013), 22(6), 2802-2808; WO 2009/079797; WO 2008/083491; CN 1224005, or CN 103058995).

Contemplated Formulations

The inventive subject matter is also drawn to therapeutic compositions comprising one or more of contemplated compounds as active ingredient in further combination with a pharmaceutically-acceptable carrier. Most typically, such compositions are formulated for administration to a mammalian subject using any suitable route.

The amount of therapeutically active compound that is administered and the dosage regimen for treating a disease condition with the compounds and/or compositions of this inventive subject matter depends on a variety of factors, including the age, weight, sex and medical condition of the subject, the severity of the disease, the route and frequency of administration, and the particular compound employed, and thus may vary widely. However, especially suitable quantities are provided above, and may therefore allow for a daily dose of about 0.001 (or even less) to 100 mg/kg body weight, preferably between about 0.01 and about 50 mg/kg body weight and most preferably from about 0.1 to 20 mg/kg body weight. Typically, a daily dose can be administered in one to four doses per day.

Depending on the particular use and structure, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro will generally be between 0.1 nM and 500 microM, more typically between 50 nM and 400 microM, and most typically between 100 nM and 200 microM.

As already noted above, contemplated compounds may be provided as substantially pure compound or as a salt thereof, and pharmaceutically acceptable salts of the compounds include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the inventive subject matter and their pharmaceutically acceptable acid addition salts.

Salts derived from appropriate bases include alkali metal (e.g., sodium and potassium), alkaline earth metal (e.g., magnesium), ammonium and N+(C$_{1-4}$ alkyl)$_4$ salts. This inventive subject matter also envisions the quaternization of any basic nitrogen-containing groups of the compounds disclosed herein. Water or oil-soluble or dispersible products may be obtained by such quaternization.

Contemplated compositions may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

For example, contemplated pharmaceutically acceptable compositions may be orally administered in any orally acceptable dosage form including capsules, tablets, troches, elixirs, suspensions, syrups, wafers, chewing gums, aqueous suspensions or solutions. Oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration or irradiation (e.g., gamma or e-beam), may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Alternatively, the pharmaceutically acceptable compositions of this inventive subject matter may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this inventive subject matter may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this inventive subject matter include mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this inventive subject matter may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this inventive subject matter are formulated for oral administration.

In accordance with the inventive subject matter, the compounds presented herein may be used to treat diseases associated with cellular proliferation or hyperproliferation, such as cancers including tumors of the nasal cavity, paranasal sinuses, nasopharynx, oral cavity, oropharynx, larynx, hypopharynx, salivary glands, and paragangliomas. The compounds of the inventive subject matter may also be used to treat cancers of the liver and biliary tree (particularly hepatocellular carcinoma), intestinal cancers, particularly colorectal cancer, ovarian cancer, skin cancer, pancreatic cancer, gastric cancer, small cell and non-small cell lung cancer, breast cancer, sarcomas (including fibrosarcoma, malignant fibrous histiocytoma, embryonal rhabdomyosarcoma, leiomysosarcoma, neuro-fibrosarcoma, osteosarcoma, synovial sarcoma, liposarcoma, and alveolar soft part sarcoma), neoplasms of the central nervous systems (particularly brain cancer), and lymphomas (including Hodgkin's lymphoma, lymphoplasmacytoid lymphoma, follicular lymphoma, mucosa-associated lymphoid tissue lymphoma, mantle cell lymphoma, β-lineage large cell lymphoma, Burkitt's lymphoma, and T-cell anaplastic large cell lymphoma).

The compounds and methods of the present inventive subject matter, either when administered alone or in combination with other agents (e.g., chemotherapeutic agents or protein therapeutic agents described below) are also deemed useful in treating a variety of disorders, including for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), pleural effusions, rheumatoid arthritis, diabetic retinopathy, retinitis pigmentosa, and retinopathies, including diabetic retinopathy and retinopathy of prematurity, inflammatory diseases, restenosis, asthma, acute or adult respiratory distress syndrome (ARDS), lupus, vascular leakage, protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kinases such as Src-family kinases are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemialreperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic sclerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener s granulomatosis, and Behcet's disease; scleroderma; preeclampsia; thalassemia; Kaposi's sarcoma; von Hippel Lindau disease; and the like.

In accordance with the inventive subject matter, the compounds presented herein may be used to treat diseases associated with undesired cellular proliferation or hyperproliferation comprising identifying the mammal afflicted with said disease or condition and administering to said afflicted mammal a composition comprising the compound of formula I, wherein the disease or condition is associated with a kinase.

The inventive subject matter also provides methods of treating a mammal afflicted with the above diseases and conditions. The amount of the compounds presented herein may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

In one aspect, contemplated compounds are administered in combination with chemotherapeutic agent, an anti-inflammatory agent, antihistamines, chemotherapeutic agent, immunomodulator, therapeutic antibody or a protein kinase inhibitor, e.g., a tyrosine kinase inhibitor, to a subject in need of such treatment.

Examples of chemotherapeutic agents include NSAIDs; hormones such as glucocorticoids; corticosteroids such as hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydro cortisone-17-butyrate, hydrocortisone-17-valerate, aclometas one dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomide, methotrexate (MTX), minocycline, sulfasalazine, cyclophosphamide, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), monoclonal antibodies against B cells such as rituximab (RITUXAN®), T cell costimulation blockers such as abatacept (Orencia), Interleukin 6 (IL-6) blockers such as tocilizumab; hormone antagonists, such as tamoxifen, finasteride or LHRH antagonists; radioactive isotopes (e.g., At211, I131, I125 Y90, Re186, Re188, Sm153, Bi212, P32, Pb212 and radioactive isotopes of Lu); miscellaneous investigational agents such as thioplatin, PS-341, phenylbutyrate, ET-18-OCH3, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma 1I and calicheamicin omega1I (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamiein; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as fenretinide, retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®)); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Additional chemotherapeutic agents as defined herein include "anti-hormonal agents" or "endocrine therapeutics" which act to regulate, reduce, block, or inhibit the effects of hormones that can promote the growth of cancer. They may be hormones themselves, including: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMI-DEX®), letrozole (FEMARA®) and aminoglutethimide, and other aromatase inhibitors include vorozole (RIVI-SOR®), megestrol acetate (MEGASE®), fadrozole, and 4(5)-imidazoles; lutenizing hormone-releasing hormone agonists, including leuprolide (LUPRON® and ELI-GARD®), goserelin, buserelin, and tripterelin; sex steroids, including progestins such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide.

Additional chemotherapeutic agents include therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), lebrikizumab, tocilizumab (ACTEMRA®, Roche), tositumomab (Bexxar, Corixia), and the antibody drug conjugate, gemtuzumab ozogamicin (MYLOTARG®, Wyeth). Additional humanized monoclonal antibodies with therapeutic potential as agents in combination with contemplated compounds include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, paseolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1 λ antibody genetically modified to recognize interleukin-12 p40 protein.

The examples of kinase inhibitors include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); 1MC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSAJ) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N-8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluoro-phenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6 [5 [[[2-methylsulfonyl)ethyl]amino]methyl]-2-furanyl]-4-quinazolinamine)

Other example of kinase inhibitors includs HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVECJ, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521;

Isis/Lilly); imatinib mesylate (GLEEVECJ); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

When other therapeutic agents are employed in combination with the compounds of the present inventive subject matter, they may be used for example in amounts as noted in the Physician Desk Reference (PDR) or as otherwise determined by one having ordinary skill in the art.

EXAMPLES

The following examples are provided to further illustrate the present inventive subject matter but, of course, should not be construed as in any way limiting its scope.

All experiments were performed under anhydrous conditions (i.e., dry solvents) in an atmosphere of argon, except where stated, using oven-dried apparatus and employing standard techniques in handling air-sensitive materials. Aqueous solutions of sodium bicarbonate (NaHHCO$_3$) and sodium chloride (brine) were saturated.

Analytical thin layer chromatography (TLC) was carried out on Merck Kiesel gel 60 F254 plates with visualization using ultraviolet light and/or anisaldehyde, potassium permanganate, or phosphomolybdic acid dips.

NMR spectra: 1H Nuclear magnetic resonance spectra were recorded at 400 MHz. Data are presented as follows: chemical shift, multiplicity (s=singlet, d=doublet, t=triplet, q=quartet, qn=quintet, dd=doublet of doublets, m=multiplet, bs— broad singlet), coupling constant (J/Hz) and integration. Coupling constants were taken and calculated directly from the spectra and are uncorrected.

Low resolution mass spectra: Electrospray (ES+) ionization was used. The protonated parent ion (M+H) or parent sodium ion (M+Na) or fragment of highest mass is quoted. Analytical gradient consisted of 10% ACN in water ramping up to 100% ACN over 5 minutes unless otherwise stated.

High performance liquid chromatography (HPLC) was use to analyze the purity of derivatives. HPLC was performed on a Phenomenex Synergi Polar-RP, 4 u, 80 A, 150×4.6 mm column using a Shimadzu system equipted with SPD-M10A Phosphodiode Array Detector. Mobile phase A was water and mobile phase B was acetonitrile with a gradient from 20% to 80% B over 60 minutes and re-equilibrate at A/B (80:20) for 10 minutes. UV detection was at 220 and 54 nm.

Preparation of Exemplary Intermediates
Intermediate 1: 2H-pyrano[3,2-b]pyridin-4(3H)-one

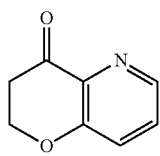 [SMILES: O=C1CCOc2cccnc21]

Step 1. 2-bromo-3-(but-3-en-1-yloxy)pyridine. Diethyl azodicarboxylate (95 mL, 0.6 mol) was added dropwise to a stirred mixture of 2-bromo-3-hydroxypyridine (97 g, 0.55 mol), 3-buten-1-ol (47.7 mL, 0.55 mol), and PPh3 (175.3 g, 0.66 mol) in THF (970 mL) at 0° C. under a N2 atmosphere. The reaction mixture was warmed to 50° C. in an oil bath and stirred for 17.5 h. Reaction progress was monitored by TLC (15% EtOAc in hexane, UV active). The reaction mixture was cooled to ambient temperature and diluted with saturated NaHC03 solution (500 mL). The aqueous solution was extracted with EtOAc (1 L). The organic layer was dried over Na2S04 (200 g), and concentrated. The residual product was purified by column chromatography using 60-120 mesh, eluting with 5% EtOAc in hexane to afford the title compound as a pale yellow oil. MS (ESI) m/z: 228 (MH+).

Step 2. 4-methylene-3,4-dihydro-2H-pyrano[3,2-b]pyridine. To a solution of 2-bromo-3-(but-3-en-1-yloxy)pyridine (130 g, 0.567 mol) in DMF (1.3 L), PPh3 (59.5 g, 0.22 mol), Pd(OAc)2 (19.9 g, 85 mol), KOAc (278.25 g, 2.835 mol), and tetraethyl ammonium chloride hydrate (187.9 g, 1.134 mol) were added under argon atmosphere. The flask was purged with argon for 15 min, and then the resulting reaction mixture was stirred at 110° C. for 16 h. Reaction progress was monitored by TLC (10% EtOAc in hexane, UV active). The reaction mixture was diluted with EtOAc and saturated NaHC03 solution. The organic layer was separated and dried over Na2S04 (200 g), and concentrated. The product thus obtained was purified by column chromatography using 60-120 mesh, eluting with 5% EtOAc in hexane to afford the title compound as a pale yellow oil. MS (ESI) m/z: 148 (MH+).

Step 3. 2H-pyrano[3,2-b]pyridin-4(3H)-one. To a solution of 4-methylene-3 dihydro-2H-pyrano[3,2-b]pyridine (175 g, 1.19 mol) in a mixture of solvents (MeOH:CHCl3) was added a catalytic amount of NaHCO3 (1 g). The reaction mixture was cooled to −78° C. and purged with O3. Reaction progress was monitored by TLC (50% EtOAc in hexane, UV active). After 16 h, the reaction mixture was quenched with dimethyl sulfide (50 mL) at −78° C. The resulting mixture was stirred for 12 h at ambient temperature. The reaction mixture was then diluted with EtOAc and water. The organic layer was washed with water (3×500 mL), dried over Na2S04 (200 g), and concentrated under reduced pressure. The residue thus obtained was recrystallized with diethyl ether to give the title compound as a colorless solid MS (ESI) m/z: 150.2 (MH+).

Intermediate 2: 2,3-dihydro-1,5-naphthyridin-4(1H)-one

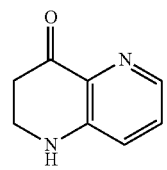 [SMILES: O=C1CCNc2cccnc21]

Step 1. 2-bromo-N-(but-3-en-1-yl)pyridin-3-amine. To a solution of 3-amino-2-bromo-pyridine (1 eq, Apollo Scientific Ltd., CAS#39856-58-1) and DMF (0.2 M) is added 60% NaH (1.2 eq). After stirring at room temperature for 30 minutes, the reaction is treated with 4-bromobut-1-ene (1 eq.). Reaction progress is monitored by TLC until judged complete. The reaction mixture is diluted with water and the aqueous solution is extracted with EtOAc. The organic layer is dried over Na2S04, and concentrated. The product thus obtained is purified by column chromatography to afford the title compound.

Step 2. tert-butyl (2-bromopyridin-3-yl)(but-3-en-1-yl)carbamate. To a solution of 2-bromo-N-(but-3-en-1-yl)pyridin-3-amine (1 eq.) and DCM (0.2 M) is added (Boc)20 (1.5 eq.). The solution is stirred at room temperature until judged complete by TLC. The solution is concentrated in vacuo and purified by column chromatography to give the title compound.

Step 3. tert-butyl 4-methylene-3,4-dihydro-1,5-naphthyridine-1(2H)-carboxylate. To a solution of tert-butyl (2-bromopyridin-3-yl)(but-3-en-1-yl)carbamate (1 eq.) in DMF (0.2 M), PPh3 (0.25 eq.), Pd(OAc)2 (0.1 eq), and KOAc (5 eq.), is added, under an argon atmosphere, tetraethyl ammonium chloride hydrate (2 eq.). The flask is purged with argon for 15 min, and the resulting reaction mixture is stirred at 110° C. for 16 h. The reaction progress is monitored by TLC. The reaction mixture is diluted with EtOAc and saturated NaHC03 solution. The organic layer is separated and dried over Na2S04, and concentrated. The compound that may be thus obtained is purified by column chromatography to afford the title compound.

Step 4. tert-butyl 4-oxo-3,4-dihydro-1,5-naphthyridine-1(2H)-carboxylate.

To a solution of tert-butyl 4-methylene-3,4-dihydro-1,5-naphthyridine-1(2H)-carboxylate (1 eq.) in a mixture of solvents (MeOH:CHCl3) is added a catalytic amount of NaHC03. The reaction mixture is cooled to −78° C. and purged with 03. Reaction progress is monitored by TLC. After the reaction is judged complete, the reaction mixture is quenched with dimethyl sulfide (5 eq.) at −78° C. The resulting mixture is then stirred for 12 h at ambient temperature. The reaction mixture is diluted with EtOAc and water. The organic layer is washed with water, dried over Na2S04, and concentrated in vacuo. The product that may be thus obtained is purified by column chromatography to give the title compound.

Step 5, 2,3-dihydro-1,5-naphthyridin-4(1H)-one. To a solution of tert-butyl 4-oxo-3,4-dihydro-1,5-naphthyridine-1(2H)-carboxylate (1 eq.) and THF (0.2 M) is added 4M HCl in dioxane (5 eq.). The reaction is monitored by TLC. The reaction is diluted with EtOAc and washed with saturated NaHCO3. The organic solution is dried over MgSO4 and concentrated in vacuo. The compound that may be thus obtained is purified by column chromatography to give the title compound.

Intermediate 3: 1-acetyl-2,3-dihydro-1,5-naphthyridin-4(1H)-one

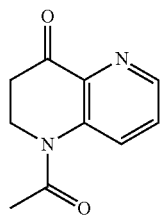

To a solution of 2,3-dihydro-1,5-naphthyridin-4(H)-one (1 eq.) and DCM (0.2 eq.) is added DIPEA (2.2 eq.) and acetyl chloride (1.2 eq.). The reaction is monitored by TLC. The reaction is washed with water, brine, dried over MgSO4, concentrated in vacuo, and purified by column chromatography to give the title compound.

Further intermediates were synthesized from the listed intermediates above in an analogous fashion to Intermediate 1-3, and structures are shown in Table 1.

| Intermediate # | Starting material | Structure | Mass ((MH+)) |
|---|---|---|---|
| 4 | | 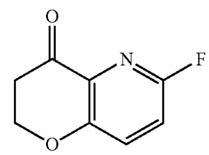 [SMILES: O=C1CCOc2ccc(F)nc21] | 167.04 |
| 5 | | 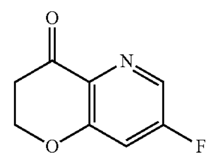 [SMILES: O=C1CCOc2cc(F)cnc21] | 167.04 |
| 6 | | 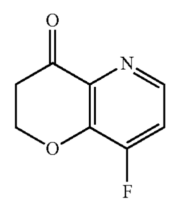 [SMILES: O=C1CCOc2c(F)ccnc21] | 167.04 |
| 7 | | 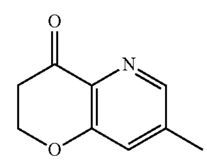 | 163.06 |
| 8 | | 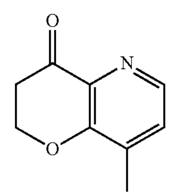 | 163.06 |
| 9 | | 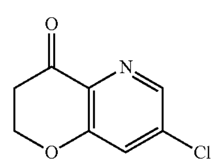 [SMILES: O=C1CCOc2cc(Cl)cnc21] | 183.01 |
| 10 | | 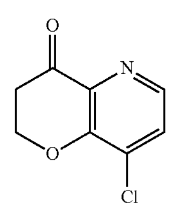 [SMILES: O=C1CCOc2c(Cl)ccnc21] | 183.01 |
| 11 | | 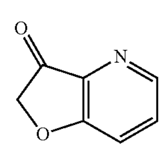 | 135.03 |
| 12 | | 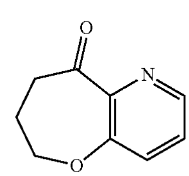 [SMILES: O=C1CCCOc2cccnc21] | 183.06 |

-continued

| Intermediate # | Starting material | Structure | Mass ((MH+)) |
|---|---|---|---|
| 13 | Br, N, H2N (2-bromo-3-aminopyridine) | pyrrolo[3,2-b]pyridin-3(2H)-one | 134.05 |
| 14 | Br, N, H2N | tetrahydro-azepino[3,2-b]pyridin-one | 162.08 |
| 15 | Br, N, F, H2N | 6-fluoro-tetrahydro-1,5-naphthyridin-4-one | 166.05 |
| 16 | Br, N, H2N, F | 7-fluoro-tetrahydro-1,5-naphthyridin-4-one | 166.05 |
| 17 | Br, N, H2N (6-methyl) | 6-methyl-tetrahydro-1,5-naphthyridin-4-one | 162.08 |
| 18 | Br, N, H2N (5-methyl) | 7-methyl-tetrahydro-1,5-naphthyridin-4-one | 162.08 |
| 19 | Br, N, H2N (4-methyl) | 8-methyl-tetrahydro-1,5-naphthyridin-4-one | 162.08 |
| 20 | Br, N, H2N, Cl | 7-chloro-tetrahydro-1,5-naphthyridin-4-one | 162.02 |

-continued

| Intermediate # | Starting material | Structure | Mass ((MH+)) |
|---|---|---|---|
| 21 | Br, N, H2N, Cl | 8-chloro-tetrahydro-1,5-naphthyridin-4-one | 162.02 |
| 22 | tetrahydro-1,5-naphthyridin-4-one | N-methyl tetrahydro-1,5-naphthyridin-4-one | 162.08 |

Exemplary Compounds

Example 1

(Z)-4-methyl-N'-(2H-pyrano[3,2-b]pyridin-4(3H)-ylidene)piperazine-1-carbothiohydrazide

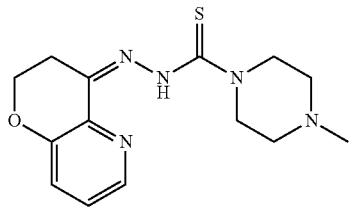

(1)

Method A: (Z)-4-methyl-N'-(2H-pyrano[3,2-b]pyridin-4(3H)-ylidene)piperazine-1-carbothiohydrazide can prepared with a method reported elsewhere (*ACS Medicinal Chemistry Letters*, 5(4), 336-339; 2014). Briefly, thiosemicarbazones was synthesized by reacting 2H-pyrano[3,2-b]pyridin-4(3H)-one (Intermediate 1) and 4-methylpiperazine-1-carbothiohydrazide under microwave irradiation. Equimolar quantities of the 2H-pyrano[3,2-b]pyridin-4(3H)-one (1.0 mmol) and 4-methylpiperazine-1-carbothiohydrazide (1.0 mmol) were dissolved in 8 mL of EtOH with the addition of 0.2 mL of acetic acid as the catalyst. The resulting mixture was heated in a microwave reactor at 90° C./30 min (max. microwave power 50 W). After cooling, the precipitated solid was filtered and washed with ether. The final product was purified by crystallization (ethanol) or column chromatography on silica gel to provide (Z)-4-methyl-N'-(2H-pyrano[3,2-b]pyridin-4(3H)-ylidene)piperazine-1-carbothiohydrazide. MS (ESI) m/z: 306.1 (MH+).

Method B: (Z)-4-methyl-N'-(2H-pyrano[3,2-b]pyridin-4(3H)-ylidene)piperazine-1-carbothiohydrazide can prepared with a method reported elsewhere (WO 2008/083491).

Briefly, 4-methylpiperazine-1-carbothiohydrazide (1.0 mmol, 1 eq) and 2H-pyrano[3,2-b]pyridin-4(3H)-one (Intermediate 1, 1.0 mmol) was dissolved in 15 ml of ethanol at room temperature, in the presence of 1% glacial acetic acid (0.15 ml, 2.6 mmol). The mixture was stirred under reflux for 10 hours. After concentration, the crude thus obtained was taken up in dichloromethane, washed with a potassium carbonate aqueous solution then with water. The organic layer was dried over sodium sulfate, filtered and concentrated. The crude was purified by ISCO column chromatography on silica gel to provide (Z)-4-methyl-N'-(2H-pyrano[3,2-b]pyridin-4(3H)-ylidene)piperazine-1-carbothiohydrazide. MS (ESI) m/z: 306.1 (MH+).

Example 2

(Z)-2-(2H-pyrano[3,2-b]pyridin-4(3H)-ylidene)hydrazinecarbothioamide

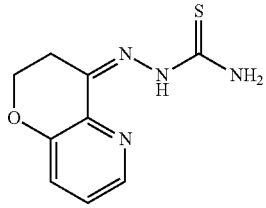 [SMILES: NC(=S)N/N=C1/CCOc2cccnc21]

(Z)-2-(2H-pyrano[3,2-b]pyridin-4(3H)-ylidene)hydrazinecarbothioamide was prepared with Method B: 2H-pyrano[3,2-b]pyridin-4(3H)-one (Intermediate 1, 1.0 mmol) and hydrazinecarbothioamide (1.0 mmol, 1 eq) was dissolved in 15 ml of ethanol at room temperature, in the presence of 1% glacial acetic acid (0.15 ml, 2.6 mmol). The mixture was stirred under reflux for 10 hours. After concentration, the crude thus obtained was taken up in dichloromethane, washed with a potassium carbonate aqueous solution then with water. The organic layer was dried over sodium sulfate, filtered and concentrated. The crude was purified by ISCO column chromatography on silica gel to provide (Z)-2-(2H-pyrano[3,2-b]pyridin-4(3H)-ylidene)hydrazinecarbothioamide. MS (ESI) m/z: 223.06 (MH+).

Example 3

(Z)—N'-(2H-pyrano[3,2-b]pyridin-4(3H)-ylidene)-4-(pyridin-2-yl)piperazine-1-carbothiohydrazide

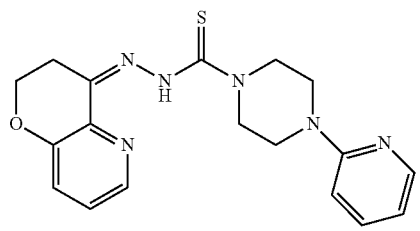 [SMILES: S=C(N/N=C1/CCOc2cccnc21)N1CCN(c2ccccn2)CC1]

Equimolar quantities of the 2H-pyrano[3,2-b]pyridin-4(3H)-one (1.0 mmol) and 4-(pyridin-2-yl)piperazine-1-carbothiohydrazide (*Phosphorus, Sulfur and Silicon and the Related Elements*, 180(12), 2653-2666; 2005; WO 2008/083491; *Bioorganic & Medicinal Chemistry Letters*, 24(2), 458-461; 2014) (1.0 mmol) were dissolved in 8 mL of EtOH with the addition of 0.2 mL of acetic acid as the catalyst. The resulting mixture was heated in a microwave reactor at 90° C./30 min (max. microwave power 50 W). After cooling, the precipitated solid was filtered and washed with ether. The final product was purified by ISCO column chromatography on silica gel to provide (Z)—N'-(2H-pyrano[3,2-b]pyridin-4(3H)-ylidene)-4-(pyridin-2-yl)piperazine-1-carbothiohydrazide. MS (ESI) m/z: 369.1 (MH+).

Example 4

(Z)—N'-(2H-pyrano[3,2-b]pyridin-4(3H)-ylidene)benzothiohydrazide

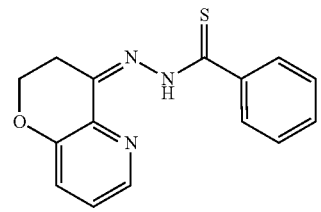

2H-pyrano[3,2-b]pyridin-4(3H)-one (Intermediate 1, 1.0 mmol) and benzothiohydrazide (*Bioorganic & Medicinal Chemistry Letters*, 23(11), 3304-3307; WO 2013/033392; *Journal of Medicinal Chemistry*, 50(24), 6212-6225; 2007) (1.0 mmol, 1 eq) was dissolved in 15 ml of ethanol at room temperature, in the presence of 1% glacial acetic acid (0.15 ml, 2.6 mmol). The mixture was stirred under reflux for 10 hours. After concentration, the crude thus obtained was taken up in dichloromethane, washed with a potassium carbonate aqueous solution then with water. The organic layer was dried over sodium sulfate, filtered and concentrated. The crude was purified by ISCO column chromatography on silica gel to provide (Z)—N'-(2H-pyrano[3,2-b]pyridin-4(3H)-ylidene)benzothiohydrazide. MS (ESI) m/z: 284.1 (MH+).

Further exemplary compounds were prepared following the general procedures described above from commercial or known starting materials and are listed in Table 2 below.

| Example number | Structure | Mass (MH+) |
|---|---|---|
| 5 | 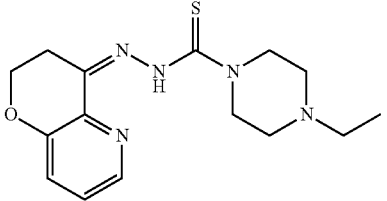 [SMILES: CCN1CCN(C(=S)N/N=C2/CCOc3cccnc32)CC1] | 320.02 |
| 6 | 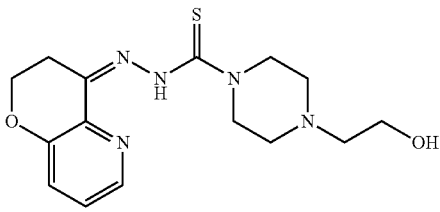 [SMILES: OCCN1CCN(C(=S)N/N=C2/CCOc3cccnc32)CC1] | 336.14 |
| 7 | 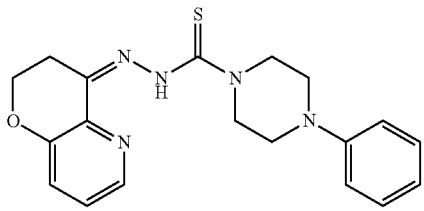 [SMILES: S=C(N/N=C1/CCOc2cccnc21)N1CCN(c2ccccc2)CC1] | 368.15 |
| 8 | 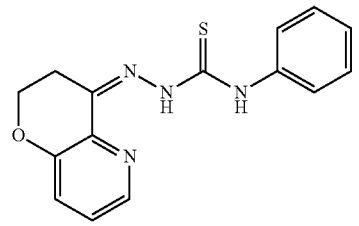 [SMILES: S=C(N/N=C1/CCOc2cccnc21)Nc1ccccc1] | 299.09 |
| 9 | 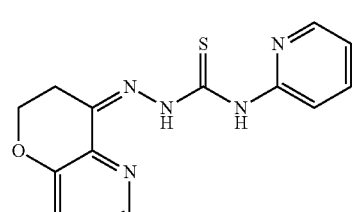 | 300.08 |
| 10 | 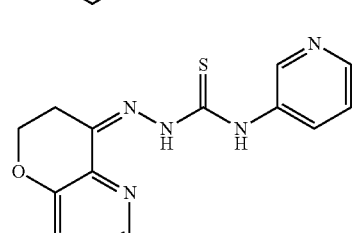 | 300.08 |
| 11 | 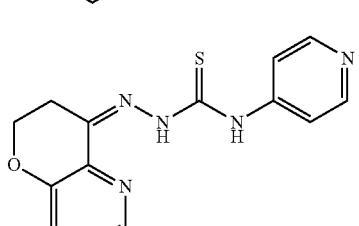 | 300.08 |

-continued

| Example number | Structure | Mass (MH+) |
|---|---|---|
| 12 | 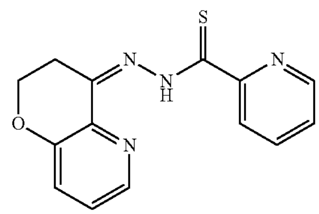 [SMILES: S=C(N/N=C1/CCOc2cccnc21)c1ccccn1] | 285.07 |
| 13 | 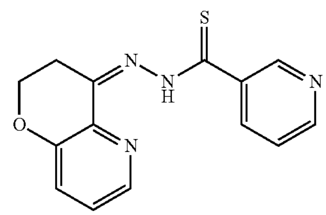 [SMILES: S=C(N/N=C1/CCOc2cccnc21)c1cccnc1] | 285.07 |
| 14 | 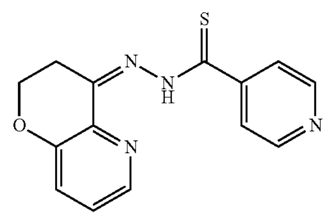 [SMILES: S=C(N/N=C1/CCOc2cccnc21)c1ccncc1] | 285.07 |
| 15 | 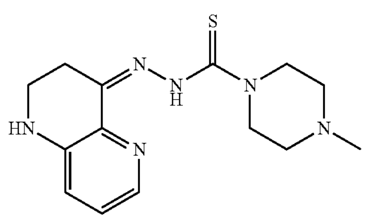 [SMILES: CN1CCN(C(=S)N/N=C2/CCNc3cccnc32)CC1] | 305.15 |
| 16 | 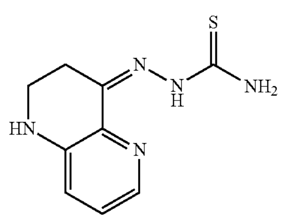 [SMILES: NC(=S)N/N=C1/CCNc2cccnc21] | 222.07 |
| 17 | 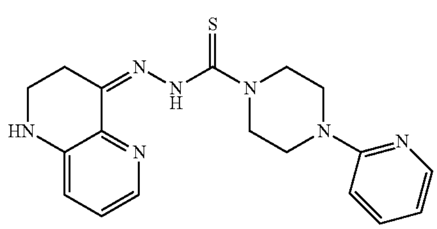 [SMILES: S=C(N/N=C1/CCNc2cccnc21)N1CCN(c2ccccn2)CC1] | 368.16 |
| 18 | 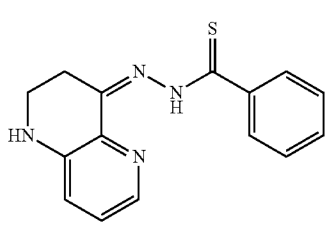 [SMILES: S=C(N/N=C1/CCNc2cccnc21)c1ccccc1] | 283.09 |

-continued
| Example number | Structure | Mass (MH+) |
|---|---|---|
| 19 | 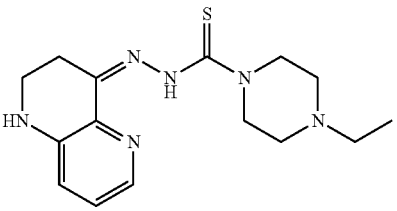 [SMILES: CCN1CCN(C(=S)N/N=C2/CCNc3cccnc32)CC1] | 319.16 |
| 20 | 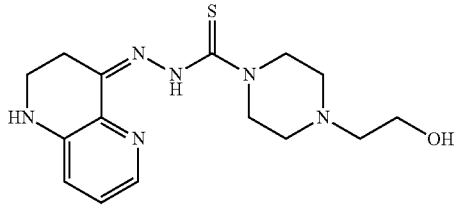 [SMILES: OCCN1CCN(C(=S)N/N=C2/CCNc3cccnc32)CC1] | 335.16 |
| 21 | 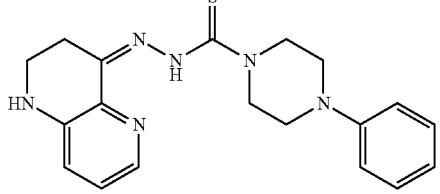 | 367.16 |
| 22 | 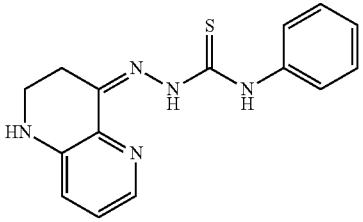 [SMILES: S=C(N/N=C1/CCNc2cccnc21)Nc1ccccc1] | 398.10 |
| 23 | 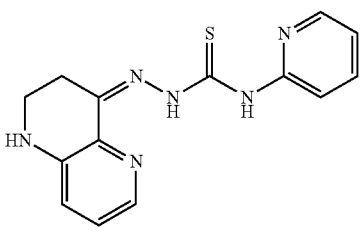 [SMILES: S=C(N/N=C1/CCNc2cccnc21)Nc1ccccn1] | 399.10 |
| 24 | 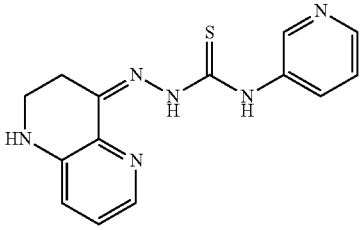 [SMILES: S=C(N/N=C1/CCNc2cccnc21)Nc1cccnc1] | 399.10 |

-continued

| Example number | Structure | Mass (MH+) |
|---|---|---|
| 25 | 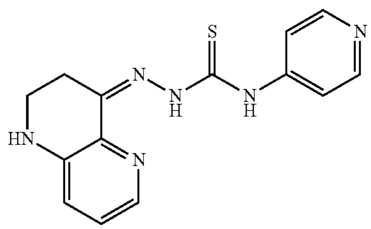 [SMILES: S=C(N/N=C1/CCNc2cccnc21)Nc1ccncc1] | 399.10 |
| 26 | 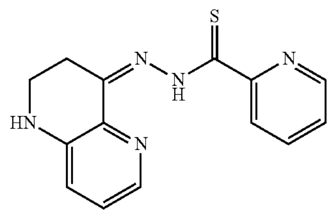 [SMILES: S=C(N/N=C1/CCNc2cccnc21)c1ccccn1] | 284.09 |
| 27 | 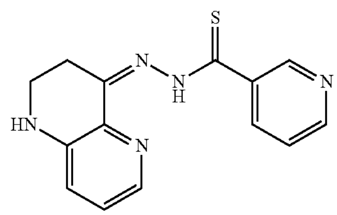 [SMILES: S=C(N/N=C1/CCNc2cccnc21)c1cccnc1] | 284.09 |
| 28 | 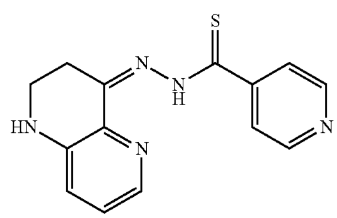 [SMILES: S=C(N/N=C1/CCNc2cccnc21)c1ccncc1] | 284.09 |
| 29 | 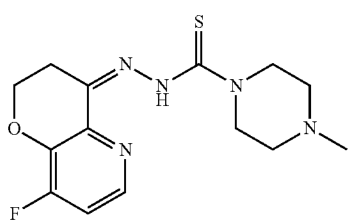 [SMILES: CN1CCN(C(=S)N/N=C2/CCOc3c(F)ccnc32)CC1] | 324.12 |
| 30 | 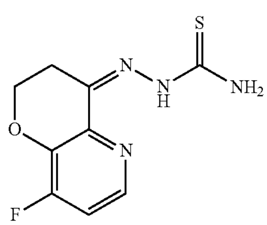 [SMILES: NC(=S)N/N=C1/CCOc2c(F)ccnc21] | 241.05 |
| 31 | 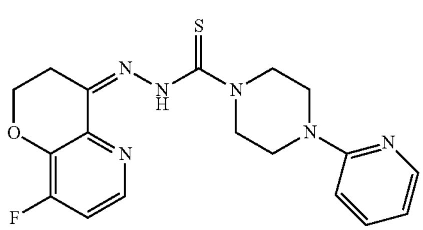 | 387.13 |

-continued

| Example number | Structure | Mass (MH+) |
|---|---|---|
| 32 | 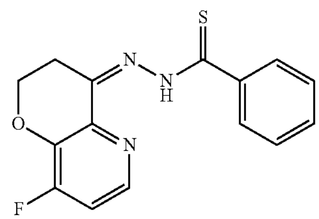 [SMILES: Fc1ccnc2c1OCC/C2=N/NC(=S)c1ccccc1] | 302.07 |
| 33 | 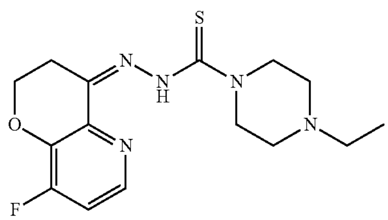 [SMILES: CCN1CCN(C(=S)N/N=C2/CCOc3c(F)ccnc32)CC1] | 338.14 |
| 34 | 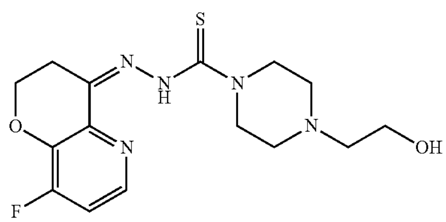 [SMILES: OCCN1CCN(C(=S)N/N=C2/CCOc3c(F)ccnc32)CC1] | 354.13 |
| 35 | 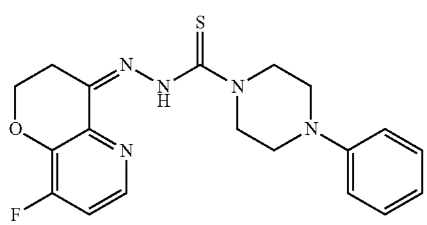 [SMILES: Fc1ccnc2c1OCC/C2=N/NC(=S)N1CCN(c2ccccc2)CC1] | 386.14 |
| 36 | 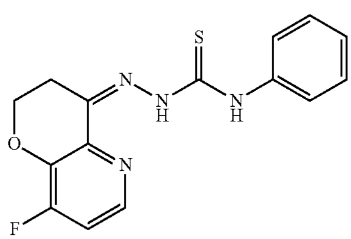 [SMILES: Fc1ccnc2c1OCC/C2=N/NC(=S)Nc1ccccc1] | 317.08 |
| 37 | 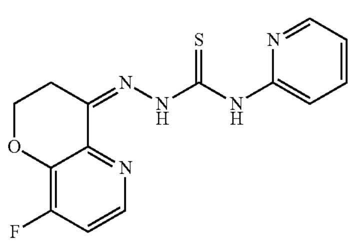 [SMILES: Fc1ccnc2c1OCC/C2=N/NC(=S)Nc1ccccn1] | 318.07 |

| Example number | Structure | Mass (MH+) |
|---|---|---|
| 38 | 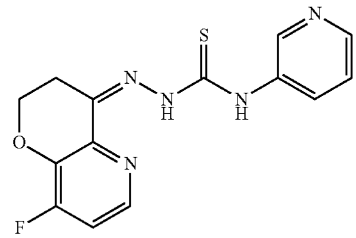 [SMILES: Fc1ccnc2c1OCC/C2=N/NC(=S)Nc1cccnc1] | 318.07 |
| 39 | 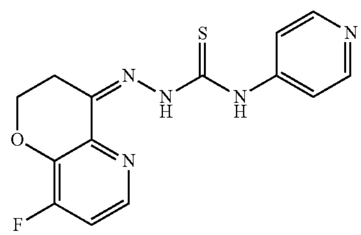 [SMILES: Fc1ccnc2c1OCC/C2=N/NC(=S)Nc1ccncc1] | 318.07 |
| 40 | 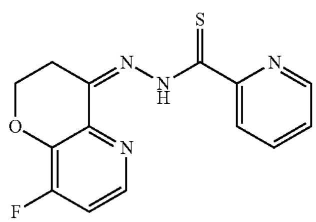 [SMILES: Fc1ccnc2c1OCC/C2=N/NC(=S)c1ccccn1] | 303.06 |
| 41 | 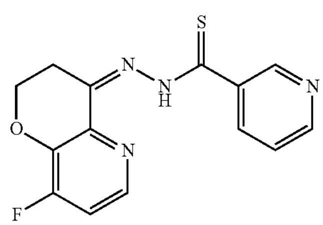 [SMILES: Fc1ccnc2c1OCC/C2=N/NC(=S)c1cccnc1] | 303.06 |
| 42 | 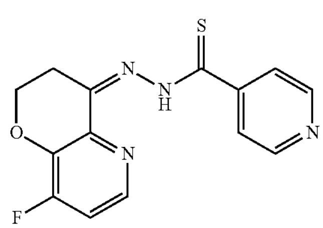 [SMILES: Fc1ccnc2c1OCC/C2=N/NC(=S)c1ccncc1] | 303.06 |
| 43 | 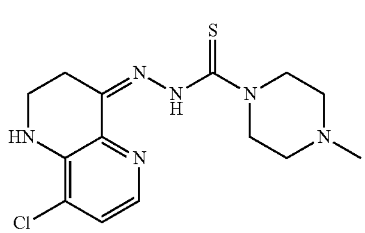 [SMILES: CN1CCN(C(=S)N/N=C2/CCNc3c(Cl)ccnc32)CC1] | 324.12 |

-continued

| Example number | Structure | Mass (MH⁺) |
|---|---|---|
| 44 | 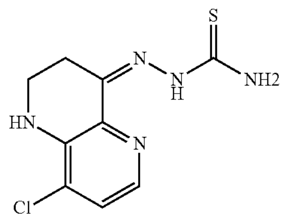 [SMILES: NC(=S)N/N=C1/CCNc2c(Cl)ccnc21] | 256.03 |
| 45 | 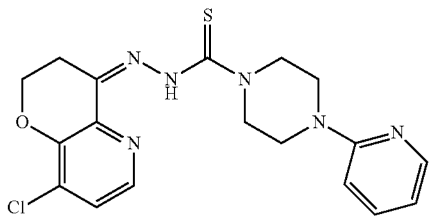 [SMILES: S=C(N/N=C1/CCOc2c(Cl)ccnc21)N1CCN(c2ccccn2)CC1] | 402.12 |
| 46 | 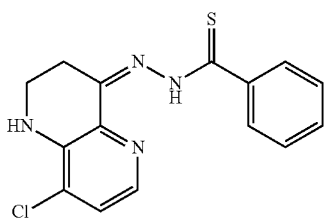 [SMILES: S=C(N/N=C1/CCNc2c(Cl)ccnc21)c1ccccc1] | 317.05 |
| 47 | 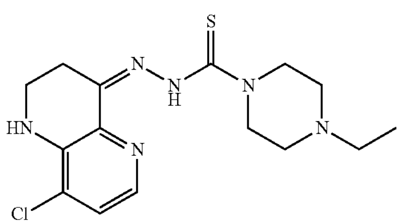 [SMILES: CCN1CCN(C(=S)N/N=C2/CCNc3c(Cl)ccnc32)CC1] | 352.12 |
| 48 | 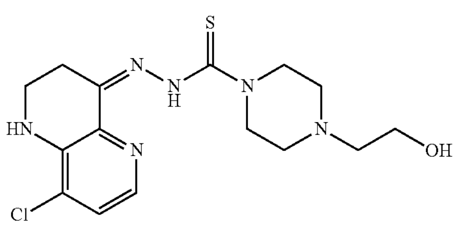 [SMILES: OCCN1CCN(C(=S)N/N=C2/CCNc3c(Cl)ccnc32)CC1] | 369.12 |
| 49 | 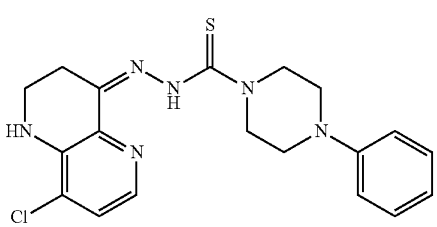 [SMILES: S=C(N/N=C1/CCNc2c(Cl)ccnc21)N1CCN(c2ccccc2)CC1] | 401.12 |
| 50 | 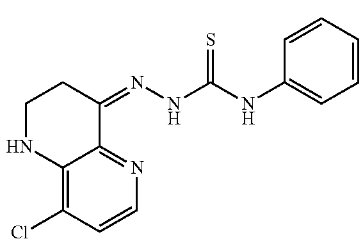 [SMILES: S=C(N/N=C1/CCNc2c(Cl)ccnc21)Nc1ccccc1] | 332.07 |

| Example number | Structure | Mass (MH+) |
|---|---|---|
| 51 | 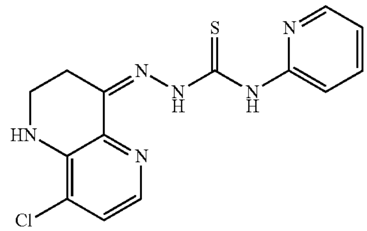 [SMILES: S=C(N/N=C1/CCNc2c(Cl)ccnc21)Nc1ccccn1] | 333.07 |
| 52 | 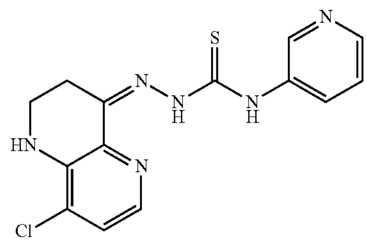 [SMILES: S=C(N/N=C1/CCNc2c(Cl)ccnc21)Nc1cccnc1] | 333.07 |
| 53 | 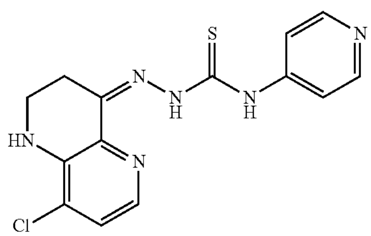 [SMILES: S=C(N/N=C1/CCNc2c(Cl)ccnc21)Nc1ccncc1] | 333.07 |
| 54 | 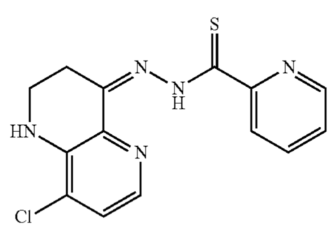 [SMILES: S=C(N/N=C1/CCNc2c(Cl)ccnc21)c1ccccn1] | 318.05 |
| 55 | 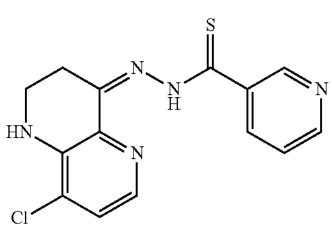 [SMILES: S=C(N/N=C1/CCNc2c(Cl)ccnc21)c1cccnc1] | 318.05 |
| 56 | 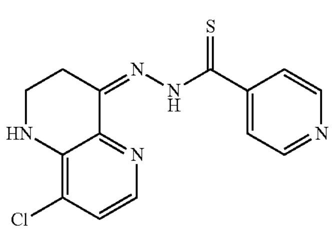 [SMILES: S=C(N/N=C1/CCNc2c(Cl)ccnc21)c1ccncc1] | 318.05 |

-continued

| Example number | Structure | Mass (MH+) |
|---|---|---|
| 57 | 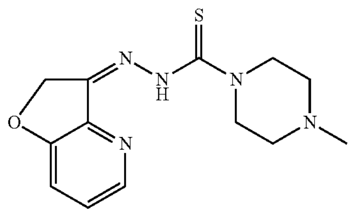 [SMILES: CN1CCN(C(=S)N/N=C2/COc3cccnc32)CC1] | 292.12 |
| 58 | 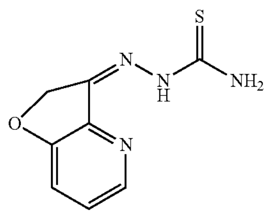 [SMILES: NC(=S)N/N=C1/COc2cccnc21] | 209.04 |
| 59 | 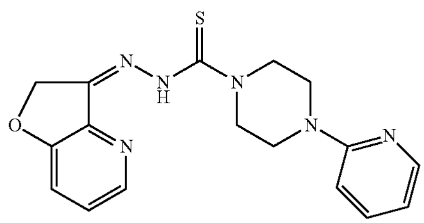 [SMILES: S=C(N/N=C1/COc2cccnc21)N1CCN(c2ccccn2)CC1] | 355.13 |
| 60 | 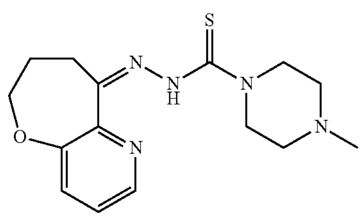 [SMILES: CN1CCN(C(=S)N/N=C2/CCCOc3cccnc32)CC1] | 320.15 |
| 61 | 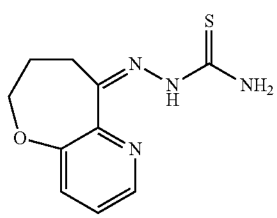 [SMILES: NC(=S)N/N=C1/CCCOc2cccnc21] | 237.07 |
| 62 | 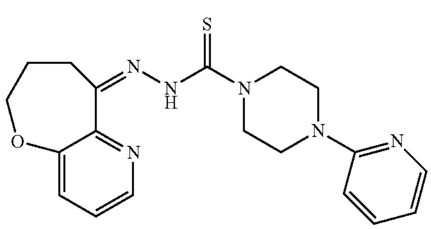 [SMILES: S=C(N/N=C1/CCCOc2cccnc21)N1CCN(c2ccccn2)CC1] | 383.16 |
| 63 | 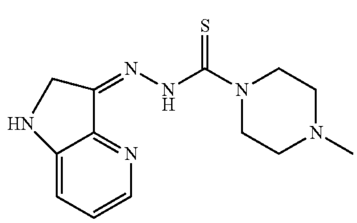 [SMILES: CN1CCN(C(=S)N/N=C2/CNc3cccnc32)CC1] | 291.13 |

-continued

| Example number | Structure | Mass (MH+) |
|---|---|---|
| 64 | 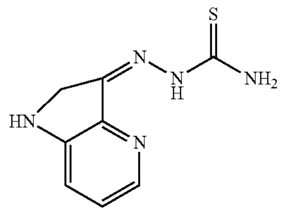 [SMILES: NC(=S)N/N=C1/CNc2cccnc21] | 208.06 |
| 65 | 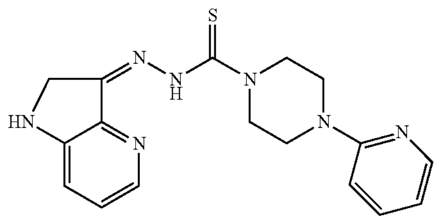 [SMILES: S=C(N/N=C1/CNc2cccnc21)N1CCN(c2ccccn2)CC1] | 254.14 |
| 66 | 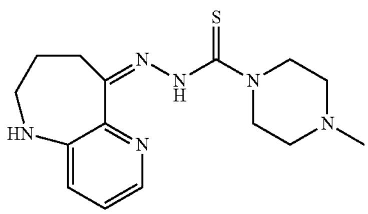 [SMILES: CN1CCN(C(=S)N/N=C2/CCCNc3cccnc32)CC1] | 319.16 |
| 67 | 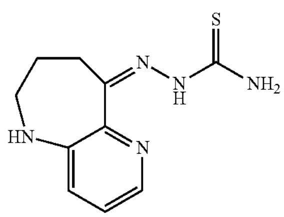 [SMILES: NC(=S)N/N=C1/CCCNc2cccnc21] | 236.09 |
| 68 | 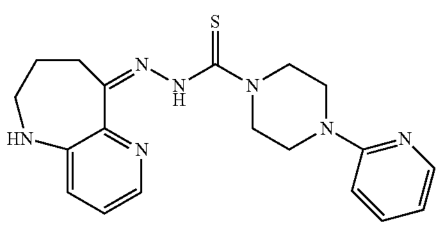 [SMILES: S=C(N/N=C1/CCCNc2cccnc21)N1CCN(c2ccccn2)CC1] | 382.17 |
| 69 | 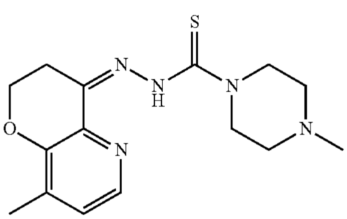 [SMILES: Cc1ccnc2c1OCC/C2=N/NC(=S)N1CCN(C)CC1] | 320.15 |
| 70 | 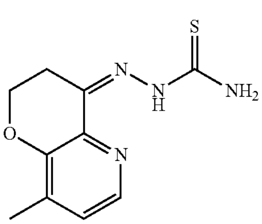 [SMILES: Cc1ccnc2c1OCC/C2=N/NC(N)=S] | 237.07 |

| Example number | Structure | Mass (MH+) |
|---|---|---|
| 71 | 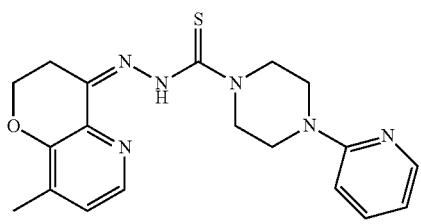 [SMILES: Cc1ccnc2c1OCC/C2=N/NC(=S)N1CCN(c2ccccn2)CC1] | 383.16 |
| 72 | 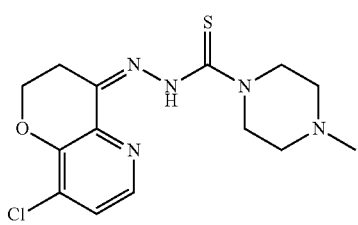 [SMILES: CN1CCN(C(=S)N/N=C2/CCOc3c(Cl)ccnc32)CC1] | 340.09 |
| 73 | 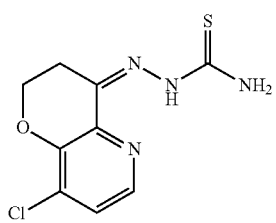 [SMILES: NC(=S)N/N=C1/CCOc2c(Cl)ccnc21] | 257.02 |
| 74 | 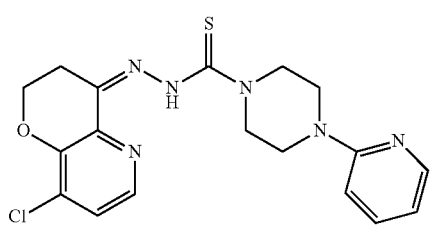 [SMILES: S=C(N/N=C1/CCOc2c(Cl)ccnc21)N1CCN(c2ccccn2)CC1] | 403.10 |
| 75 | 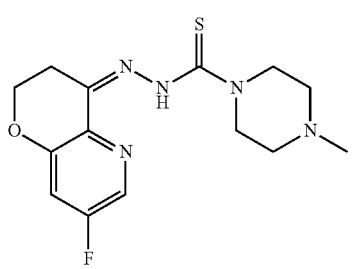 [SMILES: CN1CCN(C(=S)N/N=C2/CCOc3cc(F)cnc32)CC1] | 324.12 |
| 76 | 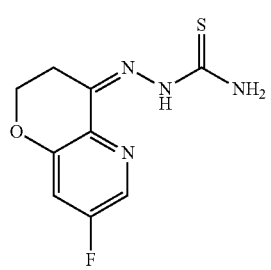 [SMILES: NC(=S)N/N=C1/CCOc2cc(F)cnc21] | 241.05 |

-continued
| Example number | Structure | Mass (MH+) |
|---|---|---|
| 77 | 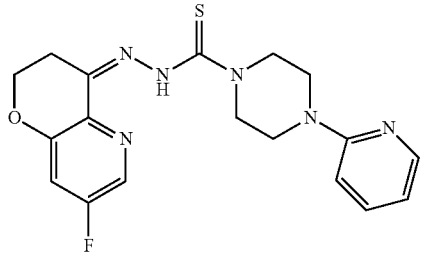 [SMILES: Fc1cnc2c(c1)OCC/C2=N/NC(=S)N1CCN(c2ccccn2)CC1] | 387.13 |
| 78 | 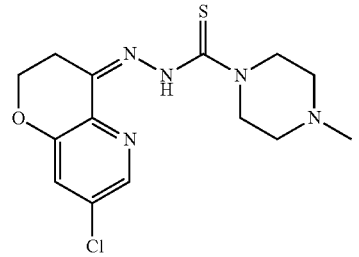 [SMILES: CN1CCN(C(=S)N/N=C2/CCOc3cc(Cl)cnc32)CC1] | 340.09 |
| 79 | 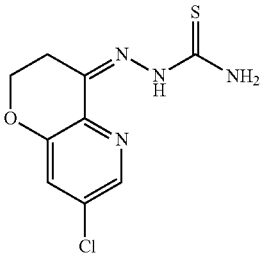 [SMILES: NC(=S)N/N=C1/CCOc2cc(Cl)cnc21] | 257.02 |
| 80 | 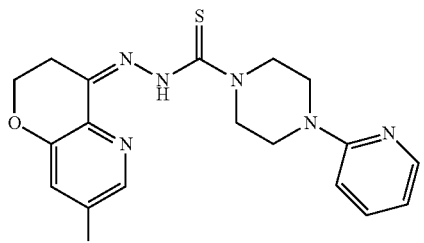 | 403.10 |
| 81 | 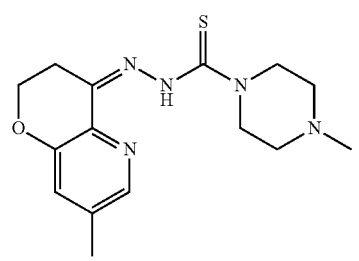 [SMILES: Cc1cnc2c(c1)OCC/C2=N/NC(=S)N1CCN(C)CC1] | 320.15 |
| 82 | 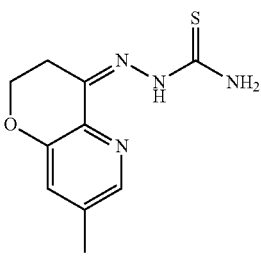 [SMILES: Cc1cnc2c(c1)OCC/C2=N/NC(N)=S] | 237.07 |

-continued

| Example number | Structure | Mass (MH+) |
|---|---|---|
| 83 | 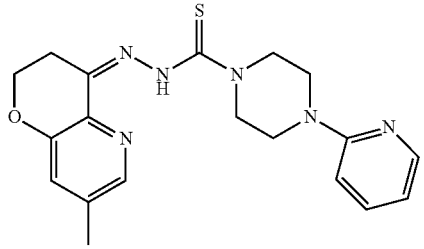 [SMILES: Cc1cnc2c(c1)OCC/C2=N/NC(=S)N1CCN(c2ccccn2)CC1] | 383.16 |
| 84 | 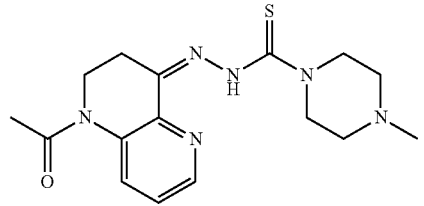 [SMILES: CC(=O)N1CC/C(=N/NC(=S)N2CCN(C)CC2)c2ncccc21] | 347.16 |
| 85 | 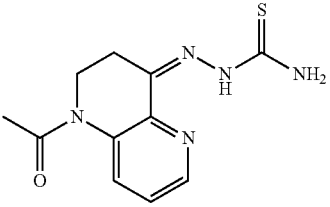 [SMILES: CC(=O)N1CC/C(=N/NC(N)=S)c2ncccc21] | 263.09 |
| 86 | 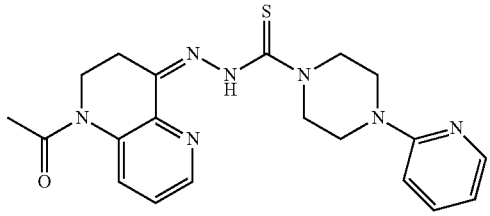 [SMILES: CC(=O)N1CC/C(=N/NC(=S)N2CCN(c3ccccn3)CC2)c2ncccc21] | 410.17 |

Exemplary Activity Against Various Cancer Cells

Human tumor cell lines were grown in RPM(1640 medium containing 5% fetal bovine serum and 2 mM L-glutamine. For a typical screening experiment, cells were inoculated into 96 well microtiter plates in 100 µL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of Compound 3 above.

After 24 h, two plates of each cell line were fixed in situ with TCA, to represent a measurement of the cell population for each cell line at the time of drug addition (Tz). Experimental drugs were solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 µg/mL gentamicin. Additional four, 10-fold or ½ log serial dilutions were made to provide a total of five drug concentrations plus control. Aliquots of 100 µl of these different drug dilutions were added to the appropriate microtiter wells already containing 100 µl of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 µl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 µl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth was calculated at each of the drug concentrations levels. Percentage growth inhibition was calculated as: [(Ti-Tz)/(C-Tz)]×100 for concentrations for which Ti>/=Tz [(Ti-Tz)/Tz]×100 for concentrations for which Ti<Tz. Three dose response parameters were calculated for each experimental agent. Growth inhibition of 50% (GI50) was calculated from [(Ti-Tz)/(C-Tz)]×100=50, which is the drug concentration resulting in a 50% reduction in the net protein increase (as measured by SRB staining) in control cells during the drug incubation. Growth inhibition of 50% ($GI_{50}$) of Compound 3 was listed in Table 3.

| Cell Line Name | Panel Name | GI50 (nM) |
|---|---|---|
| CCRF-CEM | Leukemia | <10 |
| HL-60(TB) | Leukemia | 14.9 |
| K-562 | Leukemia | <10 |
| MOLT-4 | Leukemia | <10 |
| RPMI-8226 | Leukemia | <10 |
| SR | Leukemia | 65.5 |
| A549/ATCC | Non-Small Cell Lung Cancer | 155 |
| EKVX | Non-Small Cell Lung Cancer | 140 |
| HOP-62 | Non-Small Cell Lung Cancer | 37.2 |
| HOP-92 | Non-Small Cell Lung Cancer | 16.7 |
| NCI-H226 | Non-Small Cell Lung Cancer | 338 |
| NCI-H23 | Non-Small Cell Lung Cancer | 32.1 |
| NCI-H322M | Non-Small Cell Lung Cancer | 221 |
| NCI-H460 | Non-Small Cell Lung Cancer | 38.8 |
| NCI-H522 | Non-Small Cell Lung Cancer | 505 |
| COLO 205 | Colon Cancer | <10 |
| HCC-2998 | Colon Cancer | 701 |
| HCT-116 | Colon Cancer | <10 |
| HCT-15 | Colon Cancer | <10 |
| HT29 | Colon Cancer | <10 |
| KM12 | Colon Cancer | 225 |
| SW-620 | Colon Cancer | <10 |
| SF-268 | CNS Cancer | 410 |
| SF-295 | CNS Cancer | 232 |
| SF-539 | CNS Cancer | 1160 |
| SNB-19 | CNS Cancer | 433 |
| SNB-75 | CNS Cancer | 1080 |
| U251 | CNS Cancer | 26.5 |
| LOX IMVI | Melanoma | 25.1 |
| MALME-3M | Melanoma | 1290 |
| M14 | Melanoma | 37.5 |
| MDA-MB-435 | Melanoma | 271 |
| SK-MEL-2 | Melanoma | 799 |
| SK-MEL-28 | Melanoma | 472 |
| SK-MEL-5 | Melanoma | 222 |
| UACC-257 | Melanoma | 11.8 |
| UACC-62 | Melanoma | 170 |
| IGROV1 | Ovarian Cancer | <10 |
| OVCAR-3 | Ovarian Cancer | <10 |
| OVCAR-4 | Ovarian Cancer | 16.5 |
| OVCAR-5 | Ovarian Cancer | 991 |
| OVCAR-8 | Ovarian Cancer | 37.4 |
| NCI/ADR-RES | Ovarian Cancer | 37.4 |
| SK-OV-3 | Ovarian Cancer | 82.0 |
| 786-0 | Renal Cancer | 77.1 |
| A498 | Renal Cancer | 192 |
| ACHN | Renal Cancer | 196 |
| CAKI-1 | Renal Cancer | 151 |
| RXF 393 | Renal Cancer | 1340 |
| SN12C | Renal Cancer | 1490 |
| TK-10 | Renal Cancer | 748 |
| UO-31 | Renal Cancer | 132 |
| PC-3 | Prostate Cancer | <10 |
| DU-145 | Prostate Cancer | 345 |
| MCF7 | Breast Cancer | <10 |
| MDA-MB-231/ATCC | Breast Cancer | 74.8 |
| HS 578T | Breast Cancer | 754 |
| BT-549 | Breast Cancer | 71.8 |
| T-47D | Breast Cancer | <10 |
| MDA-MB-468 | Breast Cancer | <10 |

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used in the description herein and throughout the claims that follow, the meaning of "a," "an," and "the" includes plural reference unless the context clearly dictates otherwise. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:
1. A compound having a structure according to Formula Id, Ie, Ig, or Ih

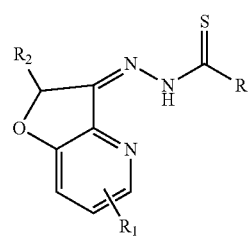

Id

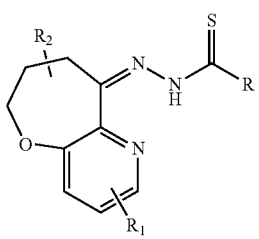

Ie

-continued

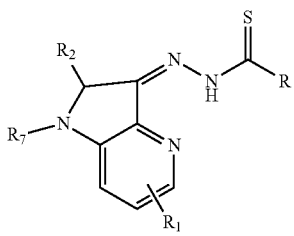

Ig

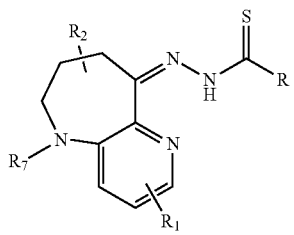

Ih wherein:
$R_1$ is hydrogen, F, Cl, Br, I, CN, $C_1$-$C_4$ alkyl, $C_1$-$C_6$ alkoxy, $C_2$-$C_6$ alkenyl, $CF_3$, $CHF_2$, $CH_2F$, $C_2$-$C_6$ alkynyl, or $CON(R_5)R_6$;
$R_2$ is hydrogen, alkyl, cycloalkyl, alkenyl, alkynyl, alkylthio, aryl, arylalkyl, or oxo;
R is (i), (ii), or (iii), wherein:
  (i) is heteroaryl or aryl, each of which is substituted with from 0 to 4 substituents selected from the group of halogen, hydroxy, cyano, $CF_3$, $CHF_2$, $CH_2F$, —COOH, —$SO_2NH_2$, oxo, nitro, $C_1$-$C_4$ alkyl, $C_1$-$C_6$ alkoxy, $C_2$-$C_6$ alkenyl, $C_2$-$C_6$ alkynyl, CON($R_5$)$R_6$, $SO_2N(R_5)R_6$, and $N(R_7)R_8$;
  (ii) is $C_1$-$C_4$ alkyl, $C_1$-$C_6$ alkoxy, $C_2$-$C_6$ alkenyl, $C_2$-$C_6$ alkynyl, CON($R_5$)$R_6$, or $N(R_7)R_8$;
  (iii) is a group having the formula (A):

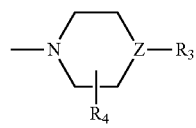

(A)

wherein:
$R_3$ is selected from the group consisting of hydrogen, $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$cycloalkyl)$C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- or di-($C_3$-$C_8$ cycloalkyl)amino$C_0$-$C_4$alkyl, (4- to 7-membered heterocycle) $C_0$-$C_4$alkyl, $C_1$-$C_6$ alkylsulfonyl, mono- or di-($C_1$-$C_6$ alkyl) sulfonamido, and mono- or di-($C_1$-$C_6$ alkyl) aminocarbonyl, each of which is substituted with from 0 to 4 substituents independently selected from the group consisting of halogen, hydroxy, cyano, amino, —COOH, nitro, $CF_3$, and oxo;
$R_4$ is hydrogen, $C_1$-$C_4$ alkyl, or oxo;
Z is CH when $R_3$ is hydrogen, or Z—$R_3$ is O, or Z is N; and
$R_5$ and $R_6$ are independently selected from the group consisting of hydrogen, $C_1$-$C_4$ alkyl, cycloalkyl, alkenyl, and alkynyl; and $R_7$ and $R_8$ are independently selected from the group consisting of hydrogen, $C_1$-$C_4$ alkyl, $C_2$-$C_6$ alkenyl, $C_2$-$C_6$ alkynyl, $C_3$-$C_{10}$ aryl or heteroaryl, $C_2$-$C_6$ acyl, $C_1$-$C_6$ alkoxycarbonyl, and $C_2$-$C_6$ alkanoyloxy, each of which is substituted with from 0 to 4 substituents independently selected from the group consisting of halogen, hydroxy, cyano, amino, —COOH, nitro, $CF_3$, and oxo.

2. The compound of claim 1 having a structure according to Formula Id

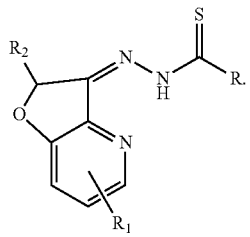

(Id)

3. The compound of claim 1 having a structure according to Formula Ie

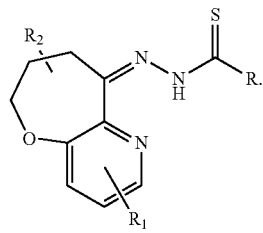

(Ie)

4. The compound of claim 1 having a structure according to Formula Ig

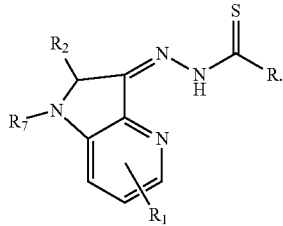

(Ig)

5. The compound of claim 1 having a structure according to Formula Ih

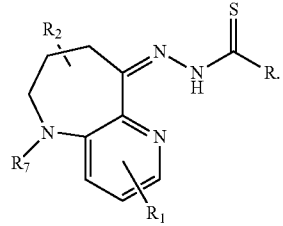

(Ih)

6. The compound of claim 1 wherein R is (iii), and wherein Z is N.

7. The compound of claim 1 wherein $R_1$ is F, Cl, or $C_1$-$C_4$ alkyl.

8. The compound of claim 1 wherein $R_2$ is hydrogen.

9. A pharmaceutical composition, comprising a pharmaceutically acceptable carrier in combination with a compound according to claim 1.

10. The pharmaceutical composition of claim 9, wherein the composition is formulated for oral administration or injection.

11. A method for treating a disorder in a patient in need thereof, wherein the disorder is selected from the group consisting of a nasal cavity tumor, paranasal sinus tumor, nasopharyngeal tumor, oral cavity tumor, oropharyngeal tumor, laryngeal tumor, hypopharyngeal tumor, salivary gland tumor, a paraganglioma, liver cancer, biliary tree cancer, intestinal cancer, ovarian cancer, skin cancer, pancreatic cancer, gastric cancer, lung cancer, breast cancer, a sarcoma, a cancer of the central nervous system, and a lymphoma, the method comprising: administering to the patient an effective amount of a compound of claim 1.

* * * * *